US012570605B2

(12) United States Patent
Xu et al.

(10) Patent No.: US 12,570,605 B2
(45) Date of Patent: Mar. 10, 2026

(54) INDOLE COMPOUNDS, AND PREPARATION METHODS, AND USES THEREOF

(71) Applicant: Shenzhen 01 Life Science and Technology Co., Ltd., Shenzhen (CN)

(72) Inventors: Xiaoqiang Xu, Shenzhen (CN); Xiaokai Wang, Shenzhen (CN); Yao Ma, Shenzhen (CN); Xianbin Zhong, Shenzhen (CN)

(73) Assignee: Shenzhen 01 Life Science and Technology Co., Ltd., Shenzhen (CN)

( * ) Notice: Subject to any disclaimer, the term of this patent is extended or adjusted under 35 U.S.C. 154(b) by 119 days.

(21) Appl. No.: 18/270,743

(22) PCT Filed: Sep. 2, 2022

(86) PCT No.: PCT/CN2022/116740
§ 371 (c)(1),
(2) Date: Jul. 3, 2023

(87) PCT Pub. No.: WO2023/030487
PCT Pub. Date: Mar. 9, 2023

(65) Prior Publication Data
US 2024/0174606 A1 May 30, 2024

(30) Foreign Application Priority Data
Sep. 3, 2021 (CN) ......................... 202111029883.5

(51) Int. Cl.
*C07D 209/12* (2006.01)
*A61K 31/404* (2006.01)
*A61P 17/00* (2006.01)

(52) U.S. Cl.
CPC .......... *C07D 209/12* (2013.01); *A61K 31/404* (2013.01); *A61P 17/00* (2018.01)

(58) Field of Classification Search
CPC ........ C07D 209/12; A61P 17/00; A61P 11/06; A61P 29/00; A61P 37/06; A61P 37/00;
(Continued)

(56) References Cited

U.S. PATENT DOCUMENTS

2018/0110757 A1 4/2018 Bautista et al.
2019/0284149 A1 9/2019 Song et al.

FOREIGN PATENT DOCUMENTS

AU 2017389794 B2 7/2018
CN 1351599 A 5/2002
(Continued)

OTHER PUBLICATIONS

Lavrenov, S.N. et al., N-(Hydroxyalkyl) Derivatives of tris(1H-indol-3-yl)methylium Salts as Promising Antibacterial Agents: Synthesis and Biological Evaluation, Pharmaceuticals 2020, 13(12), p. 469.
(Continued)

*Primary Examiner* — Taylor V Oh

(57) ABSTRACT

A class of indole compounds is provided, their preparation methods and use thereof, which belong to the technical field of pharmaceutical chemistry. The compounds represented by formula I have a well therapeutic effect on atopic dermatitis.

I

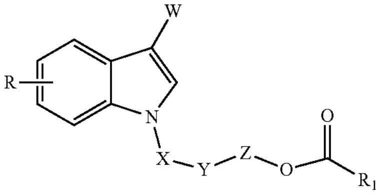

14 Claims, 15 Drawing Sheets

(58) Field of Classification Search
CPC . A61K 31/404; A61K 31/405; C07B 2200/13
USPC .......................................................... 514/415
See application file for complete search history.

(56) References Cited

FOREIGN PATENT DOCUMENTS

| | | | |
|---|---|---|---|
| CN | 102770425 | A | 11/2012 |
| CN | 106008346 | A | 10/2016 |
| CN | 110368385 | A | 10/2019 |
| EP | 0022634 | A1 | 1/1981 |
| EP | 1595866 | A1 | 11/2005 |
| GB | 2457040 | A | 8/2009 |
| WO | 1995016687 | A1 | 6/1995 |
| WO | 2000071535 | A1 | 11/2000 |
| WO | 2005044260 | A1 | 5/2005 |
| WO | 2006069196 | A1 | 6/2006 |
| WO | 2006105796 | A1 | 10/2006 |
| WO | 2009108551 | A2 | 9/2009 |
| WO | 2011079102 | A1 | 6/2011 |

OTHER PUBLICATIONS

Vo, Q.V. et al., In silico study of the radical scavenging activities of natural indole-3-carbinols, Journal of Chemical Information and Modeling, 2019, 60(1), pp. 316-321.
Zhang, J. et al., Synthesis and characterization of photorefractive polymers containing indole groups, Research on Chemical Intermediates, 2014, 40, pp. 2963-2972.
Examination Report No. 1 for Standard Patent Application AU2022337841 mailed on May 9, 2024.
International Search Report for PCT /CN2022/116740, mailed on Dec. 7, 2022.
Vo. Q. V. et al. "In Silico Study of the Radical Scavenging Activities of NaturalIndole-3-Carbinols" Journal of ChemicalInj(Jrmation and Modeling, vol. 60, No. 1, Dec. 16, 2019 (Dec. 16, 2019), ISSN: 1549-9596,pp. 316-321.
Li, Xiang et al. "Aerobic Transition-Metal-Free Visible-Light Photoredox Indole C-3 Formylation Reaction" ACS Catalysis, vol. 4, No. 6, OS May 2014 (May 5, 2014), ISSN: 2155-5435, pp. 1897-1900.
Moon, H. et al. "Synthesis and Properties of Photorefractive Polymers Containing IndoleBased Multifunctional Chromophore as a Pendant Group" Macromolecules, vol. 33, No. 14, Jun. 22, 2000 (Jun. 22, 2000), ISSN: 0024-9297, pp. 5116-5123.
Chang-Jiang Xu et al., Lewis Basic Amine Catalyzed Aza-Michael Reaction of Indole- and Pyrrole-3-carbaldehydes, Synthesis, 2020, 52(18), pp. 2650-2661.
Baird Kenneth J et al., The Preparation and Rearrangement of 1-Prenylinwles and 3-Prenylindolenines, Heterocycles, 1981, 15(2).
J. Hwang et al., Synthesis and characterization of photoconducting non-linear optical polymers containing indole-benzoxazole moiety, Polymer, Elsevier, 2001, 42(7), pp. 3023-3031.
Oct. 29, 2024 1st Office Action issued in Russian Patent Application No. RU2024108809.
Nov. 26, 2024 Notice of Reasons for Refusal issued in Japanese Patent Application No. 2023-541515.
Nov. 25, 2024 extended European search report issued in European Patent Application No. 22863621.3.
Dec. 28, 2024 1st Office Action issued in Chinese Patent Application No. 202211070117.8.
Feb. 21, 2025 1st Office Action issued in Canadian Patent Application No. 3,230,066.
May 13, 2025 2nd Office Action issued in Japanese Patent Application No. 2023-541515.
Database Registry [Online], CAS Registry No. 2031128-46-6(Nov. 14, 2016), 329909-48-0(Apr. 4, 2001), 1609386-96-0(Jun. 2, 2014), 1428063-58-4(Apr. 11, 2013), 1313042-15-7(Jul. 19, 2011), 912355-30-7(Nov. 3, 2006), 912355-28-3 (Nov. 3, 2006), 912355-25-0(Nov. 3, 2006), 753488-05-0(Sep. 29, 2004), 287978-14-7(Aug. 31, 2000), 77992-73-5(Nov. 16, 1984).
Oct. 22, 2025 1st Office Action issued in Korean Patent Application No. 10-2024-7010632.

INDOLE COMPOUNDS, AND PREPARATION METHODS, AND USES THEREOF

CROSS-REFERENCE TO RELATED APPLICATIONS

This application claims priority to PCT Application No. PCT/CN2022/116740, having a filing date of Sep. 2, 2022, which is based on Chinese Application No. 202110279883.5, having a filing date of Sep. 3, 2021, the entire contents both of which are hereby incorporated by reference.

FIELD OF TECHNOLOGY

The following relates to the technical field of pharmaceutical chemistry, and particularly, it relates to an indole compound, a preparation method, and a use thereof.

BACKGROUND

Atopic dermatitis (ADs) is a chronic recurrent inflammatory skin disease. It is reported that many factors are involved in the pathophysiology of AD, including genetics factors, environmental factors, changes in the composition of epidermis lipid, immune dysfunction, and microbial dysregulation. In addition to skin symptoms such as erythema, papula, exudation, desquamation, xerosis, plaques, and lichenification, AD can also cause mental illness and increase the risk of cardiovascular diseases. Furthermore, it is also thought to be related to depression and suicidal tendencies. From the perspective of epidemiological characteristics, AD is more common in children, and most symptoms continue to exist in the adult stage. The statistical analysis of the relevant clinical data in the United States has been well studied, and the results of studies on children and adolescent populations show that only 1% of patients who suffered from this disease before the age of 12 would not continue to have the disease afterwards.

Relevant studies have shown that the prevalence rate of AD in China is gradually increasing, especially in children, and the prevalence rate in urban areas is higher than that in rural areas. In conclusion, AD has a significant impact on the life quality and the mental health state for patients. The continuous increase in the prevalence rate of AD in recent years, especially in urban children, has raised a clinical and social request for the development of safer and more effective AD treatment drugs and protocols.

At present, traditional drugs for AD treatment are mainly divided into three types: 1) moisturizers that improve the dry skin condition; 2) corticosteroids that have broad anti-inflammatory and immunosuppressive effects; and 3) calcineurin inhibitors that alleviate inflammation by binding to immunophilin to inhibit calcineurin, and ultimately inhibiting the secretion of various cytokines. In addition, since AD patients often suffer from *Staphylococcus aureus* infections, they are more susceptible to fungal infections than healthy people, and therefore antibiotics can be used systematically to eliminate pathogenic microbes for alleviating AD conditions. However, the above traditional treatment methods have their limitations: 1) the moisturizer mainly functions to slow down the volatilization of skin moisture, and its therapeutic effect is limited; 2) long-term use of the corticosteroid can cause systemic adverse effects and inhibit the hypothalamic-pituitary-adrenal (HPA) axis, and the use in children may have adverse effects on their development; 3) the calcineurin inhibitor often causes local burning and itching; 4) after the antibiotic is taken off, the pathogenic microbes are prone to recolonization, and long-term use of the antibiotic may induce drug-resistant strains.

Since the pathophysiology of AD is closely related to epidermal barrier dysfunction and immune dysfunction, AD patients often show abnormal expression of cytokines. Some researchers have proposed to classify AD into different endotypes according to the molecular mechanisms associated with different pathological phenotypes. In recent years, small molecule inhibitors targeting cytokine receptors and biologics targeting specific cytokines or their receptors have become hot topics in the development of therapeutic drugs for AD. Small molecule inhibitors against phosphodiesterase (PDE)-4 and Janus kinase (JAK), histamine 4 receptor (H4R) antagonists, aromatic hydrocarbon receptor (AhR) agonists and monoclonal antibodies against interleukin-4 (IL-4) receptor and interleukin-13 (IL-13), etc., are currently in clinical trials or in a stage of clinical approval. Among them, Dupixent (Dupilumab, a monoclonal antibody against IL-4 receptor), Eucrisa (Crisaborole, a topical phosphodiesterase-4 (PDE-4) antagonist), and Cibinqo (Abrocitinib, an oral JAKI inhibitor) have been approved by FDA. Currently, a drug with Benvitimod as a primary active ingredient, serving as both an AhR agonist and a T-cell tyrosine kinase inhibitor, has been approved by the China National Medical Products Administration, but is currently limited to psoriasis treatment. Therefore, in order to solve the problems such as safety and drug resistance caused by long-term use of drugs and improve absorption efficiency of drugs by transdermal administration, it is urgently required to develop more small molecule drugs from natural sources.

SUMMARY

Based on this, it is necessary to provide a class of indole compounds with good therapeutic effect on atopic dermatitis to address the above problems.

An aspect relates to an indole compound having a structure of formula I,

I

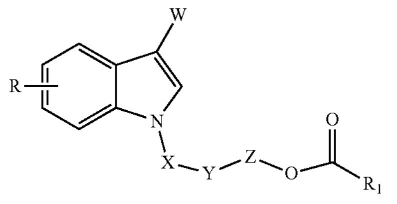

wherein,

W is $COR_2$, or $CR_3R_4OR_5$;

X is absent, or X is CO, or $CR_3R_4$;

Y is absent, or Y is O;

Z is absent, or Z is $CR_3R_4$;

$R_1$ is selected from the group consisting of unsubstituted or substituted $C_{1-20}$ alkyl, unsubstituted or substituted $C_{2-20}$ alkenyl, unsubstituted or substituted aryl, heteroaryl, arylalkyl, heteroarylalkyl, and alkoxy;

R is selected from the group consisting of H, D, unsubstituted or substituted $C_{1-6}$ alkyl, unsubstituted or substituted $C_{2-6}$ alkenyl, unsubstituted or substituted aryl, heteroaryl, halogen, ORS, $NR_6R_7$, $CO_2R_7$, $CONR_6R_7$, $OCOR_8$, $NHCOR_8$, $NHSO_2R_8$, or CN;

each of $R_2$, $R_3$, $R_4$, $R_6$, $R_7$, and $R_8$ is independently selected from the group consisting of H, D, unsubstituted or substituted $C_{1-6}$ alkyl, unsubstituted or substituted $C_{2-6}$ alkenyl, unsubstituted or substituted aryl, and heteroaryl; and $R_5$ is H, D, or $COR_1$.

In one embodiment, the compound has a structure as shown in formula II:

II

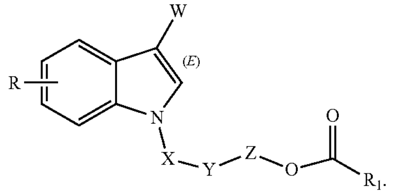

In one embodiment, W is $COR_2$, or $CR_3R_4OR_5$;
X is absent, or X is CO;
Y is absent, or Y is O;
Z is absent, or Z is $CR_3R_4$;
$R_1$ is selected from the group consisting of unsubstituted or substituted $C_{1-20}$ alkyl, unsubstituted or substituted aryl, and alkoxy;
R is H; and
each of $R_2$, $R_3$, $R_4$, and $R_5$ is H.

In one embodiment, $R_1$ is selected from the group consisting of unsubstituted or substituted $C_{5-15}$ alkyl, acetoxyl-substituted aryl, (2,6-dichlorophenyl)amino-substituted aryl, and pentaoxapentadecanyl.

In one embodiment, W is COH, or $CH_2OH$;

X—Y—Z is $COOCH_2$, or $CH_2$;

$R_1$ is selected from $C_7$-$C_{15}$ alkyl, acetoxyl-substituted aryl, (2,6-dichlorophenyl)amino-substituted aryl, and pentaoxapentadecanyl; and R is H.

In one embodiment, W is COH;

X—Y—Z is $CH_2$;

$R_1$ is selected from the group consisting of $C_7$-$C_{15}$ alkyl, acetoxyl-substituted aryl, (2,6-dichlorophenyl)amino-substituted aryl, and pentaoxapentadecanyl; and R is H.

In one embodiment, the compound is selected from the group consisting of:

Compound 1

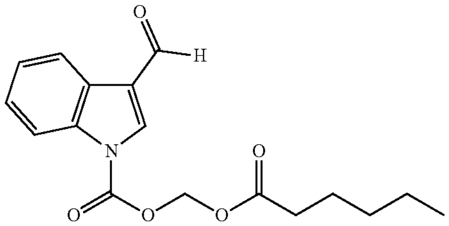

Compound 2

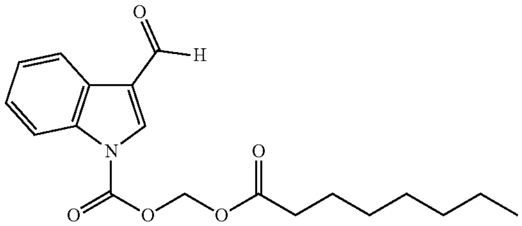

Compound 3

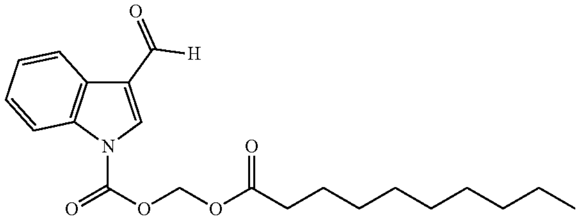

Compound 4

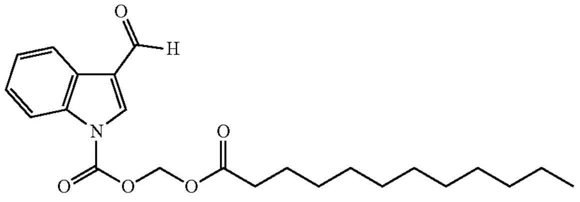

Compound 19

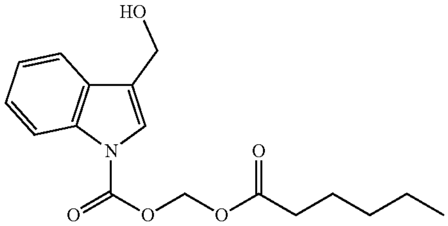

Compound 20

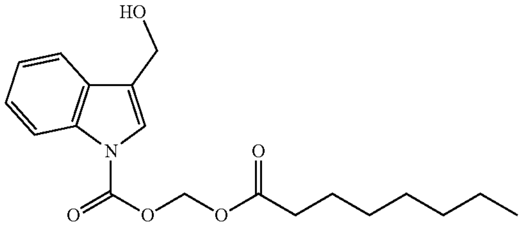

Compound 21

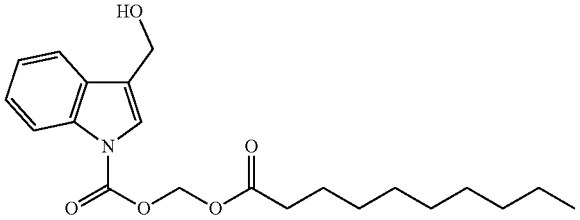

Compound 22

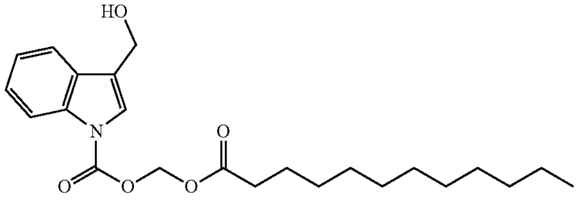

-continued
Compound 5
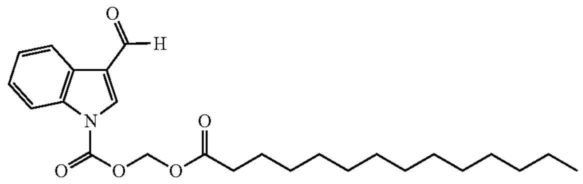
Compound 23
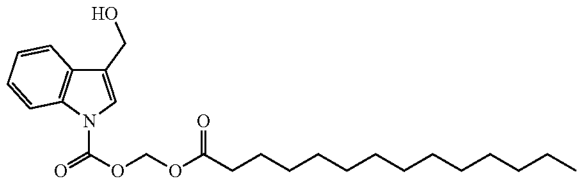
Compound 6
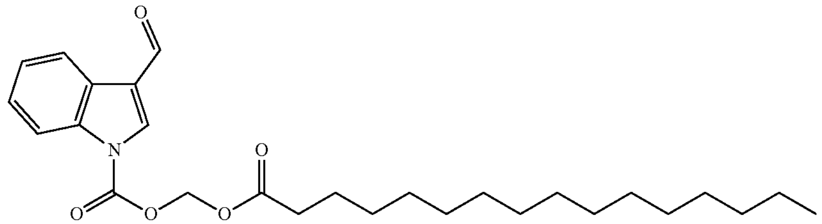
Compound 24
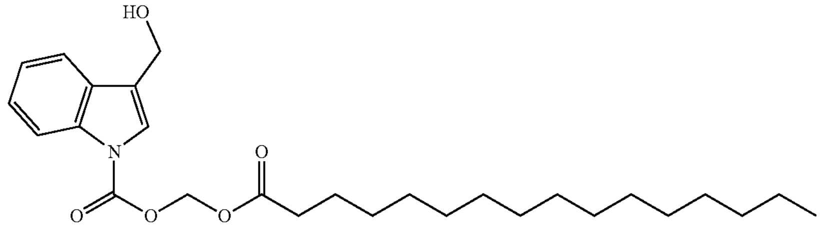
Compound 7
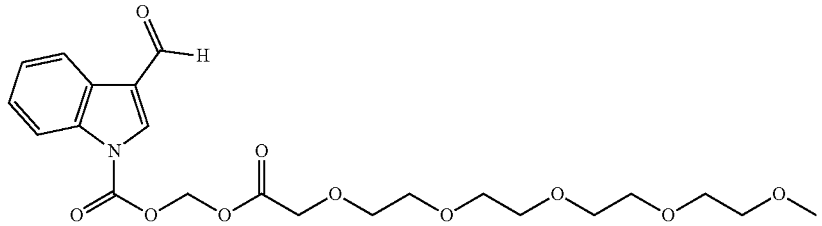
Compound 8
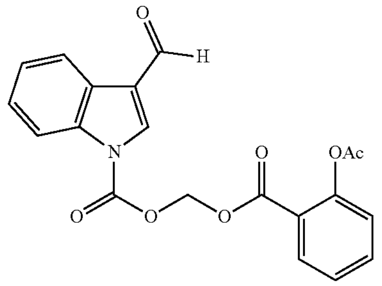
Compound 26
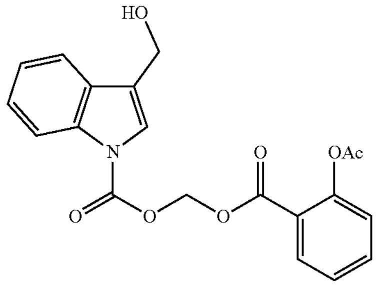
Compound 9
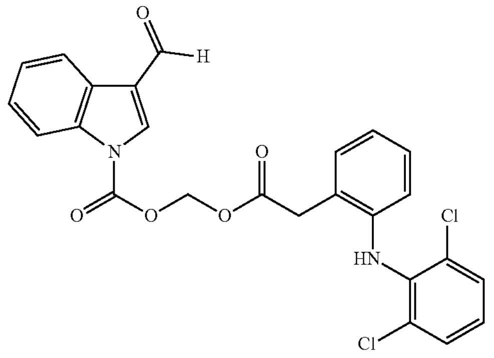
Compound 27
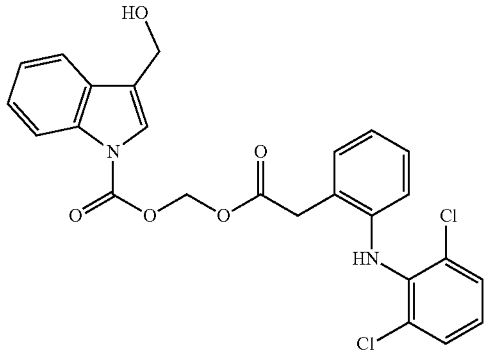

-continued
Compound 28
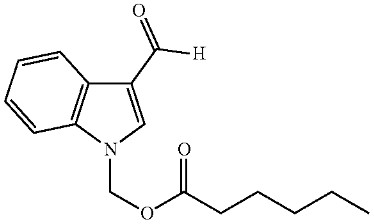
Compound 29
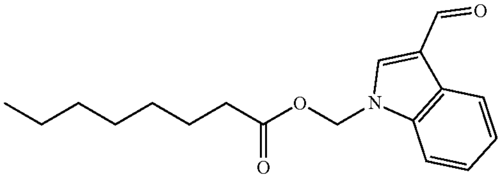
Compound 30
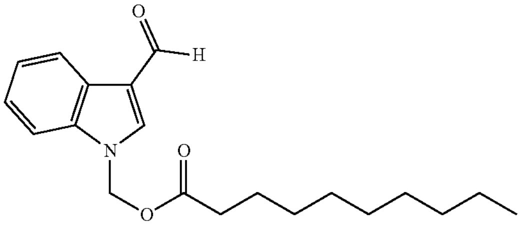
Compound 31
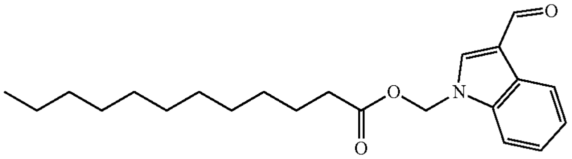
Compound 32
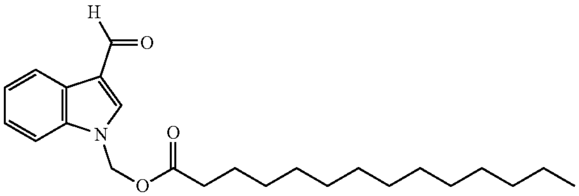
Compound 33
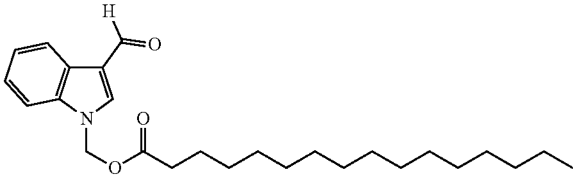
Compound37
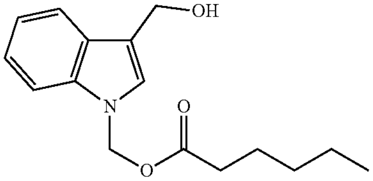
Compound 38
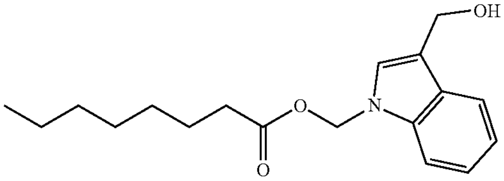
Compound 39
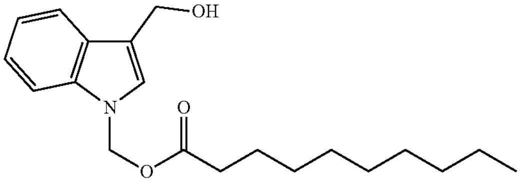
Compound 40
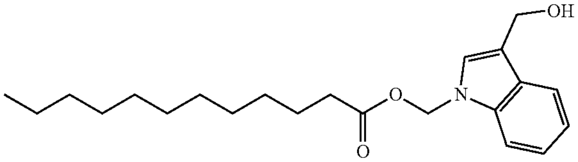
Compound 41
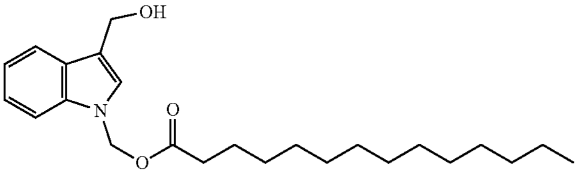
Compound 42
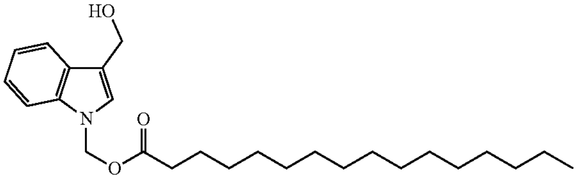
Compound 34
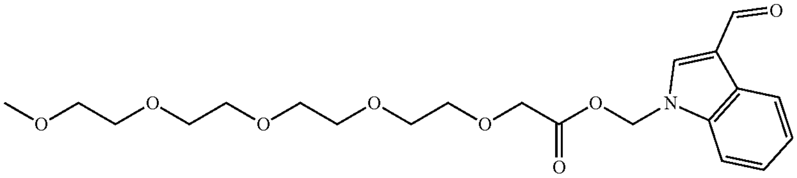
, and -continued Compound 35

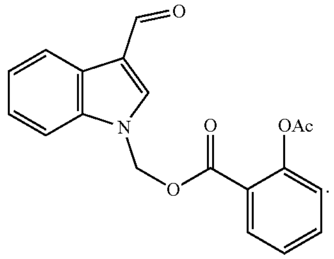

The Compound 4 has characteristic peaks at 2θ of 4.9±0.2°, 7.3±0.2°, 9.9±0.2°, 14.9±0.2°, and 22.0±0.2° in an X-ray powder diffraction pattern using Cu-Kα radiation;

in one embodiment, the Compound 4 has characteristic peaks at 2θ of 4.9±0.2°, 7.3±0.2°, 9.9±0.2°, 11.3±0.2°, 11.8±0.2°, 14.9±0.2°, 19.0±0.2°, 19.9±0.2°, 21.6±0.2°, and 22.0±0.2° in an X-ray powder diffraction pattern using Cu-Kα radiation;

in one embodiment, the Compound 4 has characteristic peaks at 2θ of 4.9±0.2°, 7.3±0.2°, 9.9±0.2°, 10.7±0.2°, 11.3±0.2°, 11.8±0.2°, 13.4±0.2°, 14.6±0.2°, 14.9±0.2°, 18.4±0.2°, 19.0±0.2°, 19.9±0.2°, 21.6±0.2°, 22.0±0.2°, and 25.3±0.2 in an X-ray powder diffraction pattern using Cu-Kα radiation; the Compound 8 has characteristic peaks at 2θ of 5.2±0.2°, 11.6±0.2°, 12.6±0.2°, 16.0±0.2°, and 19.3±0.2° in an X-ray powder diffraction pattern using Cu-Kα radiation;

in one embodiment, the Compound 8 has characteristic peaks at 2θ of 5.2±0.2°, 6.3±0.2°, 10.0±0.2°, 11.6±0.2°, 12.6±0.2°, 12.9±0.2°, 14.3±0.2°, 16.0±0.2°, 19.3±0.2°, and 21.3±0.2° in an X-ray powder diffraction pattern using Cu-Kα radiation;

in one embodiment, the Compound 8 has characteristic peaks at 2θ of 5.2±0.2°, 6.3±0.2°, 10.0±0.2°, 11.6±0.2°, 12.6±0.2°, 12.9±0.2°, 14.3±0.2°, 16.0±0.2°, 19.3±0.2°, 20.4±0.2°, 21.3±0.2°, 23.2±0.2°, 25.2±0.2°, 26.3±0.2°, and 27.6±0.2° in an X-ray powder diffraction pattern using Cu-Kα radiation; the Compound 9 has characteristic peaks at 2θ of 12.3±0.2°, 14.9±0.2°, 19.9±0.2°, 23.4±0.2°, and 27.3±0.2° in an X-ray powder diffraction pattern using Cu-Kα radiation;

in one embodiment, the Compound 9 has characteristic peaks at 2θ of 10.3±0.2°, 12.3±0.2°, 12.7±0.2°, 14.9±0.2°, 15.6±0.2°, 19.2±0.2°, 19.9±0.2°, 23.4±0.2°, 25.1±0.2°, and 27.3±0.2° in an X-ray powder diffraction pattern using Cu-Kα radiation;

in one embodiment, the Compound 9 has characteristic peaks at 2θ of 4.9±0.2°, 10.3±0.2°, 12.3±0.2°, 12.7±0.2°, 14.9±0.2°, 15.6±0.2°, 17.3±0.2°, 19.2±0.2°, 19.9±0.2°, 20.3±0.2°, 20.7±0.2°, 23.4±0.2°, 24.8±0.2°, 25.1±0.2°, and 27.3±0.2° in an X-ray powder diffraction pattern using Cu-Kα radiation;

the Compound 22 has characteristic peaks at 2θ of 3.4±0.2°, 5.3±0.2°, 6.9±0.2°, 10.2±0.2°, and 19.9±0.2° in an X-ray powder diffraction pattern using Cu-Kα radiation;

in one embodiment, the Compound 22 has characteristic peaks at 2θ of 3.4±0.2°, 5.3±0.2°, 6.9±0.2°, 9.7±0.2°, 10.2±0.2°, 11.7±0.2°, 14.9±0.2°, 17.7±0.2°, 19.9±0.2°, and 20.6±0.2° in an X-ray powder diffraction pattern using Cu-Kα radiation;

in one embodiment, the Compound 22 has characteristic peaks at 2θ of 3.4±0.2°, 5.3±0.2°, 6.9±0.2°, 9.7±0.2°, 10.2±0.2°, 11.7±0.2°, 12.5±0.2°, 14.0±0.2°, 14.9±0.2°, 15.4±0.2°, 17.7±0.2°, 19.9±0.2°, 20.6±0.2°, 21.9±0.2°, and 23.2±0.2° in an X-ray powder diffraction pattern using Cu-Kα radiation; the Compound 23 has characteristic peaks at 2θ of 10.6±0.2°, 11.0±0.2°, 18.4±0.2°, 21.2±0.2°, and 21.7±0.2° in an X-ray powder diffraction pattern using Cu-Kα radiation;

in one embodiment, the Compound 23 has characteristic peaks at 2θ of 10.6±0.2°, 11.0±0.2°, 15.2±0.2°, 18.4±0.2°, 19.9±0.2°, 20.6±0.2°, 21.2±0.2°, 21.7±0.2°, 23.6±0.2°, and 24.2±0.2° in an X-ray powder diffraction pattern using Cu-Kα radiation;

in one embodiment, the Compound 23 has characteristic peaks at 2θ of 5.2±0.2°, 10.2±0.2°, 10.6±0.2°, 11.0±0.2°, 13.0±0.2°, 14.0±0.2°, 15.2±0.2°, 18.4±0.2°, 19.9±0.2°, 20.6±0.2°, 21.2±0.2°, 21.7±0.2°, 22.4±0.2°, 23.6±0.2°, and 24.2±0.2° in an X-ray powder diffraction pattern using Cu-Kα radiation;

the Compound 24 has characteristic peaks at 2θ of 4.4±0.2°, 6.6±0.2°, 8.9±0.2°, 21.0±0.2°, and 22.6±0.2° in an X-ray powder diffraction pattern using Cu-Kα radiation;

in one embodiment, the Compound 24 has characteristic peaks at 2θ of 4.4±0.2°, 6.6±0.2°, 8.9±0.2°, 11.1±0.2°, 12.2±0.2°, 13.4±0.2°, 19.5±0.2°, 20.6±0.2°, 21.0±0.2°, and 22.6±0.2° in an X-ray powder diffraction pattern using Cu-Kα radiation;

in one embodiment, the Compound 24 has characteristic peaks at 2θ of 4.4±0.2°, 6.6±0.2°, 8.9±0.2°, 10.4±0.2°, 11.1±0.2°, 12.2±0.2°, 13.4±0.2°, 16.1±0.2°, 17.8±0.2°, 19.5±0.2°, 20.6±0.2°, 21.0±0.2°, 22.6±0.2°, 24.8±0.2°, and 26.5±0.2° in an X-ray powder diffraction pattern using Cu-Kα radiation; the Compound 26 has characteristic peaks at 2θ of 3.6±0.2°, 10.5±0.2°, 11.8±0.2°, 13.9±0.2°, and 19.7±0.2° in an X-ray powder diffraction pattern using Cu-Kα radiation;

in one embodiment, the Compound 26 has characteristic peaks at 2θ of 3.6±0.2°, 7.4±0.2°, 10.5±0.2°, 11.8±0.2°, 13.9±0.2°, 14.9±0.2°, 16.8±0.2°, 19.7±0.2°, 21.2±0.2°, and 23.5±0.2° in an X-ray powder diffraction pattern using Cu-Kα radiation;

in one embodiment, the Compound 26 has characteristic peaks at 2θ of 3.6±0.2°, 7.4±0.2°, 10.5±0.2°, 11.8±0.2°, 13.9±0.2°, 14.9±0.2°, 16.8±0.2°, 19.7±0.2°, 21.2±0.2°, 21.5±0.2°, 22.0±0.2°, 23.5±0.2°, 25.0±0.2°, and 26.0±0.2° in an X-ray powder diffraction pattern using Cu-Kα radiation; the Compound 27 has characteristic peaks at 2θ of 6.5±0.2°, 10.2±0.2°, 13.2±0.2°, 15.0±0.2°, and 23.8±0.2° in an X-ray powder diffraction pattern using Cu-Kα radiation;

in one embodiment, the Compound 27 has characteristic peaks at 2θ of 6.5±0.2°, 10.2±0.2°, 13.2±0.2°, 15.0±0.2°, 16.3±0.2°, 20.2±0.2°, 20.6±0.2°, 21.4±0.2°, 23.8±0.2°, and 27.0±0.2° in an X-ray powder diffraction pattern using Cu-Kα radiation;

in one embodiment, the Compound 27 has characteristic peaks at 2θ of 6.5±0.2°, 10.2±0.2°, 13.2±0.2°, 15.0±0.2°, 16.3±0.2°, 19.3±0.2°, 20.2±0.2°, 20.6±0.2°, 21.4±0.2°, 23.8±0.2°, 24.1±0.2°, 26.0±0.2°, 27.0±0.2°, 27.3±0.2°, and 30.6±0.2° in an X-ray powder diffraction pattern using Cu-Kα radiation;

the Compound 35 has characteristic peaks at 2θ of 12.4±0.2°, 14.7±0.2°, 15.3±0.2°, 17.3±0.2°, and 23.5±0.2° in an X-ray powder diffraction pattern using Cu-Kα radiation;

in one embodiment, the Compound 35 has characteristic peaks at 2θ of 10.8±0.2°, 12.4±0.2°, 13.3±0.2°, 14.7±0.2°, 15.3±0.2°, 17.3±0.2°, 21.8±0.2°, 22.7±0.2°, 23.5±0.2°, and 24.0±0.2° in an X-ray powder diffraction pattern using Cu-Kα radiation;

in one embodiment, the Compound 35 has characteristic peaks at 2θ of 10.8±0.2°, 12.4±0.2°, 13.3±0.2°, 14.7±0.2°, 15.3±0.2°, 17.3±0.2°, 17.8±0.2°, 19.8±0.2°, 21.8±0.2°, 22.7±0.2°, 23.5±0.2°, 24.0±0.2°, 25.6±0.2°, 26.2±0.2°, and 27.4±0.2° in an X-ray powder diffraction pattern using Cu-Kα radiation;

the Compound 41 has characteristic peaks at 2θ of 3.1±0.2°, 5.2±0.2°, 6.7±0.2°, 10.2±0.2°, and 19.9±0.2° in an X-ray powder diffraction pattern using Cu-Kα radiation;

in one embodiment, the Compound 41 has characteristic peaks at 2θ of 3.1±0.2°, 5.2±0.2°, 6.7±0.2°, 9.1±0.2°, 9.8±0.2°, 10.2±0.2°, 11.5±0.2°, 19.9±0.2°, 20.5±0.2°, and 21.6±0.2 in an X-ray powder diffraction pattern using Cu-Kα radiation;

in one embodiment, the Compound 41 has characteristic peaks at 2θ of 3.1±0.2°, 5.2±0.2°, 6.7±0.2°, 9.1±0.2°, 9.8±0.2°, 10.2±0.2°, 10.5±0.2°, 11.5±0.2°, 14.1±0.2°, 14.8±0.2°, 19.3±0.2°, 19.9±0.2°, 20.5±0.2°, 21.6±0.2°, and 23.1±0.2° in an X-ray powder diffraction pattern using Cu-Kα radiation.

It is another aspect to providing a pharmaceutical composition, comprising the above-mentioned compound, and a pharmaceutically acceptable excipient.

In one embodiment, a dosage form of the pharmaceutical composition is a tablet, a dispersing agent, a tincture, a gel, a capsule, a spray, a suppository, an oral liquid, or a granule.

In one embodiment, a dosage form of the pharmaceutical composition is a topical preparation.

It is another aspect to providing use of the compound in the manufacture of a medicament for treating dermatitis and/or an immune system disease.

In one embodiment, the medicament is used to treat atopic dermatitis and/or asthma.

Compared with the conventional art, embodiments of the present invention provide the advantages as follows:

The indole compounds of embodiments of the present invention, structurally optimized based on the lead compounds, namely, a natural small molecule compound IAld (indole-3-carboxaldehyde) and another related small molecule I3C (indole-3-methanol), were verified by a mouse model of calcipotriol (MC903)-induced ear AD-like symptoms. The indole compounds alleviated AD-like symptoms in the ear of the mouse significantly, some of which had even better effects than IAld and I3C, showing promising medicinal prospects.

BRIEF DESCRIPTION

Some of the embodiments will be described in detail, with reference to the following figure, wherein like designations denote like members, wherein.

DETAILED DESCRIPTION

Figure 1:
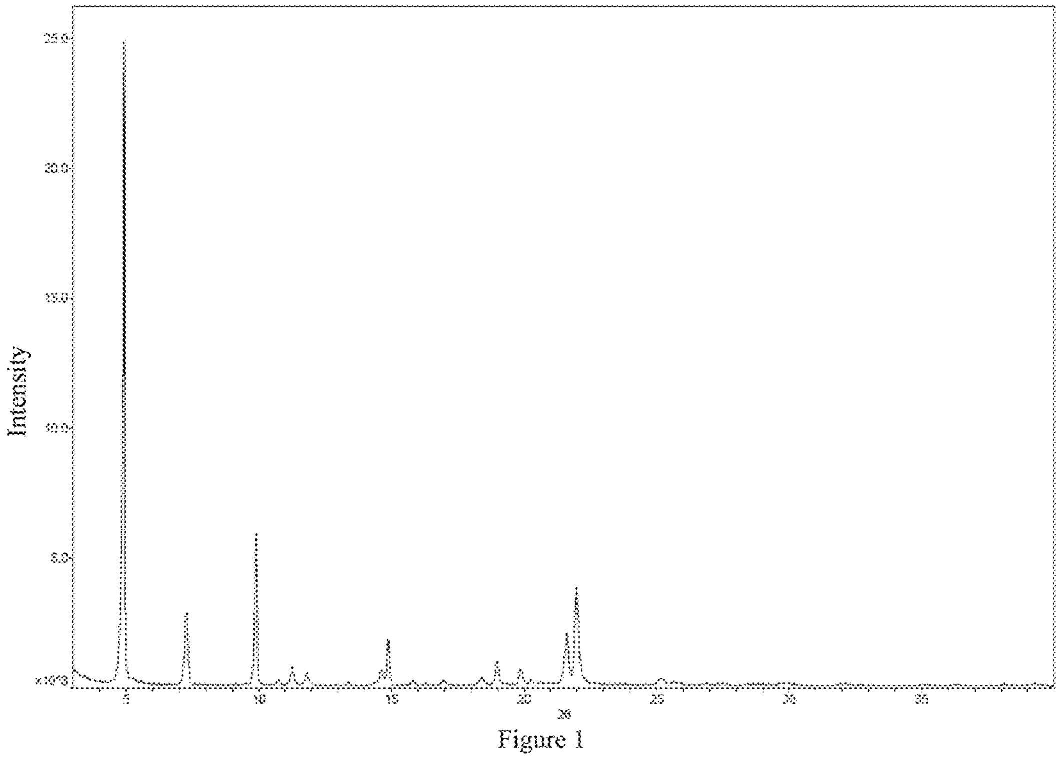
FIG. 1 depicts a XRPD pattern of Compound 4 in Embodiment 7.

For better understanding embodiments of the present invention will be fully described below with reference to the relevant accompanying figures. Embodiments of the invention are shown in the figures. However, embodiments of the present invention can be implemented in many different forms and is not limited to the embodiments described herein. Rather, these embodiments are provided for the purpose of making the disclosed contents of embodiments of the present invention more thorough and complete.

Unless otherwise defined, all technical and scientific terms used herein have the same meaning as those normally understood by one skilled in the conventional art in the technical field of embodiments of the present invention. The terms used in the description of embodiments of the present invention herein are only for the purpose of describing embodiments, and are not intended to limit the present invention. The term "and/or" used herein comprises any one or all combinations of one or more corresponding items listed herein.

The pharmaceutical compositions provided herein may be formulated in any dosage form suitable for topical administration to produce topical or systemic effects, including emulsions, solutions, suspensions, creams, gels, hydrogels, ointments, powders, dressings, elixirs, lotions, suspensions, tinctures, pastes, foams, films, aerosols, flushing fluids, sprays, suppositories, bandages, and skin patches.

Pharmaceutical compositions provided herein for oral administration may be provided in solid, semi-solid, or liquid dosage forms for oral administration.

As used herein, oral administration also includes buccal, tongue or sublingual administration. Suitable oral dosage forms include, but not limited to, tablets, instant tablets, chewable tablets, capsules, pills, strips, troches, lozenges, pastilles, cachets, granules, medical chewable gums, bulk powders, effervescent or non-effervescent powders or granules, oral aerosols, solutions, emulsions, suspensions agents, wafer, sprinkles, elixirs, and syrups. In addition to the active ingredient, the pharmaceutical composition may contain one or more pharmaceutically acceptable excipients including, but not limited to, binders, fillers, diluents, disintegrants, wetting agents, lubricants, glidants, colorants, anti-migrating agents, sweeteners, flavoring agents, emulsifiers, suspending and dispersing agents, preservatives, solvents, non-aqueous liquids, organic acids, and carbon dioxide sources.

Unless otherwise specified, the raw materials used in the following embodiments are commercially available; unless otherwise specified, the methods used in the following embodiments are conventional methods that can be achieved.

The detection parameters of X-ray powder diffraction (XRPD) of the compounds in the following embodiments are shown as follows.

Scan range: 3-40°, scan step: 0.02°, scan rate: 0.1°/step, copper target, wavelength: 1.54 Å.

Embodiment 1

Preparation of (hexanoyloxy) methyl 3-formyl-1H-indole-1-carboxylate (Compound 1)

(1) Synthesis of chloromethyl 3-formyl-1H-indole-1-carboxylate (Compound B)

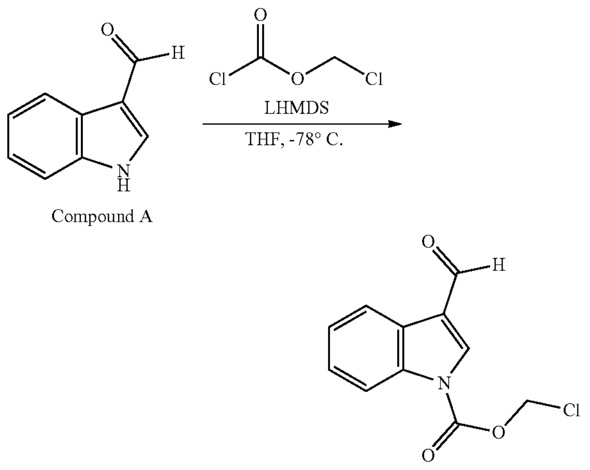

Compound A

Compound B 1H-indole-3-carboxaldehyde (Compound A, 5.0 g, 34 mmol) was dissolved in anhydrous tetrahydrofuran (THF) (60 ml) under the argon protection, and then after the temperature was decreased to −78° C., a solution of lithium bis(trimethylsilyl)amide (LHMDS) in THF (1M, 51.7 ml, 51.7 mmol) was dropwise dripped into the mixture and reacted for 1 hour at −78° C. Subsequently, a solution of chloromethyl chloroformate (6.62 g, 51.7 mmol) in THF (20 mL) was dripped into the reaction liquid and reacted for 2 hours at −78° C. TLC (petroleum ether/ethyl acetate=5:1) showed that the reaction was completed.

Saturated ammonia chloride aqueous solution (50 ml) was added to the reaction liquid, followed by extracting by ethyl acetate (3×40 mL). Then, the organic phases were combined, washed by water (80 mL) and saturated saline (80 mL), dried by anhydrous sodium sulfate, filtered, concentrated under reduced pressure, and purified through a chromatographic column (eluent:petroleum ether:ethyl acetate=100:1 to 1:1), to obtain a yellow solid, i.e. a desirable compound, chloromethyl 3-formyl-1H-indole-1-carboxylate (2) (3.0 g, yield: 37.5%).

The characteristic data of Compound B was: 1H NMR (400 MHz, DMSO) δ 10.10 (s, 1H), 8.77 (s, 1H), 8.17 (dd, J=7.9, 3.2 Hz, 2H), 7.55-7.40 (m, 2H), 6.25 (s, 2H).

(2) Synthesis of (hexanoyloxy)methyl 3-formyl-1H-indole-1-carboxylate (Compound 1)

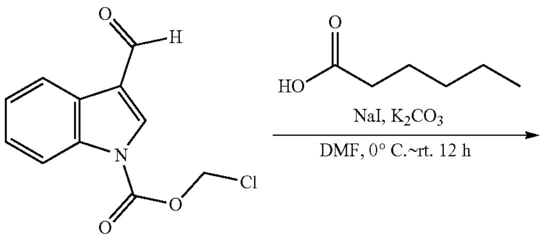

Compound B

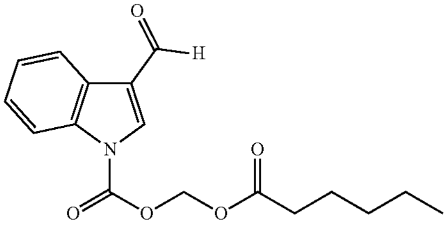

Compound 1

Sodium iodide (252 mg, 1.69 mmol) and potassium carbonate (1.4 g, 10.11 mmol) were added to a solution of chloromethyl 3-formyl-1H-indole-1-carboxylate (Compound B) (800 mg, 3.37 mmol) and hexanoic acid (391 mg, 3.37 mmol) in anhydrous DMF (8.0 ml) at 0° C., and the mixture was reacted for 18 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (hexanoyloxy)methyl 3-formyl-1H-indole-1-carboxylate (Compound 1) (570 mg, yield: 53.6%).

The characteristic data of Compound 1 was: 1H NMR (400 MHz, DMSO): δ 9.98 (s, 1H), 8.43 (s, 1H), 8.12 (d, J=7.7 Hz, 1H), 7.70 (d, J=8.1 Hz, 1H), 7.34 (dtd, J=14.9, 7.6, 1.1 Hz, 2H), 6.31 (s, 2H), 2.32 (t, J=7.3 Hz, 2H), 1.54-1.40 (m, 2H), 1.23-1.05 (m, 4H), 0.75 (t, J=7.0 Hz, 3H).

The purity of compound 1 detected by HPLC was 98.71% at 254 nm and 98.70% at 214 nm, measured according to the normalization method of peak area.

Embodiment 2

Preparation of (hexanoyloxy)methyl 3-(hydroxymethyl)-1H-indole-carboxylate (Compound 19)

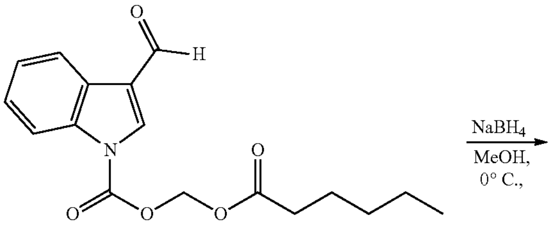

Compound 1

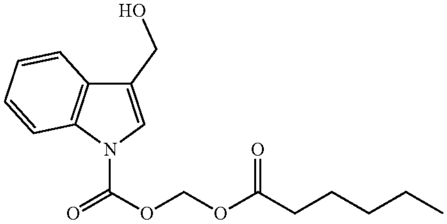

Compound 19

(hexanoyloxy)methyl 3-formyl-1H-indole-1-carboxylate (Compound 1)(240 mg, 0.76 mmol) was dissolved in anhydrous methanol (8 mL). After the temperature was decreased to 0° C., sodium borohydride (28.8 mg, 0.76 mmol) was added, and the mixture was reacted for 2 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (hexanoyloxy)methyl 3-(hydroxymethyl)-1H-indole-1-carboxylate (Compound 19) (200 mg, yield: 82.9%).

The characteristic data of Compound 19 was: 1H NMR (400 MHz, DMSO): δ 7.61 (d, J=7.8 Hz, 1H), 7.54 (d, J=8.2 Hz, 1H), 7.34 (s, 1H), 7.24-7.16 (m, 1H), 7.13-7.04 (m, 1H), 6.17 (s, 2H), 4.91 (t, J=5.4 Hz, 1H), 4.62 (d, J=5.2 Hz, 2H), 2.26 (t, J=7.3 Hz, 2H), 1.52-1.41 (m, 2H), 1.30-1.08 (m, 4H), 0.78 (t, J=7.0 Hz, 3H).

The purity of Compound 19 detected by HPLC was 96.18% at 254 nm and 96.51% at 214 nm, measured according to the normalization method of peak area.

Embodiment 3

Preparation of (octanoyloxy)methyl 3-formyl-1H-indole-1-carboxylate (Compound 2)

(1) the Compound B was Prepared According to the Method of Embodiment 1

(2) Synthesis of (octanoyloxy)methyl 3-formyl-1H-indole-1-carboxylate (Compound 2)

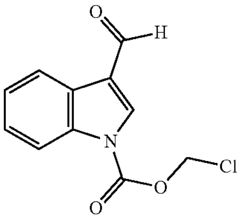

Compound B

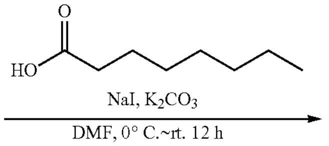

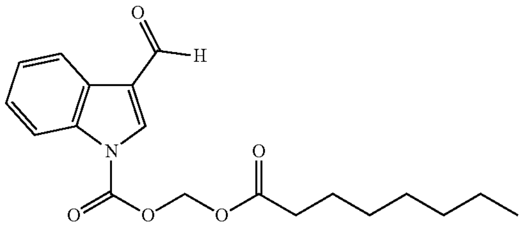

Compound 2

Sodium iodide (504 mg, 3.37 mmol) and potassium carbonate (1.4 g, 10.11 mmol) were added to a solution of chloromethyl 3-formyl-1H-indole-1-carboxylate (Compound B) (800 mg, 3.37 mmol) and octanoic acid (583.2 mg, 4.05 mmol) dissolved in anhydrous DMF (8.0 ml) at 0° C., and the mixture was reacted for 18 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently, the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (octanoyloxy)methyl 3-formyl-1H-indole-1-carboxylate (Compound 2) (480 mg, yield: 41.3%).

The characteristic data of Compound 2 was: 1H NMR (400 MHz, DMSO) δ 9.97 (s, 1H), 8.42 (s, 1H), 8.11 (d, J=7.7 Hz, 1H), 7.70 (d, J=8.1 Hz, 1H), 7.44-7.26 (m, 2H), 6.30 (s, 2H), 2.32 (t, J=7.2 Hz, 2H), 1.50-1.41 (m, 2H), 1.11 (s, 8H), 0.80 (t, J=7.0 Hz, 3H).

The purity of Compound 2 detected by HPLC was 99.42% at 254 nm and 98.47% at 214 nm, measured according to the normalization method of peak area.

Embodiment 4

Preparation of (octanoyloxy)methyl 3-(hydroxymethyl)-1H-indole-1-carboxylate (Compound 20)

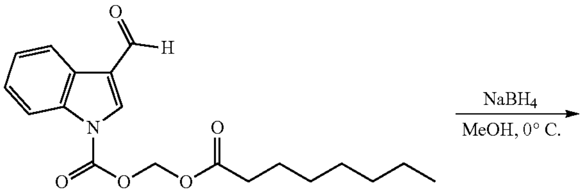

Compound 2

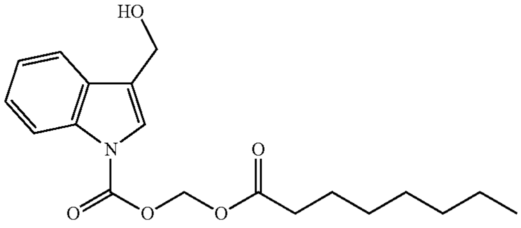

Compound 20

(octanoyloxy)methyl 3-formyl-1H-indole-1-carboxylate (Compound 2)(240 mg, 0.76 mmol) was dissolved in anhydrous methanol (8 ml). After the temperature was decreased to 0° C., sodium borohydride (28.8 mg, 0.76 mmol) was added, and the mixture was reacted for 2 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (octanoyloxy)methyl-3-(hydroxymethyl)-1H-indole-1-carboxylate (Compound 20) (150 mg, yield: 57%).

The characteristic data of Compound 20 was: 1H NMR (400 MHz, DMSO) δ 7.61 (d, J=7.8 Hz, 1H), 7.53 (d, J=8.2 Hz, 1H), 7.34 (s, 1H), 7.19 (t, J=7.1 Hz, 1H), 7.09 (t, J=7.0 Hz, 1H), 6.17 (s, 2H), 4.90 (t, J=5.4 Hz, 1H), 4.62 (d, J=5.4 Hz, 2H), 2.26 (t, J=7.3 Hz, 2H), 1.47 (d, J=6.9 Hz, 2H), 1.22 (d, J=10.1 Hz, 2H), 1.16 (s, 7H), 0.82 (t, J=7.0 Hz, 3H).

The purity of Compound 20 detected by HPLC was 95.69% at 254 nm and 95.81% at 214 nm, measured according to the normalization method of peak area.

Embodiment 5

Preparation of (decanoyloxy)methyl 3-formyl-1H-indole-1-carboxylate (Compound 3)

(1) The Compound B was Prepared According to the Method of Embodiment 1

(2) Synthesis of (decanoyloxy)methyl 3-formyl-1H-indole-1-carboxylate (Compound 3)

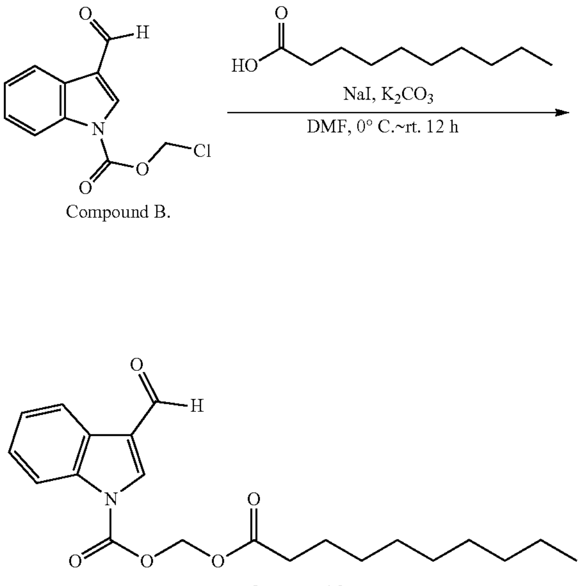

Compound B.

Compound 3

Sodium iodide (442 mg, 2.95 mmol) and potassium carbonate (1.2 g, 8.85 mmol) were added to a solution of chloromethyl 3-formyl-1H-indole-1-carboxylate (Compound B) (700 mg, 2.95 mmol) and decanoic acid (560 mg, 3.24 mmol) dissolved in anhydrous DMF (8.0 ml) at 0° C., and the mixture was reacted for 18 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (decanoyloxy)methyl 3-formyl-1H-indole-1-carboxylate (500 mg, yield: 50%).

The characteristic data of Compound 3 was: 1H NMR (400 MHz, DMSO) δ 9.97 (s, 1H), 8.42 (s, 1H), 8.11 (d, J=7.8 Hz, 1H), 7.70 (d, J=8.1 Hz, 1H), 7.34 (dt, J=25.0, 7.2 Hz, 2H), 6.30 (s, 2H), 2.31 (t, J=7.2 Hz, 2H), 1.47 (d, J=6.6 Hz, 2H), 1.23 (d, J=6.0 Hz, 2H), 1.13 (d, J=12.2 Hz, 10H), 0.84 (t, J=7.0 Hz, 3H).

The purity of compound 3 detected by HPLC was 98.70% at 254 nm and 98.85% at 214 nm, measured according to the normalization method of peak area.

Embodiment 6

Preparation of (decanoyloxy)methyl 3-(hydroxymethyl)-1H-indole-1-carboxylate (Compound 21)

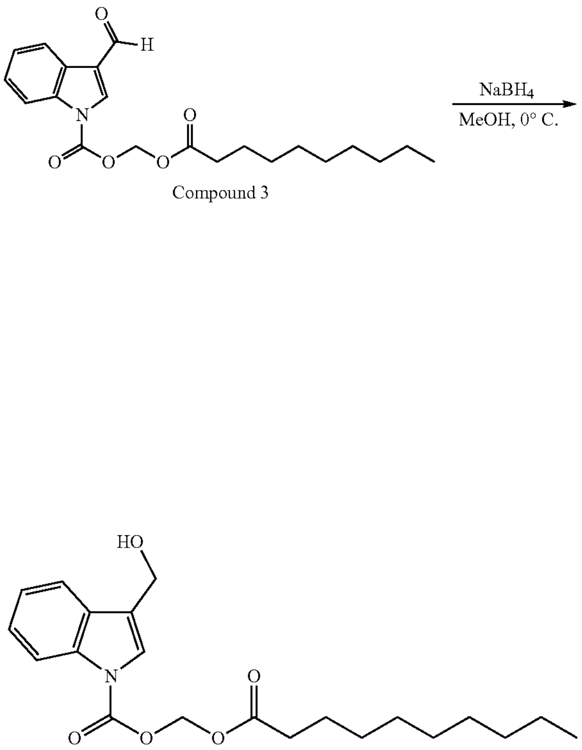

Compound 3

Compound 21

(decanoyloxy)methyl 3-formyl-1H-indole-1-carboxylate (Compound 3) (300 mg, 0.803 mmol) was dissolved in anhydrous methanol (8 ml). After the temperature was decreased to 0° C., sodium borohydride (31 mg, 0.803 mmol) was added, and the mixture was reacted for 2 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether:ethyl acetate=100:1 to 1:1), to obtain a white solid product, i.e. a desirable compound, (decanoyloxy)methyl 3-(hydroxymethyl)-1H-indole-1-carboxylate (Compound 21) (200 mg, yield: 66.5%).

The characteristic data of Compound 21 was: 1H NMR (400 MHz, DMSO) δ 7.61 (d, J=7.8 Hz, 1H), 7.53 (d, J=8.2 Hz, 1H), 7.34 (s, 1H), 7.19 (t, J=7.2 Hz, 1H), 7.09 (t, J=7.4 Hz, 1H), 6.17 (s, 2H), 4.90 (t, J=5.4 Hz, 1H), 4.61 (d, J=5.2 Hz, 2H), 2.26 (t, J=7.3 Hz, 2H), 1.52-1.38 (m, 2H), 1.20 (d, J=31.1 Hz, 12H), 0.85 (t, J=6.9 Hz, 3H).

The purity of Compound 21 detected by HPLC was 97.36% at 254 nm and 97.56% at 214 nm, measured according to the normalization method of peak area.

Embodiment 7

Preparation of (dodecanoyloxy)methyl 3-formyl-1H-indole-1-carboxylate (Compound 4)

(1) The Compound B was Prepared According to the Method of Embodiment 1

(2) Synthesis of (dodecanoyloxy)methyl 3-formyl-1H-indole-1-carboxylate (Compound 4)

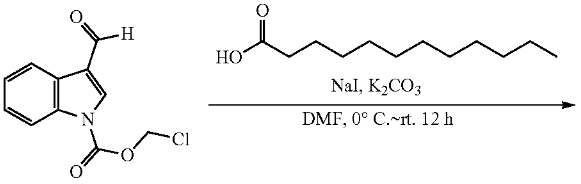

Compound B

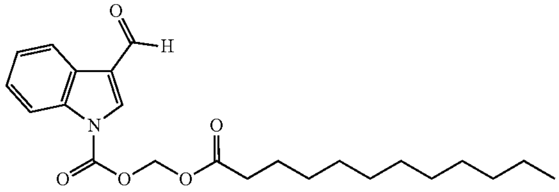

Compound 4

Sodium iodide (504 mg, 3.37 mmol) and potassium carbonate (1.4 g, 10.11 mmol) were added to a solution of chloromethyl 3-formyl-1H-indole-1-carboxylate (Compound B) (800 mg, 3.36 mmol) and dodecanoic acid (800 mg, 4.03 mmol) dissolved in anhydrous DMF (8.0 ml) at 0° C., and the mixture was reacted for 18 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently, the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow solid product, i.e. a desirable compound, (dodecanoyloxy)methyl 3-formyl-1H-indole-1-carboxylate (Compound 4) (500 mg, yield: 37%).

The characteristic data of Compound 4 was: 1H NMR (400 MHz, DMSO) δ 9.97 (s, 1H), 8.42 (s, 1H), 8.11 (d, J=7.7 Hz, 1H), 7.70 (d, J=8.3 Hz, 1H), 7.34 (dd, J=17.5, 7.4 Hz, 2H), 6.30 (s, 2H), 2.31 (t, J=7.2 Hz, 2H), 1.46 (s, 2H), 1.27-1.05 (m, 17H), 0.85 (t, J=6.9 Hz, 3H).

The purity of Compound 4 detected by HPLC was 98.06% at 254 nm and 96.38% at 214 nm, measured according to the normalization method of peak area.

The Compound 4 was recrystallized to obtain a pure crystal I of Compound 4. The pure compound was detected by X-ray powder diffraction (XRPD), and the results were showed in the following Table 1 and FIG. 1.

TABLE 1

XRPD data of crystal I of Compound 4

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 4.926 | 17.9251 | 176 | 24809 | 100.0 | 149171 | 100.0 | 0.100 |
| 2 | 7.268 | 12.1522 | 97 | 2750 | 11.1 | 21405 | 14.3 | 0.129 |
| 3 | 9.465 | 9.3362 | 89 | 72 | 0.3 | 771 | 0.5 | 0.177 |
| 4 | 9.893 | 8.9332 | 87 | 5899 | 23.8 | 33998 | 22.8 | 0.095 |
| 5 | 10.717 | 8.2480 | 96 | 189 | 0.8 | 1192 | 0.8 | 0.104 |
| 6 | 11.259 | 7.8524 | 83 | 743 | 3.0 | 6179 | 4.1 | 0.138 |
| 7 | 11.807 | 7.4890 | 85 | 449 | 1.8 | 3716 | 2.5 | 0.137 |
| 8 | 12.915 | 6.8492 | 71 | 59 | 0.2 | 303 | 0.2 | 0.085 |
| 9 | 13.365 | 6.6193 | 65 | 178 | 0.7 | 1277 | 0.9 | 0.119 |
| 10 | 14.612 | 6.0572 | 76 | 541 | 2.2 | 7785 | 5.2 | 0.238 |
| 11 | 14.881 | 5.9482 | 78 | 1788 | 7.2 | 12396 | 8.3 | 0.115 |
| 12 | 15.836 | 5.5916 | 80 | 186 | 0.7 | 1299 | 0.9 | 0.116 |
| 13 | 16.325 | 5.4251 | 76 | 64 | 0.3 | 415 | 0.3 | 0.107 |
| 14 | 16.952 | 5.2261 | 77 | 174 | 0.7 | 2071 | 1.4 | 0.197 |
| 15 | 18.389 | 4.8206 | 96 | 272 | 1.1 | 2530 | 1.7 | 0.154 |
| 16 | 18.991 | 4.6691 | 99 | 907 | 3.7 | 7760 | 5.2 | 0.142 |
| 17 | 19.870 | 4.4646 | 119 | 655 | 2.6 | 4862 | 3.3 | 0.123 |
| 18 | 20.281 | 4.3750 | 132 | 155 | 0.6 | 1349 | 0.9 | 0.144 |
| 19 | 20.628 | 4.3022 | 132 | 68 | 0.3 | 988 | 0.7 | 0.241 |
| 20 | 21.604 | 4.1099 | 159 | 2009 | 8.1 | 20045 | 13.4 | 0.165 |
| 21 | 21.975 | 4.0415 | 131 | 3762 | 15.2 | 41144 | 27.6 | 0.181 |
| 22 | 25.263 | 3.5224 | 89 | 247 | 1.0 | 5239 | 3.5 | 0.351 |
| 23 | 25.579 | 3.4796 | 97 | 118 | 0.5 | 2977 | 2.0 | 0.418 |
| 24 | 25.849 | 3.4439 | 96 | 96 | 0.4 | 2462 | 1.7 | 0.425 |
| 25 | 26.826 | 3.3206 | 83 | 88 | 0.4 | 1005 | 0.7 | 0.189 |
| 26 | 27.371 | 3.2557 | 73 | 79 | 0.3 | 1399 | 0.9 | 0.293 |
| 27 | 29.883 | 2.9875 | 80 | 102 | 0.4 | 2456 | 1.6 | 0.399 |
| 28 | 32.026 | 2.7923 | 64 | 83 | 0.3 | 2046 | 1.4 | 0.408 |

Embodiment 8

Preparation of (dodecanoyloxy)methyl 3-(hydroxymethyl)-1H-indole-1-carboxylate (Compound 22)

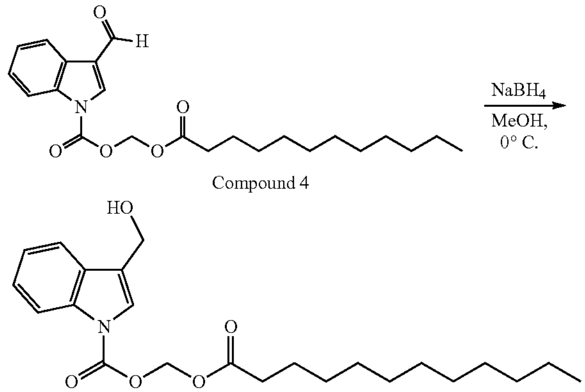

Compound 4

Compound 22

(dodecyloxy)methyl 3-formyl-1H-indole-1-carboxylate (Compound 4) (250 mg, 0.76 mmol) was dissolved in anhydrous methanol (8 ml). After the temperature was decreased to 0° C., sodium borohydride (28.8 mg, 0.76 mmol) was added, and the mixture was reacted for 2 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether:ethyl acetate=100:1 to 1:1), to obtain a yellow solid product, i.e. a desirable Compound 22, (dodecyloxy)methyl 3-(hydroxymethyl)-1H-indole-1-carboxylate (150 mg, yield: 57%).

The characteristic data of Compound 22 was 1H NMR (400 MHz, DMSO) δ 7.61 (d, J=7.7 Hz, 1H), 7.53 (d, J=8.2 Hz, 1H), 7.34 (s, 1H), 7.18 (dd, J=11.2, 4.1 Hz, 1H), 7.09 (t, J=7.0 Hz, 1H), 6.17 (s, 2H), 4.89 (t, J=5.4 Hz, 1H), 4.61 (d, J=5.1 Hz, 2H), 2.26 (t, J=7.3 Hz, 2H), 1.48-1.40 (m, 2H), 1.23 (d, J=7.9 Hz, 8H), 1.15 (s, 8H), 0.85 (t, J=6.9 Hz, 3H).

The purity of Compound 22 detected by HPLC was 98.63% at 254 nm and 98.21% at 214 nm, measured according to the normalization method of peak area.

Figure 2:
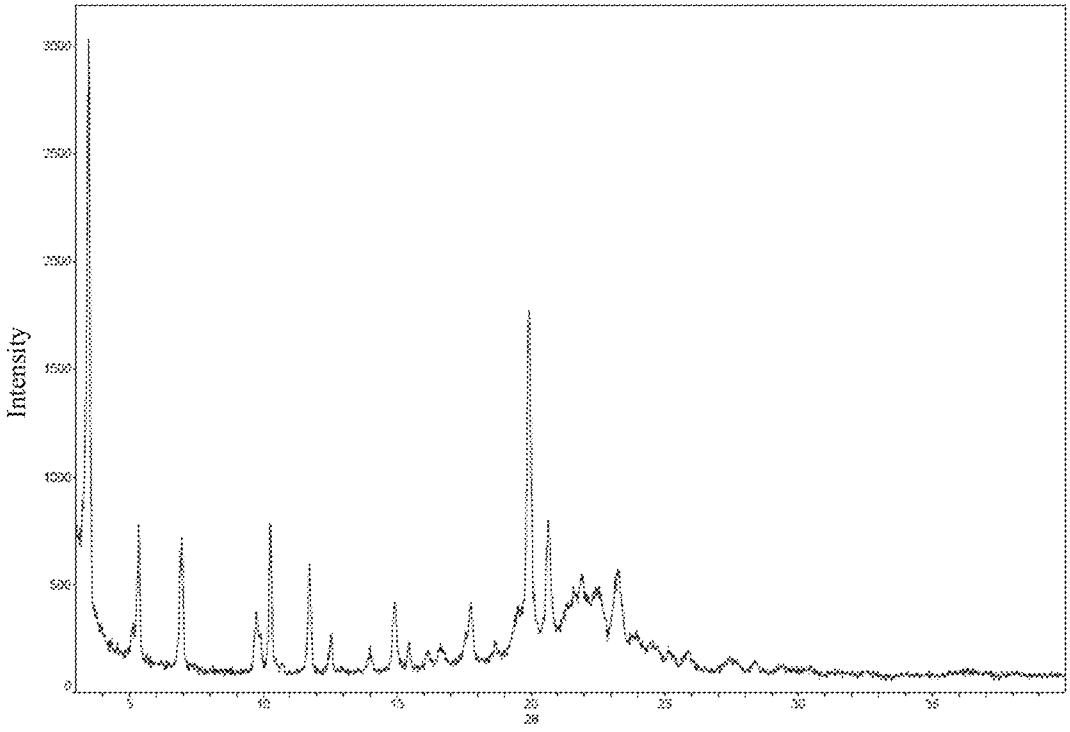
FIG. 2 depicts a XRPD pattern of Compound 22 in Embodiment 8.

The Compound 22 was recrystallized to obtain a pure crystal I of Compound 22. The pure compound was detected by X-ray powder diffraction (XRPD), and the results were showed in the following Table 2 and FIG. 2.

TABLE 2

XRPD data of crystal I of Compound 22

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 3.448 | 25.6041 | 198 | 2840 | 100.0 | 30796 | 100.0 | 0.180 |
| 2 | 5.318 | 16.6044 | 154 | 628 | 22.1 | 5259 | 17.1 | 0.139 |
| 3 | 6.915 | 12.7716 | 112 | 610 | 21.5 | 5066 | 16.5 | 0.138 |
| 4 | 9.736 | 9.0767 | 102 | 271 | 9.5 | 3294 | 10.7 | 0.201 |
| 5 | 10.231 | 8.6385 | 90 | 692 | 24.4 | 6014 | 19.5 | 0.144 |
| 6 | 11.706 | 7.5534 | 90 | 502 | 17.7 | 3824 | 12.4 | 0.126 |
| 7 | 12.505 | 7.0726 | 90 | 190 | 6.7 | 1596 | 5.2 | 0.139 |
| 8 | 13.969 | 6.3346 | 96 | 120 | 4.2 | 977 | 3.2 | 0.135 |
| 9 | 14.900 | 5.9406 | 104 | 312 | 11.0 | 3363 | 10.9 | 0.178 |
| 10 | 15.424 | 5.7400 | 109 | 132 | 4.6 | 1010 | 3.3 | 0.127 |
| 11 | 16.155 | 5.4819 | 130 | 64 | 2.3 | 356 | 1.2 | 0.092 |
| 12 | 16.598 | 5.3365 | 128 | 94 | 3.3 | 1220 | 4.0 | 0.215 |
| 13 | 17.744 | 4.9945 | 141 | 271 | 9.5 | 3784 | 12.3 | 0.231 |
| 14 | 18.641 | 4.7562 | 162 | 70 | 2.5 | 538 | 1.7 | 0.127 |
| 15 | 19.482 | 4.5527 | 221 | 181 | 6.4 | 4102 | 13.3 | 0.375 |
| 16 | 19.908 | 4.4561 | 256 | 1521 | 53.6 | 19075 | 61.9 | 0.208 |
| 17 | 20.629 | 4.3020 | 295 | 502 | 17.7 | 4826 | 15.7 | 0.159 |
| 18 | 21.895 | 4.0561 | 291 | 258 | 9.1 | 11879 | 38.6 | 0.762 |
| 19 | 22.538 | 3.9417 | 373 | 117 | 4.1 | 992 | 3.2 | 0.140 |
| 20 | 23.240 | 3.8242 | 255 | 318 | 11.2 | 5978 | 19.4 | 0.311 |
| 21 | 25.850 | 3.4437 | 118 | 73 | 2.6 | 1112 | 3.6 | 0.252 |

Detection condition: SCAN: 3.0001/39.9937/0.01948/16(sec), Cu, I(max) = 3038.

PEAK: 19-pts/Parabolic Filter, Threshold = 3.0, Cutoff = 0.1%, BG = 3/1.0, Peak-Top = Summit.

NOTE:

Intensity = Counts, 2T(0) = 0.0(deg), Wavelength to Compute d-Spacing = 1.54056 Å (Cu/K-alpha1).

Embodiment 9

Preparation of (tetradecanoyloxy)methyl 3-formyl-1H-indole-1-carboxylate (Compound 5)

(1) the Compound B was Prepared According to the Method of Embodiment 1

(2) Synthesis of (tetradecanoyloxy)methyl 3-formyl-1H-indole-1-carboxylate

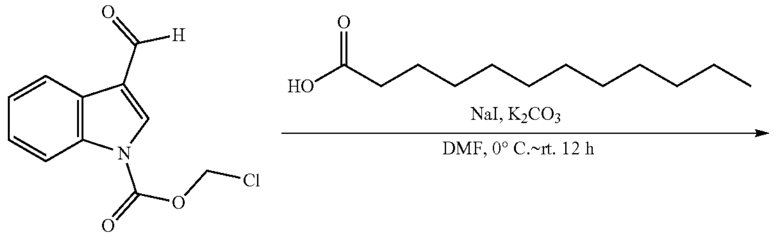

Compound B

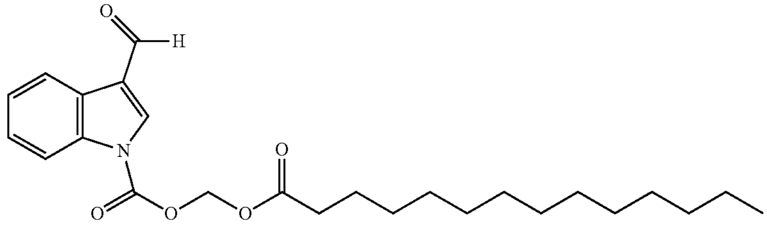

Compound 5

Sodium iodide (442 mg, 2.95 mmol) and potassium carbonate (1.2 g, 8.85 mmol) were added to a solution of chloromethyl 3-formyl-1H-indole-1-carboxylate (2) (700 mg, 2.95 mmol) and tetradecanoic acid (738 mg, 3.24 mmol) dissolved in anhydrous DMF (8.0 ml) at 0° C., and the mixture was reacted for 18 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently, the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e. a desirable compound, (tetradecanoyloxy)methyl 3-formyl-1H-indole-1-carboxylate (Compound 5) (500 mg, yield: 39.7%).

The characteristic data of Compound 5 was: 1H NMR (400 MHz, DMSO) δ 9.97 (s, 1H), 8.42 (s, 1H), 8.11 (d, J=7.7 Hz, 1H), 7.69 (d, J=8.1 Hz, 1H), 7.46-7.22 (m, 2H), 6.30 (s, 2H), 2.31 (t, J=7.2 Hz, 2H), 1.53-1.37 (m, 2H), 1.27-1.17 (m, 12H), 1.11 (s, 8H), 0.85 (t, J=6.8 Hz, 3H).

The purity of Compound 5 detected by HPLC was 99.76% at 254 nm and 99.69% at 214 nm, measured according to the normalization method of peak area.

Embodiment 10

Preparation of (tetradecanoyloxy)methyl 3-(hydroxymethyl)-1H-indole-1-carboxylate (Compound 23)

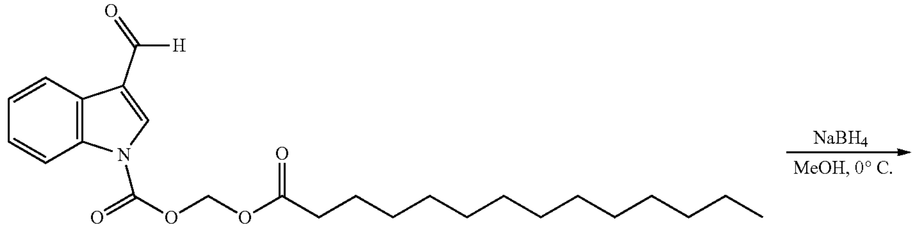

Compound 5

-continued

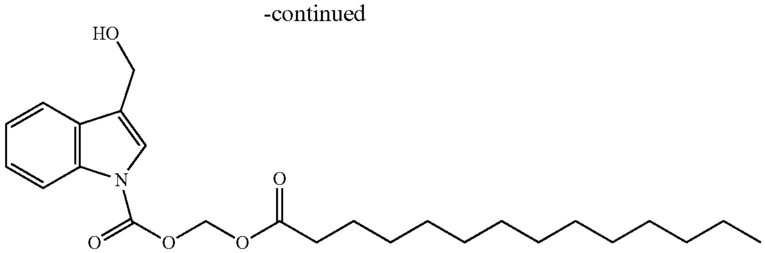

Compound 23

(tetradecanoyloxy)methyl 3-formyl-1H-indole-1-carboxylate (Compound 5) (250 mg, 0.58 mmol) was dissolved in anhydrous methanol/tetrahydrofuran (5 ml/5 ml). After the temperature was decreased to 0° C., sodium borohydride (22 mg, 0.58 mmol) was added, and the mixture was reacted for 1 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through chromatographic column (eluent:petroleum ether:ethyl acetate=100:1 to 1:1), to obtain a white solid product, i.e. a desirable compound, (tetradecanoyloxy)methyl 3-(hydroxymethyl)-1H-indole-1-carboxylate (Compound 23) (200 mg, yield: 80%).

The characteristic data of Compound 23 was: 1H NMR (400 MHz, DMSO) δ 7.60 (dd, J=7.6, 3.7 Hz, 1H), 7.53 (dd, J=8.2, 3.8 Hz, 1H), 7.33 (d, J=3.8 Hz, 1H), 7.19 (t, J=7.5 Hz, 1H), 7.09 (td, J=7.3, 3.5 Hz, 1H), 6.16 (d, J=3.9 Hz, 2H), 4.89 (dd, J=10.0, 5.2 Hz, 1H), 4.68-04.55 (m, 2H), 2.25 (td, J=7.2, 3.8 Hz, 2H), 1.45 (s, 2H), 1.23 (s, 12H), 1.15 (s, 8H), 0.93-0.78 (in, 3H).

The purity of Compound 23 detected by HPLC was 98.71% at 254 nm and 98.03% at 214 nm, measured according to the normalization method of peak area.

Figure 3:
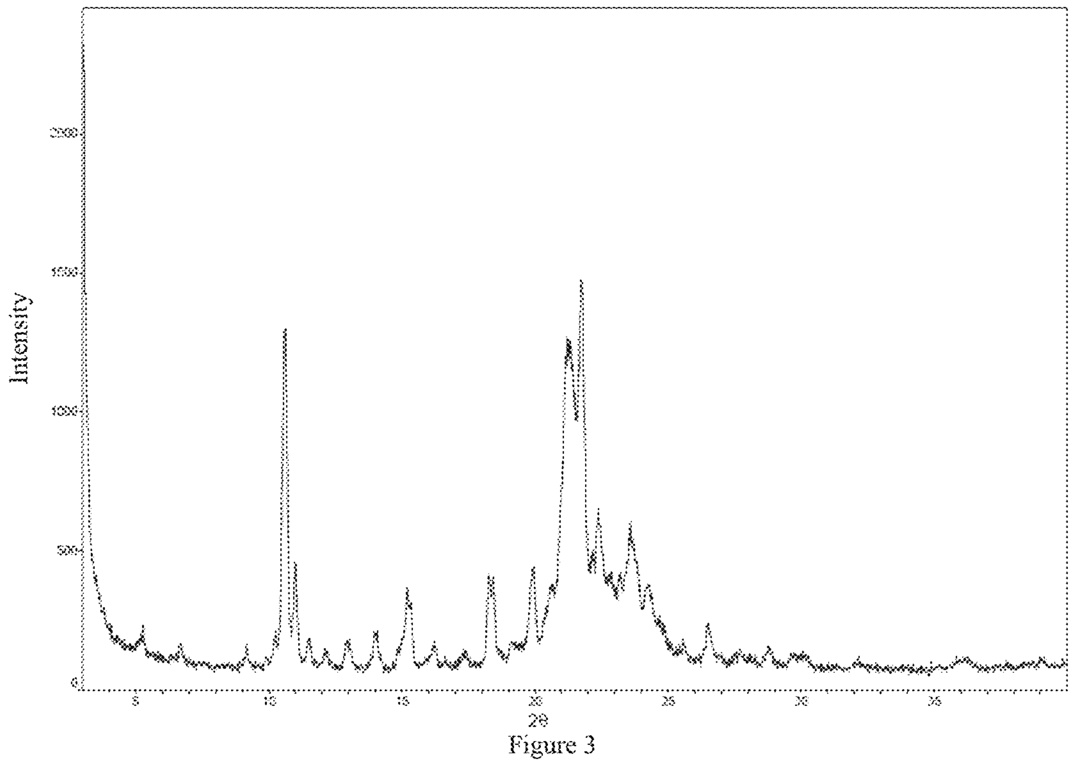
FIG. 3 depicts a XRPD pattern of Compound 23 in Embodiment 10.

The Compound 23 was recrystallized to obtain a pure crystal I of Compound 23. The pure compound was detected by X-ray powder diffraction (XRPD), and the results were showed in the following Table 3 and FIG. 3.

TABLE 3

XRPD data of crystal I of Compound 23

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 5.240 | 16.8514 | 135 | 97 | 8.1 | 558 | 1.4 | 0.095 |
| 2 | 6.660 | 13.2606 | 97 | 65 | 5.4 | 751 | 1.9 | 0.191 |
| 3 | 9.141 | 9.6662 | 82 | 82 | 6.8 | 478 | 1.2 | 0.097 |
| 4 | 10.226 | 8.6431 | 90 | 117 | 9.8 | 1770 | 4.5 | 0.251 |
| 5 | 10.595 | 8.3428 | 96 | 1199 | 100.0 | 16128 | 40.8 | 0.223 |
| 6 | 10.969 | 8.0595 | 90 | 365 | 30.4 | 4632 | 11.7 | 0.210 |
| 7 | 11.509 | 7.6822 | 98 | 86 | 7.2 | 605 | 1.5 | 0.116 |
| 8 | 12.098 | 7.3099 | 82 | 59 | 4.9 | 595 | 1.5 | 0.167 |
| 9 | 12.994 | 6.8073 | 75 | 103 | 8.6 | 1384 | 3.5 | 0.222 |
| 10 | 13.952 | 6.3422 | 73 | 131 | 10.9 | 1701 | 4.3 | 0.215 |
| 11 | 15.193 | 5.8269 | 81 | 286 | 23.9 | 4763 | 12.0 | 0.276 |
| 12 | 16.189 | 5.4705 | 81 | 91 | 7.6 | 1364 | 3.4 | 0.248 |
| 13 | 17.394 | 5.0942 | 82 | 58 | 4.8 | 723 | 1.8 | 0.206 |
| 14 | 18.373 | 4.8248 | 98 | 290 | 24.2 | 5007 | 12.7 | 0.286 |
| 15 | 19.179 | 4.6238 | 133 | 41 | 3.4 | 449 | 1.1 | 0.181 |
| 16 | 19.926 | 4.4522 | 165 | 275 | 22.9 | 4122 | 10.4 | 0.248 |
| 17 | 20.571 | 4.3141 | 158 | 216 | 18.0 | 3793 | 9.6 | 0.291 |
| 18 | 21.196 | 4.1882 | 201 | 1070 | 89.2 | 39537 | 100.0 | 0.612 |
| 19 | 21.721 | 4.0882 | 371 | 1107 | 92.3 | 30846 | 78.0 | 0.461 |
| 20 | 22.364 | 3.9720 | 462 | 184 | 15.3 | 1003 | 2.5 | 0.090 |
| 21 | 23.181 | 3.8338 | 356 | 65 | 5.4 | 937 | 2.4 | 0.239 |
| 22 | 23.570 | 3.7714 | 320 | 282 | 23.5 | 6750 | 17.1 | 0.396 |
| 23 | 24.234 | 3.6697 | 127 | 249 | 20.8 | 7070 | 17.9 | 0.470 |
| 24 | 26.511 | 3.3594 | 104 | 132 | 11.0 | 1842 | 4.7 | 0.231 |
| 25 | 27.695 | 3.2183 | 94 | 44 | 3.7 | 722 | 1.8 | 0.272 |
| 26 | 28.776 | 3.0999 | 92 | 63 | 5.3 | 601 | 1.5 | 0.158 |

Embodiment 11

Preparation of (palmitoyloxy)methyl 3-formyl-1H-indole-1-carboxylate (Compound 6)

(1) The Compound B was Prepared According to the Method of Embodiment 1

(2) Synthesis of iodomethyl 3-formyl-1H-indole-1-carboxylate (Compound C)

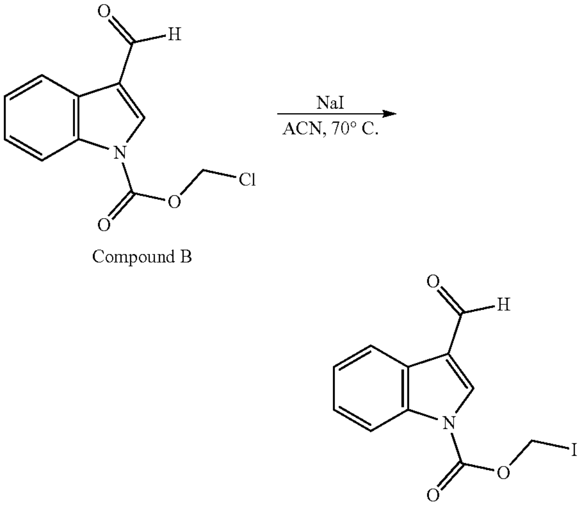

Compound B

Compound C

Chloromethyl 3-formyl-1H-indole-1-carboxylate (Compound B) (2.3 g, 9.66 mmol) and sodium iodide (4.3 g. 29.2 mmol) were dissolved in acetonitrile (20 mL). After the temperature was increased to 70° C., the mixture was reacted for 4 hours. TLC (petroleum ether:ethyl acetate=5:1) showed that the reaction was completed. The reaction liquid was filtered, and the filtrate was extracted by ethyl acetate. Subsequently, the liquid was concentrated to obtain iodomethyl 3-formyl-1H-indole-1-carboxylate (Compound C) (2.4 g, yield: 77%).

(3) Synthesis of Silver Palmitate (Compound C-2)

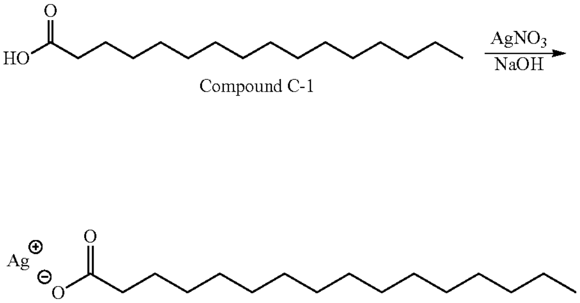

Compound C-1

Compound C-2

Palmitic acid (Compound C-1) (2 g, 7.8 mmol) was dissolved in a sodium hydroxide solution (312 mg/40 mL). After the temperature was increased to 80° C., silver nitrate (1.32 g, 7.8 mmol) was added to the mixture to precipitate a white solid. Subsequently, the mixture was cooled to room temperature, filtered, and the filter cake was washed by water, and dried to obtain a silver palmitate (Compound C-2) (2.5 g, yield: 89%).

(4) Synthesis of (palmitoyloxy)methyl 3-formyl-1H-indole-1-carboxylate (Compound 6)

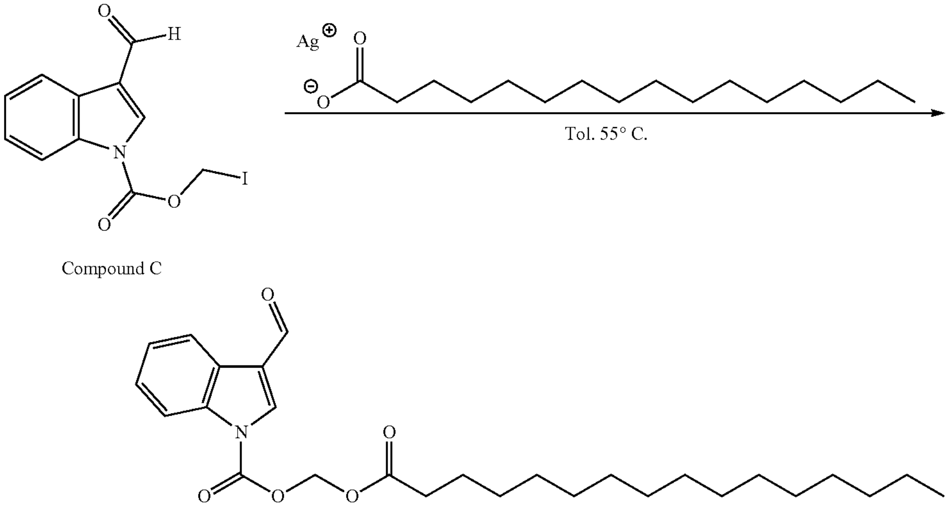

Compound C

Compound 6

Silver palmitate (2.1 g, 5.1 mmol) was added to a solution of iodomethyl 3-formyl-1H-indole-1-carboxylate (1.5 g, 4.6 mmol) dissolved in anhydrous methylbenzene (20 ml) at 0° C. After the temperature was increased to 55° C., the mixture was reacted for 4 hours. TLC (petroleum ether:ethyl acetate=3:1) showed that the reaction was completed. The reaction liquid was filtered, and the filtrate was extracted by ethyl acetate (3×50 mL). Subsequently, the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a white solid product, i.e. a desirable Compound, (palmitoyloxy)methyl 3-formyl-1H-indole-1-carboxylate (Compound 6) (800 mg, yield: 38%).

The characteristic data of Compound 6 was: 1H NMR (400 MHz, DMSO) δ 7.60 (dd, J=7.6, 3.7 Hz, 1H), 7.53 (dd, J=8.2, 3.8 Hz, 1H), 7.33 (d, J=3.8 Hz, 1H), 7.19 (t, J=7.5 Hz, 1H), 7.09 (td, J=7.3, 3.5 Hz, 1H), 6.16 (d, J=3.9 Hz, 2H), 4.89 (dd, J=10.0, 5.2 Hz, 1H), 4.68-4.55 (m, 2H), 2.25 (td, J=7.2, 3.8 Hz, 2H), 1.45 (s, 2H), 1.23 (s, 12H), 1.15 (s, 8H), 0.93-0.78 (m, 3H).

The purity of Compound 6 detected by HPLC was 99.03% at 254 nm and 97.54% at 214 nm, measured according to the normalization method of peak area.

Embodiment 12

Preparation of (palmitoyloxy)methyl 3-(hydroxymethyl)-1H-indole-1-carboxylate (Compound 24)

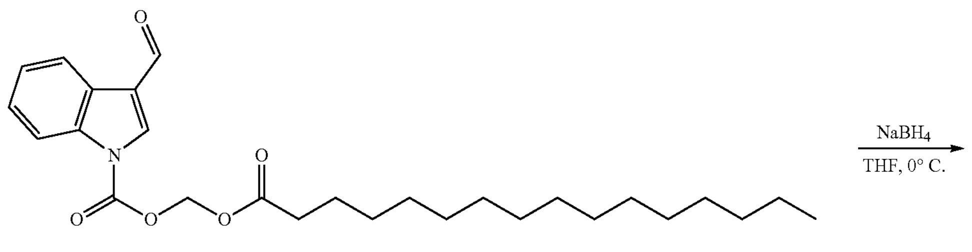

Compound 6

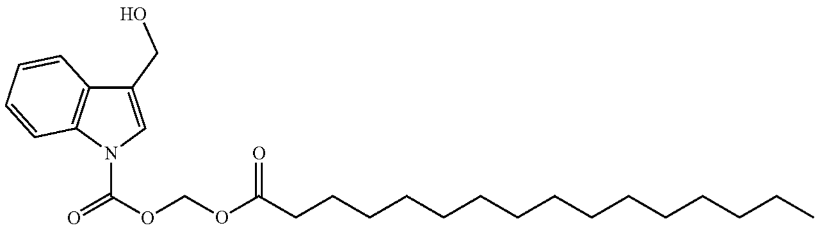

Compound 24

(palmitoyloxy)methyl 3-formyl-1H-indole-1-carboxylate (compound 6) (300 mg, 0.65 mmol) was dissolved in anhydrous tetrahydrofuran (8 mL). After the temperature was decreased to 0° C., sodium borohydride (25.8 mg, 0.65 mmol) was added, and the mixture was reacted for 2 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether:ethyl acetate=100:1 to 1:1), to obtain a white solid product, i.e. a desirable compound, (palmitoyloxy)methyl 3-(hydroxymethyl)-1H-indole-1-carboxylate (Compound 24) (150 mg, yield: 50%).

The characteristic data of Compound 24 was: 1H NMR (400 MHz, DMSO) δ 8.05 (d, J=7.8 Hz, 1H), 7.67 (d, J=7.7 Hz, 1H), 7.54 (s, 1H), 7.36 (dd, J=11.3, 4.2 Hz, 1H), 7.29 (t, J=7.5 Hz, 1H), 6.00 (s, 2H), 5.16 (t, J=5.5 Hz, 1H), 4.64 (dd, J=5.5, 1.0 Hz, 2H), 2.41 (t, J=7.2 Hz, 2H), 1.59-1.47 (m, 2H), 1.25 (d, J=16.2 Hz, 16H), 1.14 (s, 8H), 0.85 (t, J=6.8 Hz, 3H).

The purity of Compound 24 detected by HPLC was 97.66% at 254 nm and 98.28% at 214 nm, measured according to the normalization method of peak area.

Figure 4:
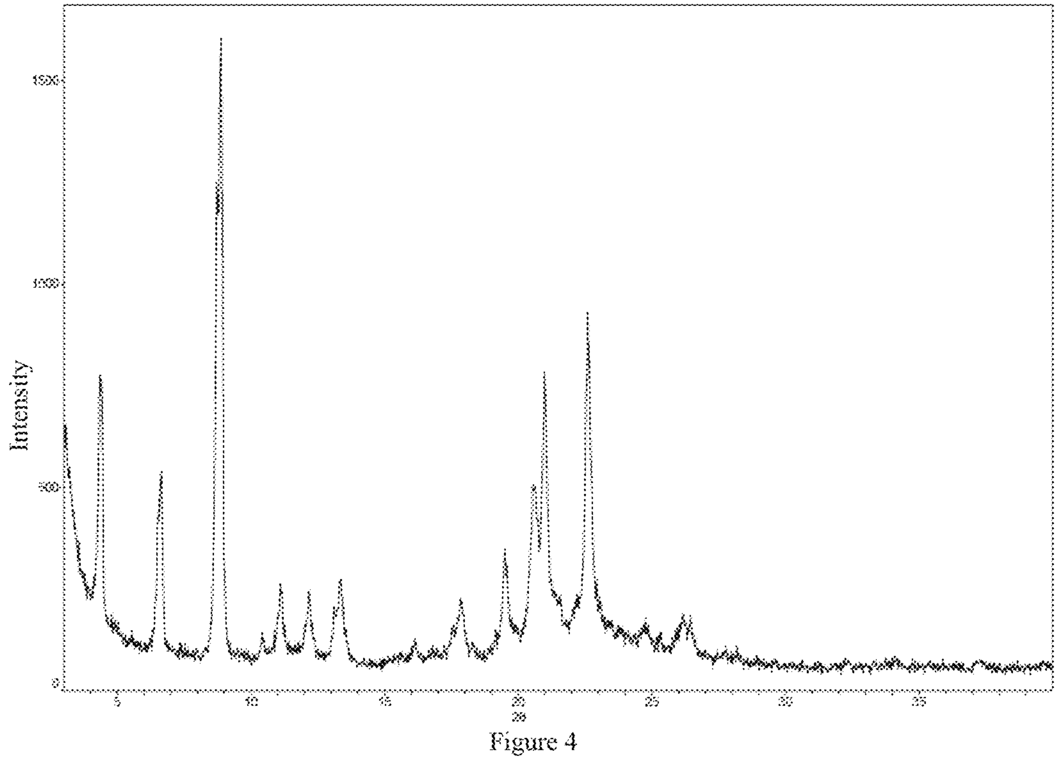
FIG. 4 depicts a XRPD pattern of Compound 24 in Embodiment 12.

The Compound 24 was recrystallized to obtain a pure crystal I of Compound 24. The pure compound was detected by X-ray powder diffraction (XRPD), and the results were showed in the following Table 4 and FIG. 4.

TABLE 4

| XRPD data of crystal I of Compound 24 | | | | | | | | |
|---|---|---|---|---|---|---|---|---|
| No. | 2θ | Interplanar distance (d) (Å) | Intensity of background signal (BG) | Peak Height | Relative peak Height % | Peak Area | Relative peak Area % | Full width at half maximum (FWHM) |
| 1 | 4.365 | 20.2251 | 120 | 655 | 43.1 | 10414 | 48.6 | 0.263 |
| 2 | 6.642 | 13.2967 | 101 | 440 | 28.9 | 5258 | 24.5 | 0.198 |
| 3 | 8.881 | 9.9484 | 86 | 1521 | 100.0 | 21423 | 100.0 | 0.233 |
| 4 | 10.420 | 8.4826 | 82 | 59 | 3.9 | 502 | 2.3 | 0.141 |
| 5 | 11.106 | 7.9605 | 92 | 176 | 11.6 | 2482 | 11.6 | 0.234 |
| 6 | 12.176 | 7.2628 | 90 | 158 | 10.4 | 1888 | 8.8 | 0.198 |
| 7 | 13.362 | 6.6209 | 74 | 198 | 13.0 | 3829 | 17.9 | 0.320 |
| 8 | 16.131 | 5.4901 | 78 | 48 | 3.2 | 348 | 1.6 | 0.120 |
| 9 | 17.847 | 4.9657 | 85 | 141 | 9.3 | 2921 | 13.6 | 0.343 |
| 10 | 19.501 | 4.5482 | 110 | 236 | 15.5 | 3547 | 16.6 | 0.249 |
| 11 | 20.611 | 4.3058 | 158 | 346 | 22.7 | 8858 | 41.3 | 0.424 |
| 12 | 20.982 | 4.2304 | 147 | 636 | 41.8 | 12277 | 57.3 | 0.320 |
| 13 | 22.599 | 3.9313 | 154 | 777 | 51.1 | 12114 | 56.5 | 0.258 |
| 14 | 24.756 | 3.5935 | 116 | 60 | 3.9 | 788 | 3.7 | 0.217 |
| 15 | 26.163 | 3.4033 | 95 | 92 | 6.0 | 2260 | 10.5 | 0.407 |
| 16 | 26.451 | 3.3668 | 87 | 96 | 6.3 | 2608 | 12.2 | 0.450 |

Embodiment 13

Preparation of esterized 3-oxo-2,5,8,11,14,17-hexaoxyoctanoyl-3-formyl-1H-indole-1-carboxylate (Compound 7)

(1) The Compound B was Prepared According to the Method of Embodiment 1

(2) Synthesis of Esterized 3-oxo-2,5,8,11,14,17-hexaoxyoctanoyl-3-formyl-1H-indole-1-carboxylate (Compound 7)

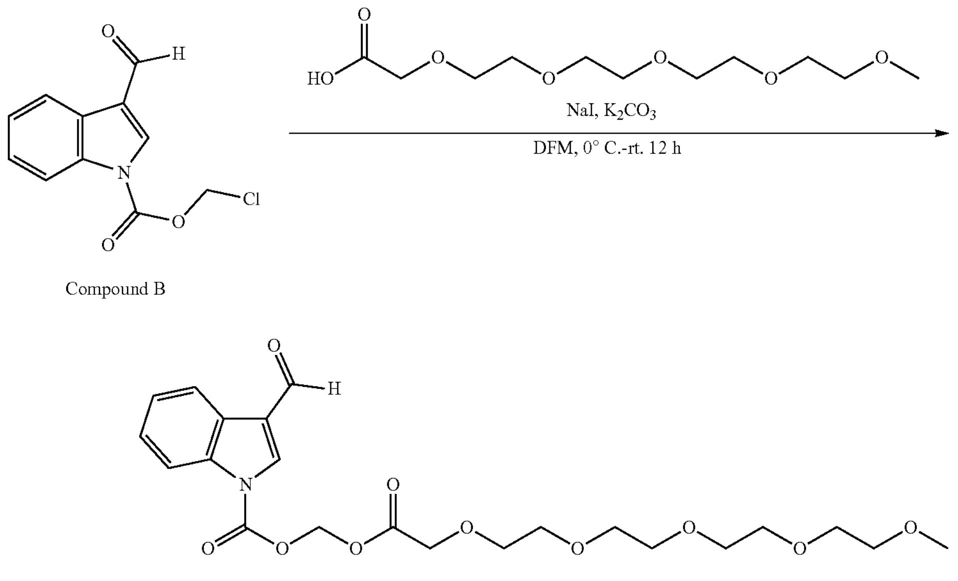

Compound B

Compound 7

Sodium iodide (1.1 g, 7.5 mmol) and potassium carbonate (3.1 g, 22.5 mmol) were added to a solution of chloromethyl 3-formyl-1H-indole-1-carboxylate (Compound B) (1.78 g, 7.5 mmol) and 2,5,8,11,14-pentaoxahexadecan-16-oic acid (2.0 g, 7.5 mmol) dissolved in anhydrous DMF (8.0 ml) at 0° C., and the mixture was reacted for 2 hours at room temperature. TLC (petroleum ether:ethyl acetate=3:1) showed that the reaction was completed. Water (50 ml) was added to the reaction liquid, and the liquid was extracted by ethyl acetate (3×40 mL). Subsequently, the organic phases were combined, washed by water (50 ml) and saturated saline (50 ml), dried by anhydrous sodium sulfate, filtered, concentrated under reduced pressure, and purified through a chromatographic column (eluent:petroleum ether:ethyl acetate=100:1 to 1:1), to obtain a yellow oily product, i.e., a desirable esterized compound, 3-oxo-2,5,8,11,14,17-hexaoxyoctanoyl-3-formyl-1H-indole-1-carboxylate (Compound 7) (600 mg, yield: 17.1%).

The characteristic data of Compound 7 was: 1H NMR (400 MHz, CDCl3) δ 10.04 (s, 1H), 8.36-8.25 (m, 1H), 7.95 (s, 1H), 7.54 (d, J=7.4 Hz, 1H), 7.38 (dq, J=7.2, 6.0 Hz, 2H), 6.20 (s, 2H), 4.18 (s, 2H), 3.68 (d, J=5.2 Hz, 2H), 3.66-3.56 (m, 12H), 3.53 (dd, J=5.7, 3.5 Hz, 2H), 3.36 (s, 3H).

The purity of Compound 7 detected by HPLC was 96.07% at 254 nm and 95.59% at 214 nm, measured according to the normalization method of peak area.

Embodiment 14

Preparation of ((2-acetoxybenzoyl)oxy)methyl 3-formyl-1H-indole-1-carboxylate (Compound 8)

(1) Synthesis of Silver 2-acetoxybenzoate (R8_Ag+)

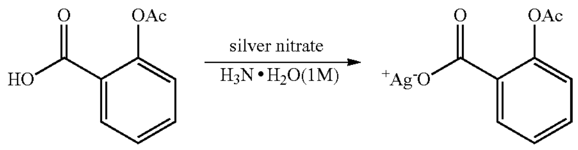

R8 R8_Ag+

2-acetoxybenzoic acid (Compound R8) (2.0 g, 11.1 mmol) was dissolved in 1M ammonia hydroxide solution (30 mL). After the temperature was cooled to 0° C., silver nitrate aqueous solution (1.89 g, 11.1 mmol, 10 mL) was added and the mixture was reacted for half an hour at 0° C. A great amount of white solid precipitated, and the mixture was filtered to gather the white solid product. The filter cake was washed by water, and the solid was dried to obtain silver 2-acetoxybenzoate (R8_Ag+) (2.5 g, yield: 78.6%).

(2) Synthesis of ((2-acetoxybenzoyl)oxy)methyl 3-formyl-1H-indole-1-carboxylate

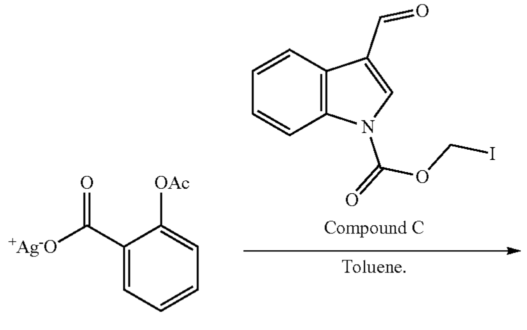

R8_Ag+

-continued

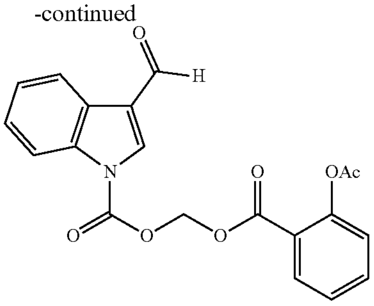

Compound 8

Silver 2-acetoxybenzoate (1.25 g, 4.35 mmol) and iodomethyl 3-formyl-1H-indole-1-carboxylate (Compound C) (1.0 g, 3.0 mmol) were added to methylbenzene (10 ml), and the mixture was reacted for 4 hours at 40° C. LCMS showed that iodomethyl 3-formyl-1H-indole-1-carboxylate was reacted completely. The reaction liquid was filtered, and the filtrate was extracted by ethyl acetate (3×20 mL) and water (40 mL). Subsequently, the organic phases were combined, washed by saturated saline (20 ml), dried by anhydrous sodium sulfate, filtered, concentrated under reduced pressure, and purified through a chromatographic column (eluent:petroleum ether:ethyl acetate=100:1 to 1:1), to obtain a light yellow solid product, i.e., a desirable compound, ((2-acetoxybenzoyl)oxy)methyl 3-formyl-1H-indole-1-carboxylate (Compound 8) (500 mg, yield: 43.7%).

The characteristic data of Compound 8 was: 1H NMR (400 MHz, DMSO) δ 10.11 (s, 1H), 8.75 (s, 1H), 8.17 (d, J=9.1 Hz, 2H), 8.05 (dd, J=7.9, 1.6 Hz, 1H), 7.80-7.70 (m, 1H), 7.47 (ddd, J=24.6, 16.8, 8.2 Hz, 3H), 7.29 (d, J=7.2 Hz, 1H), 6.28 (s, 2H), 2.27 (s, 3H).

The purity of Compound 8 detected by HPLC was 95.96% at 254 nm and 95.28% at 214 nm, measured according to the normalization method of peak area.

Figure 5:
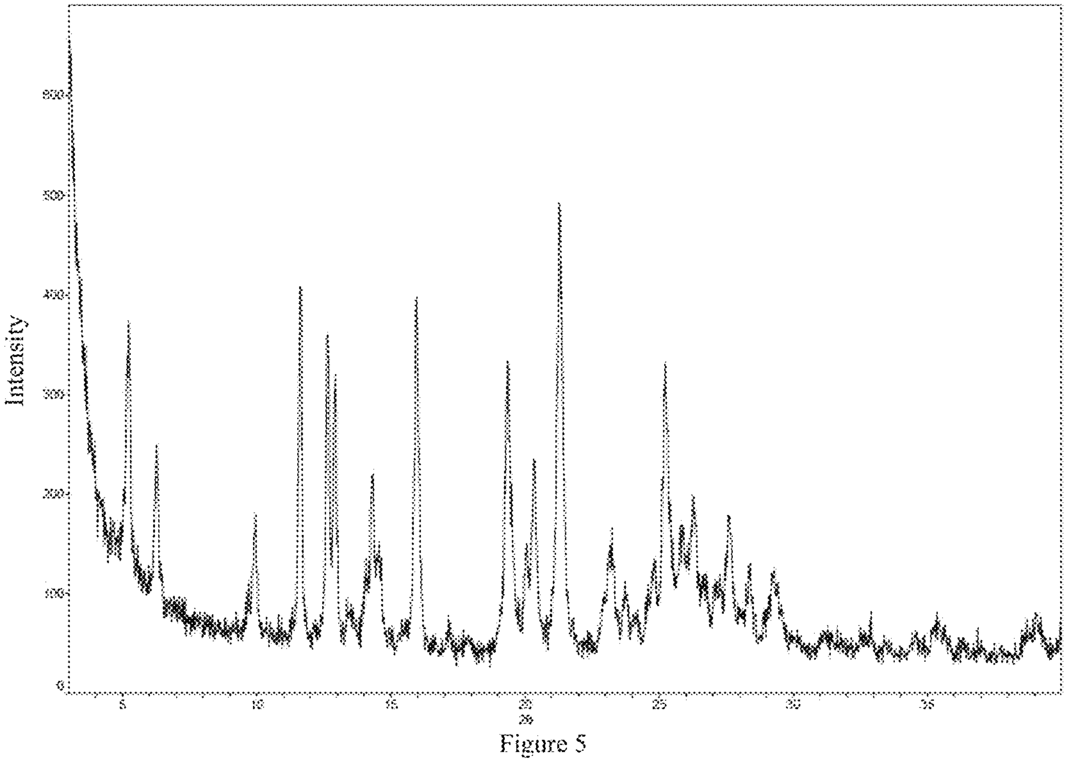
FIG. 5 depicts a XRPD pattern of Compound 8 in Embodiment 14.

The Compound 8 was recrystallized to obtain a pure crystal I of Compound 8. The pure compound was detected by X-ray powder diffraction (XRPD), and the results were showed in the following Table 5 and FIG. 5.

TABLE 5

XRPD data of crystal I of Compound 8

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 5.239 | 16.8540 | 129 | 244 | 56.2 | 2748 | 45.6 | 0.186 |
| 2 | 6.272 | 14.0805 | 101 | 149 | 34.3 | 1178 | 19.5 | 0.131 |
| 3 | 9.951 | 8.8815 | 60 | 121 | 27.9 | 1395 | 23.1 | 0.191 |
| 4 | 11.615 | 7.6128 | 57 | 354 | 81.6 | 2935 | 48.7 | 0.137 |
| 5 | 12.644 | 6.9952 | 58 | 304 | 70.0 | 3232 | 53.6 | 0.176 |
| 6 | 12.931 | 6.8405 | 61 | 259 | 59.7 | 2449 | 40.6 | 0.157 |
| 7 | 14.066 | 6.2911 | 64 | 72 | 16.6 | 898 | 14.9 | 0.207 |
| 8 | 14.334 | 6.1740 | 59 | 161 | 37.1 | 3079 | 51.1 | 0.317 |

TABLE 5-continued

| XRPD data of crystal I of Compound 8 | | | | | | | | |
|---|---|---|---|---|---|---|---|---|
| No. | 2θ | Interplanar distance (d) (Å) | Intensity of background signal (BG) | Peak Height | Relative peak Height % | Peak Area | Relative peak Area % | Full width at half maximum (FWHM) |
| 9 | 14.569 | 6.0750 | 55 | 96 | 22.1 | 1981 | 32.9 | 0.342 |
| 10 | 15.955 | 5.5500 | 45 | 354 | 81.6 | 4328 | 71.8 | 0.202 |
| 11 | 17.169 | 5.1605 | 43 | 34 | 7.8 | 232 | 3.8 | 0.113 |
| 12 | 19.345 | 4.5846 | 63 | 273 | 62.9 | 3591 | 59.6 | 0.218 |
| 13 | 20.062 | 4.4223 | 78 | 72 | 16.6 | 816 | 13.5 | 0.188 |
| 14 | 20.355 | 4.3592 | 72 | 163 | 37.6 | 2148 | 35.6 | 0.218 |
| 15 | 21.276 | 4.1727 | 58 | 434 | 100.0 | 6029 | 100.0 | 0.230 |
| 16 | 23.241 | 3.8241 | 61 | 105 | 24.2 | 1471 | 24.4 | 0.232 |
| 17 | 23.729 | 3.7465 | 56 | 58 | 13.4 | 1077 | 17.9 | 0.307 |
| 18 | 24.831 | 3.5827 | 91 | 44 | 10.1 | 449 | 7.4 | 0.169 |
| 19 | 25.227 | 3.5274 | 96 | 236 | 54.4 | 3530 | 58.6 | 0.248 |
| 20 | 25.874 | 3.4406 | 88 | 81 | 18.7 | 2579 | 42.8 | 0.527 |
| 21 | 26.262 | 3.3906 | 93 | 105 | 24.2 | 2478 | 41.1 | 0.391 |
| 22 | 27.120 | 3.2853 | 74 | 39 | 9.0 | 645 | 10.7 | 0.274 |
| 23 | 27.622 | 3.2268 | 69 | 109 | 25.1 | 2417 | 40.1 | 0.367 |
| 24 | 28.399 | 3.1401 | 72 | 58 | 13.4 | 447 | 7.4 | 0.128 |
| 25 | 29.296 | 3.0461 | 55 | 70 | 16.1 | 1395 | 23.1 | 0.330 |
| 26 | 39.075 | 2.3033 | 41 | 38 | 8.8 | 893 | 14.8 | 0.389 |

Embodiment 15

Preparation of ((2-acetoxybenzoyl)oxy)methyl 3-(hydroxymethyl)-1H-indole-1-carboxylate (Compound 26)

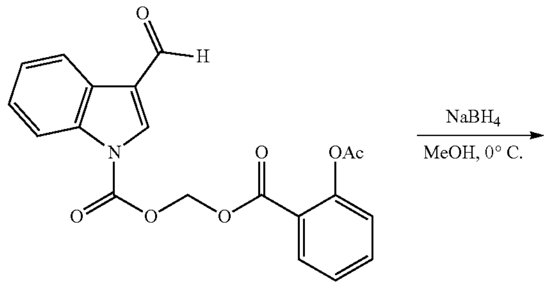

Compound 8

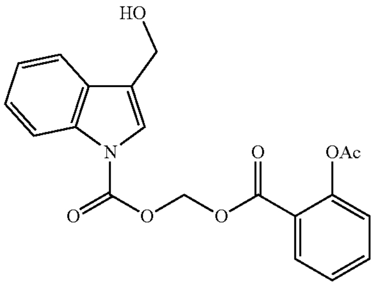

Compound 26

((2-acetoxybenzoyl)oxy)methyl 3-formyl-1H-indole-1-carboxylate (Compound 8) (170 mg, 0.446 mmol) was dissolved in anhydrous methanol/tetrahydrofuran (3 ml/3 ml). After the temperature was decreased to 0° C., sodium borohydride (17 mg, 0.446 mmol) was added, and the mixture was reacted for 3 hours at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 mL) and saturated saline (20 mL), dried by anhydrous sodium sulfate, filtered, concentrated under reduced pressure, and purified through a chromatographic column (eluent:petroleum ether:ethyl acetate=100:1 to 1:1), to obtain a light yellow solid product, i.e. a desirable compound, ((2-acetoxybenzoyl)oxy)methyl 3-(hydroxymethyl)-1H-indole-1-carboxylate (Compound 26) (110 mg, yield: 64.7%).

The characteristic data of Compound 26 was: 1H NMR (400 MHz, DMSO) δ 8.09 (d, J=8.4 Hz, 1H), 8.01 (dd, J=7.9, 1.6 Hz, 1H), 7.74 (td, J=7.8, 1.7 Hz, 1H), 7.68 (d, J=7.6 Hz, 1H), 7.58 (s, 1H), 7.44 (dd, J=11.0, 4.3 Hz, 1H), 7.39 (t, J=7.3 Hz, 1H), 7.33-7.23 (m, 2H), 6.22 (s, 2H), 5.16 (t, J=5.5 Hz, 1H), 4.69-4.59 (m, 2H), 2.26 (s, 3H).

The purity of Compound 26 detected by HPLC was 96.35% at 254 nm and 95.62% at 214 nm, measured according to the normalization method of peak area.

Figure 6:
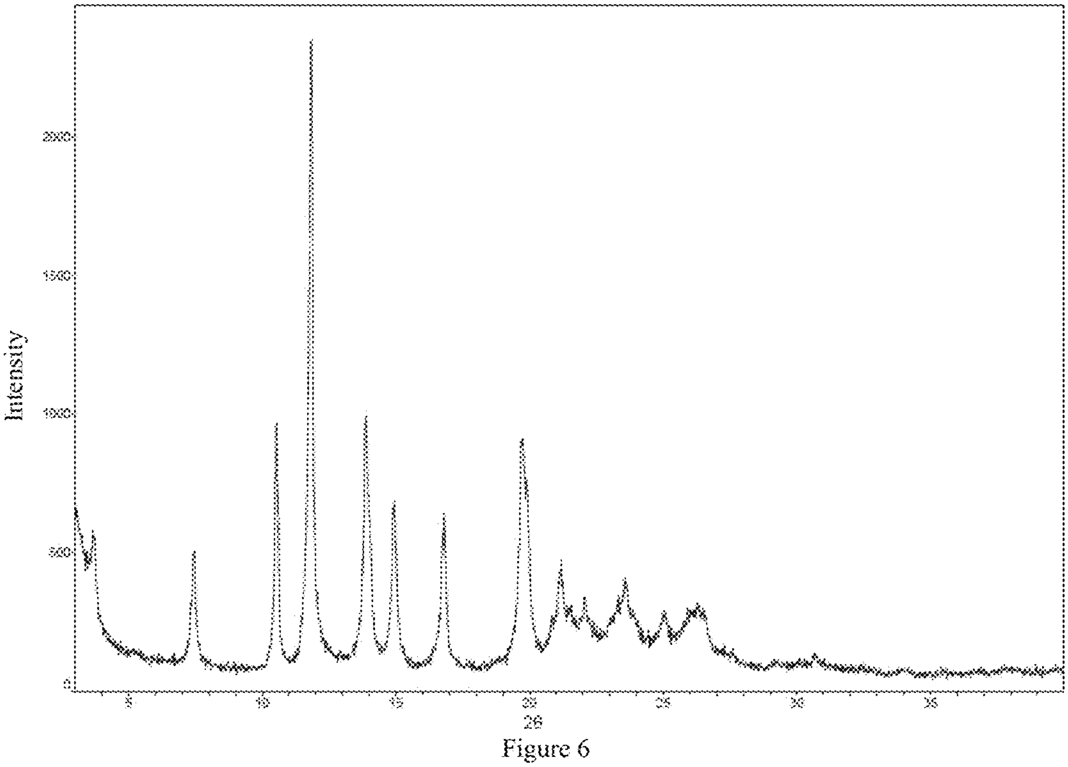
FIG. 6 depicts a XRPD pattern of Compound 26 in Embodiment 15.

The Compound 26 was recrystallized to obtain a pure crystal I of Compound 26. The pure compound was detected by X-ray powder diffraction (XRPD), and the results were showed in the following Table 6 and FIG. 6.

TABLE 6

XRPD data of crystal I of Compound 26

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 3.625 | 24.3558 | 152 | 434 | 19.4 | 9958 | 35.9 | 0.380 |
| 2 | 7.422 | 11.9013 | 97 | 410 | 18.3 | 5487 | 19.8 | 0.222 |
| 3 | 10.518 | 8.4040 | 99 | 871 | 38.8 | 8405 | 30.3 | 0.160 |
| 4 | 11.804 | 7.4908 | 116 | 2242 | 100.0 | 27763 | 100.0 | 0.205 |
| 5 | 13.850 | 6.3884 | 140 | 850 | 37.9 | 12733 | 45.9 | 0.248 |
| 6 | 14.921 | 5.9323 | 130 | 554 | 24.7 | 6840 | 24.6 | 0.204 |
| 7 | 16.772 | 5.2817 | 90 | 552 | 24.6 | 7894 | 28.4 | 0.237 |
| 8 | 19.714 | 4.4996 | 137 | 773 | 34.5 | 16334 | 58.8 | 0.350 |
| 9 | 21.155 | 4.1963 | 199 | 272 | 12.1 | 5021 | 18.1 | 0.306 |
| 10 | 21.507 | 4.1284 | 193 | 116 | 5.2 | 4958 | 17.9 | 0.708 |
| 11 | 22.049 | 4.0280 | 226 | 116 | 5.2 | 1215 | 4.4 | 0.173 |
| 12 | 23.535 | 3.7770 | 191 | 217 | 9.7 | 6232 | 22.4 | 0.476 |
| 13 | 25.034 | 3.5541 | 196 | 95 | 4.2 | 976 | 3.5 | 0.170 |
| 14 | 25.989 | 3.4256 | 177 | 117 | 5.2 | 5377 | 19.4 | 0.761 |

Embodiment 16

Preparation of (2-(2-((2,6-dichlorophenyl)amino) phenyl)acetoxy)methyl 3-formyl-1H-indole-1-carboxylate (Compound 9)

(1) Synthesis of Silver 2-(2-((2,6-dichlorophenyl) amino)phenyl)acetate (R9_Ag+)

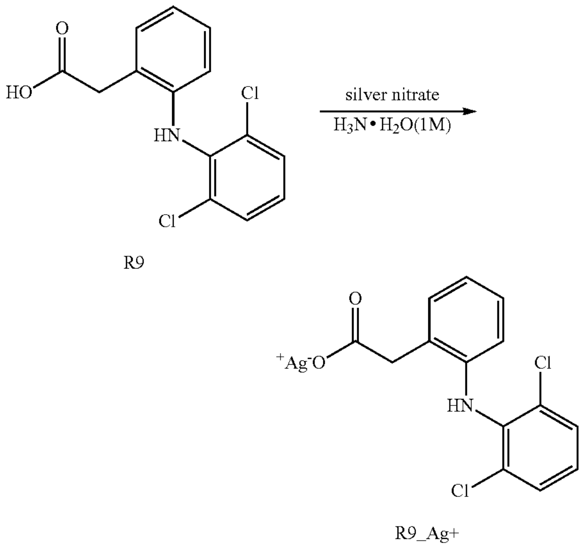

R9

R9_Ag+

2-(2-((2,6-dichlorophenyl)amino)phenyl)acetic acid (Compound R9) (3.0 g, 10.1 mmol) was dissolved in 1M ammonia hydroxide solution (30 mL). The mixture was cooled to 0° C., followed by adding silver nitrate aqueous solution (1.7 g, 10.1 mmol, 10 mL) to the mixture, and then the mixture was reacted for half an hour at 0° C. A great amount of white solid precipitated, and the mixture was filtered to gather the white solid product. The filter cake was washed by water, and dried to obtain silver 2-(2-((2-,6-dichlorophenyl)amino)phenyl)acetate (R9_Ag+) (2.9 g, yield: 71%).

(2) Synthesis of (2-(2-((2,6-dichlorophenyl)amino) phenyl)acetoxy)methyl3-formyl-1H-indole-1-carboxylate (Compound 9)

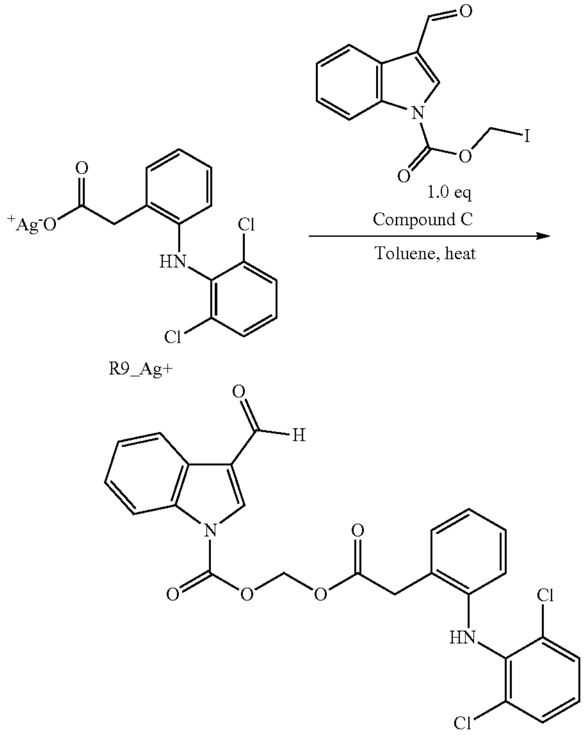

R9_Ag+

Compound 9

Silver 2-(2-((2-,6-dichlorophenyl)amino)phenyl)acetate (R9_Ag+) (2.2 g, 5.5 mmol) and iodomethyl 3-formyl-1H-indole-1-carboxylate (Compound C) (1.5 g, 4.6 mmol) were dissolved in methylbenzene, and the mixture was reacted for 4 hours at 40° C. LCMS showed that iodomethyl 3-formyl-1H-indole-1-carboxylate (Compound C) was reacted completely. The reaction liquid was filtered, and the filtrate was extracted by ethyl acetate (3×20 mL) and water (40 mL). Subsequently, the organic phases were combined, washed by saturated saline (20 ml), dried by anhydrous sodium sulfate, filtered, concentrated under reduced pressure, and purified through a chromatographic column (eluent:petroleum ether: ethyl acetate=100:1 to 1:1), to obtain a white solid product, i.e. a desirable compound, (2-(2-((2,6-dichlorophenyl) amino)phenyl)acetoxy)methyl 3-formyl-1H-indole-1-carboxylate (Compound 9) (500 mg, yield: 43.7%).

The characteristic data of Compound 9 was: $^{1}$H NMR (400 MHz, DMSO) δ 10.08 (s, 1H), 8.68 (s, 1H), 8.14 (dd, J=19.1, 7.6 Hz, 2H), 7.45 (t, J=12.0 Hz, 4H), 7.24-7.13 (m, 2H), 7.03 (dd, J=17.5, 10.2 Hz, 2H), 6.82 (d, J=7.4 Hz, 1H), 6.20 (d, J=8.4 Hz, 1H), 6.11 (s, 2H), 3.98 (s, 3H).

The purity of Compound 9 detected by HPLC was 98.7% at 254 nm and 98.8% at 214 nm, measured according to the normalization method of peak area.

Figure 7:
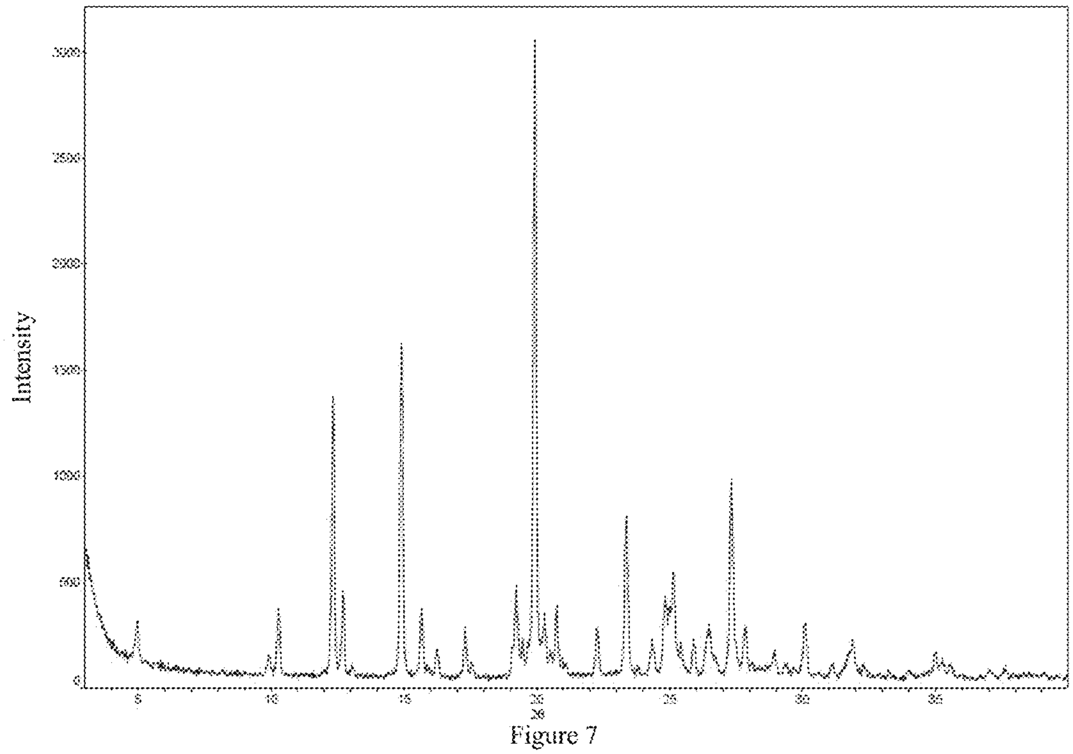
FIG. 7 depicts a XRPD pattern of Compound 9 in Embodiment 16.

The Compound 9 was recrystallized to obtain a pure crystal I of Compound 9. The pure compound was detected by X-ray powder diffraction (XRPD), and the results were showed in the following Table 7 and FIG. 7.

TABLE 7

XRPD data of crystal I of Compound 9

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 4.946 | 17.8528 | 132 | 186 | 6.2 | 1351 | 5.3 | 0.12 |
| 2 | 9.897 | 8.9294 | 57 | 92 | 3.1 | 870 | 3.4 | 0.157 |
| 3 | 10.250 | 8.6226 | 56 | 315 | 10.5 | 2401 | 9.5 | 0.126 |
| 4 | 12.311 | 7.1836 | 54 | 1320 | 43.9 | 9469 | 37.3 | 0.119 |
| 5 | 12.681 | 6.9747 | 54 | 400 | 13.3 | 3081 | 12.1 | 0.128 |
| 6 | 14.885 | 5.9468 | 55 | 1571 | 52.3 | 11612 | 45.8 | 0.122 |
| 7 | 15.641 | 5.6608 | 56 | 316 | 10.5 | 2634 | 10.4 | 0.138 |
| 8 | 16.227 | 5.4579 | 51 | 128 | 4.3 | 1122 | 4.4 | 0.145 |
| 9 | 17.263 | 5.1324 | 47 | 237 | 7.9 | 1836 | 7.2 | 0.128 |
| 10 | 17.535 | 5.0536 | 46 | 76 | 2.5 | 732 | 2.9 | 0.159 |
| 11 | 19.208 | 4.6169 | 43 | 443 | 14.7 | 4830 | 19 | 0.181 |
| 12 | 19.440 | 4.5624 | 53 | 181 | 6.0 | 1611 | 6.3 | 0.147 |
| 13 | 19.907 | 4.4563 | 59 | 3005 | 100 | 25371 | 100.0 | 0.140 |
| 14 | 20.260 | 4.3796 | 104 | 251 | 8.4 | 3661 | 14.4 | 0.242 |
| 15 | 20.725 | 4.2824 | 60 | 330 | 11.0 | 3862 | 15.2 | 0.194 |
| 16 | 22.231 | 3.9955 | 60 | 224 | 7.5 | 1532 | 6.0 | 0.113 |
| 17 | 23.354 | 3.8058 | 68 | 743 | 24.7 | 6119 | 24.1 | 0.136 |
| 18 | 24.314 | 3.6577 | 75 | 153 | 5.1 | 1063 | 4.2 | 0.115 |
| 19 | 24.818 | 3.5846 | 71 | 359 | 11.9 | 8547 | 33.7 | 0.394 |
| 20 | 25.111 | 3.5434 | 72 | 477 | 15.9 | 8890 | 35.0 | 0.309 |
| 21 | 25.383 | 3.5060 | 71 | 137 | 4.6 | 2313 | 9.1 | 0.280 |
| 22 | 25.871 | 3.4410 | 76 | 155 | 5.2 | 945 | 3.7 | 0.101 |
| 23 | 26.455 | 3.3663 | 70 | 229 | 7.6 | 3115 | 12.3 | 0.225 |
| 24 | 27.294 | 3.2648 | 77 | 907 | 30.2 | 7985 | 31.5 | 0.146 |
| 25 | 27.817 | 3.2045 | 80 | 211 | 7.0 | 2136 | 8.4 | 0.168 |
| 26 | 28.910 | 3.0858 | 80 | 94 | 3.1 | 660 | 2.6 | 0.116 |
| 27 | 29.314 | 3.0442 | 68 | 49 | 1.6 | 559 | 2.2 | 0.189 |
| 28 | 30.075 | 2.9689 | 65 | 241 | 8.0 | 2186 | 8.6 | 0.150 |
| 29 | 31.093 | 2.8739 | 55 | 57 | 1.9 | 439 | 1.7 | 0.128 |
| 30 | 31.852 | 2.8072 | 53 | 172 | 5.7 | 2833 | 11.2 | 0.273 |
| 31 | 32.260 | 2.7726 | 51 | 62 | 2.1 | 930 | 3.7 | 0.248 |
| 32 | 34.023 | 2.6328 | 48 | 36 | 1.2 | 288 | 1.1 | 0.132 |
| 33 | 35.003 | 2.5614 | 49 | 118 | 3.9 | 2314 | 9.1 | 0.325 |
| 34 | 35.239 | 2.5448 | 48 | 88 | 2.9 | 1523 | 6.0 | 0.287 |
| 35 | 35.530 | 2.5245 | 49 | 64 | 2.1 | 1007 | 4.0 | 0.261 |
| 36 | 37.008 | 2.4270 | 42 | 48 | 1.6 | 627 | 2.5 | 0.216 |
| 37 | 37.628 | 2.3885 | 48 | 54 | 1.8 | 466 | 1.8 | 0.143 |

Embodiment 17

Preparation of (2-(2-((2,6-dichlorophenyl)amino) phenyl)acetoxy)methyl 3-(hydroxymethyl)-1H-indole-1-carboxylate (Compound 27)

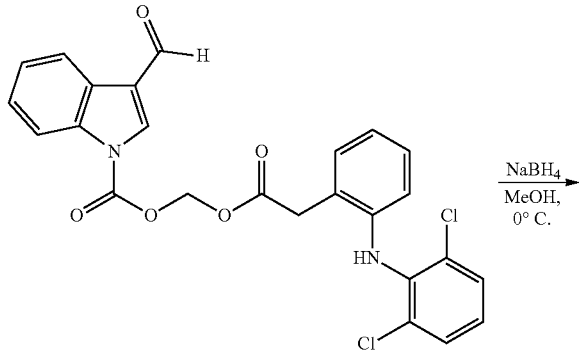

Compound 9

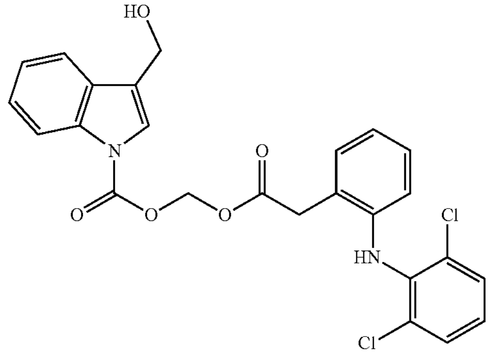

Compound 27

(2-(2-((2-,6-dichlorophenyl)amino)phenyl)acetoxy) methyl 3-formyl-1H-indole-1-carboxylate (Compound 9) (80 mg, 0.16 mmol) was dissolved in anhydrous tetrahydrofuran (3 ml). After the temperature was decreased to 0° C., sodium borohydride (6 mg, 0.16 mmol) was added, and the mixture was reacted for 2 hours at 0° C. TLC (petroleum ether:ethyl acetate=3:1) showed that the reaction was completed. Saturated ammonia chloride aqueous solution (15 ml) was added to the reaction liquid, and the liquid was extracted by ethyl acetate (3×20 mL). Subsequently, the organic phases were combined, washed by water (20 ml) and saturated saline (20 ml), dried by anhydrous sodium sulfate, filtered, concentrated under reduced pressure, and purified through a chromatographic column (eluent:petroleum ether: ethyl acetate=100:1 to 1:1), to obtain a light yellow solid product, i.e. a desirable compound, (2-(2-((2,6-dichlorophenyl)amino)phenyl)acetoxy)methyl 3-(hydroxymethyl)-1H-indole-1-carboxylate (Compound 27) (110 mg, yield: 52%).

The characteristic data of Compound 27 was: $^1H$ NMR (400 MHz, DMSO) δ 8.04 (d, J=7.7 Hz, 1H), 7.67 (d, J=7.7 Hz, 1H), 7.57-7.44 (m, 3H), 7.31 (dt, J=25.2, 6.8 Hz, 2H), 7.19 (t, J=8.1 Hz, 2H), 7.10-6.95 (m, 2H), 6.80 (t, J=7.4 Hz, 1H), 6.25-6.15 (m, 1H), 6.05 (s, 2H), 5.15 (t, J=5.5 Hz, 1H), 4.67-4.56 (m, 2H), 3.95 (s, 2H).

The purity of compound 27 detected by HPLC was 95.96% at 254 nm and 95.28% at 214 nm, measured according to the normalization method of peak area.

Figure 8:
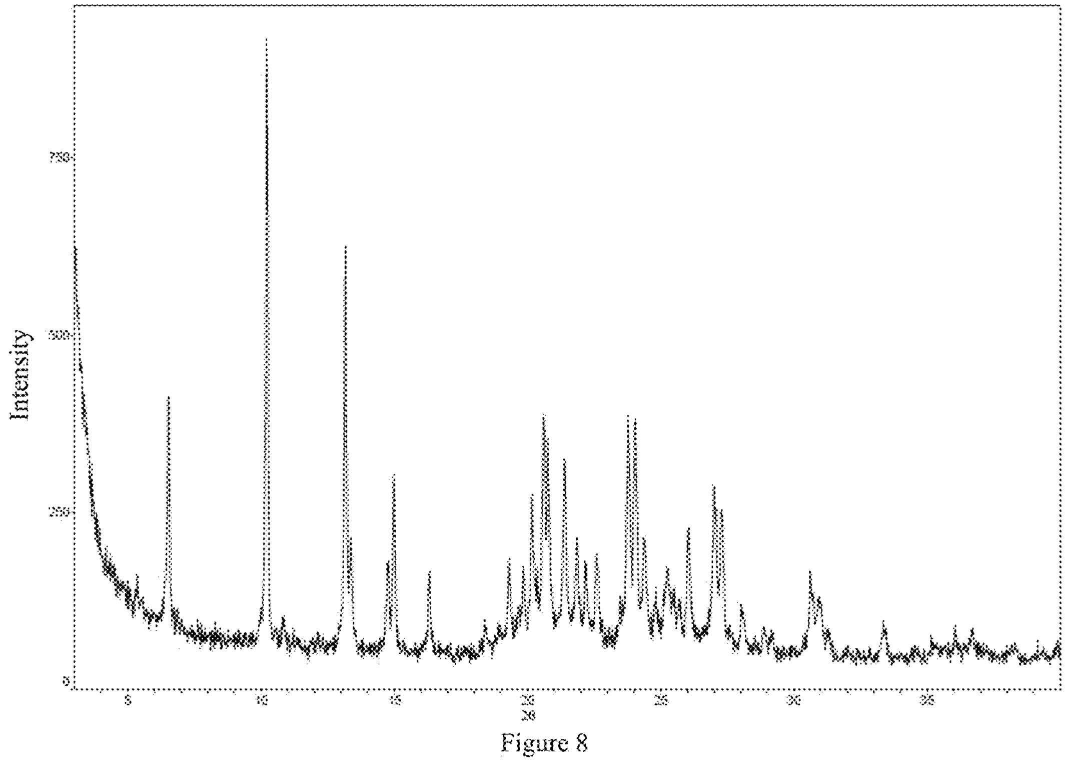
FIG. 8 depicts a XRPD pattern of Compound 27 in Embodiment 17.

The Compound 27 was recrystallized to obtain a pure crystal I of Compound 27. The pure compound was detected by X-ray powder diffraction (XRPD), and the results were showed in the following Table 8 and FIG. 8.

TABLE 8

XRPD data of crystal I of Compound 27

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 5.356 | 16.4848 | 112 | 49 | 5.7 | 336 | 6.2 | 0.114 |
| 2 | 6.529 | 13.5257 | 87 | 328 | 38.3 | 2498 | 46 | 0.126 |
| 3 | 10.212 | 8.6549 | 64 | 856 | 100.0 | 5427 | 100.0 | 0.105 |
| 4 | 10.863 | 8.1376 | 68 | 34 | 4.0 | 147 | 2.7 | 0.072 |
| 5 | 13.168 | 6.7177 | 58 | 568 | 66.4 | 4164 | 76.7 | 0.121 |
| 6 | 13.380 | 6.6120 | 58 | 138 | 16.1 | 2111 | 38.9 | 0.253 |
| 7 | 14.766 | 5.9943 | 53 | 128 | 15.0 | 1173 | 21.6 | 0.152 |
| 8 | 14.986 | 5.9070 | 52 | 250 | 29.2 | 1985 | 36.6 | 0.131 |
| 9 | 16.321 | 5.4264 | 47 | 119 | 13.9 | 1161 | 21.4 | 0.162 |
| 10 | 18.443 | 4.8066 | 57 | 30 | 3.5 | 189 | 3.5 | 0.104 |
| 11 | 19.308 | 4.5932 | 76 | 108 | 12.6 | 770 | 14.2 | 0.118 |
| 12 | 19.848 | 4.4695 | 94 | 79 | 9.2 | 448 | 8.3 | 0.094 |
| 13 | 20.164 | 4.4001 | 93 | 183 | 21.4 | 1864 | 34.3 | 0.169 |
| 14 | 20.609 | 4.3062 | 98 | 290 | 33.9 | 3383 | 62.3 | 0.193 |
| 15 | 21.391 | 4.1505 | 97 | 228 | 26.6 | 1734 | 32.0 | 0.126 |
| 16 | 21.843 | 4.0656 | 89 | 128 | 15.0 | 1217 | 22.4 | 0.157 |
| 17 | 22.181 | 4.0044 | 99 | 83 | 9.7 | 388 | 7.1 | 0.077 |
| 18 | 22.583 | 3.9341 | 86 | 105 | 12.3 | 679 | 12.5 | 0.107 |
| 19 | 23.770 | 3.7402 | 82 | 304 | 35.5 | 2881 | 53.1 | 0.157 |
| 20 | 24.054 | 3.6966 | 82 | 299 | 34.9 | 3192 | 58.8 | 0.177 |
| 21 | 24.372 | 3.6491 | 87 | 127 | 14.8 | 1313 | 24.2 | 0.171 |
| 22 | 24.816 | 3.5849 | 88 | 54 | 6.3 | 225 | 4.1 | 0.069 |
| 23 | 25.249 | 3.5243 | 91 | 80 | 9.3 | 1346 | 24.8 | 0.279 |

TABLE 8-continued

XRPD data of crystal I of Compound 27

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 24 | 25.676 | 3.4666 | 81 | 48 | 5.6 | 453 | 8.3 | 0.156 |
| 25 | 26.045 | 3.4184 | 88 | 139 | 16.2 | 980 | 18.1 | 0.117 |
| 26 | 27.004 | 3.2991 | 71 | 218 | 25.5 | 2853 | 52.6 | 0.217 |
| 27 | 27.278 | 3.2667 | 70 | 184 | 21.5 | 2378 | 43.8 | 0.214 |
| 28 | 28.034 | 3.1802 | 63 | 52 | 6.1 | 414 | 7.6 | 0.132 |
| 29 | 28.868 | 3.0902 | 52 | 37 | 4.3 | 484 | 8.9 | 0.217 |
| 30 | 29.147 | 3.0612 | 50 | 36 | 4.2 | 487 | 9.0 | 0.224 |
| 31 | 30.606 | 2.9186 | 50 | 117 | 13.7 | 2470 | 45.5 | 0.350 |
| 32 | 30.934 | 2.8883 | 50 | 80 | 9.3 | 2117 | 39.0 | 0.438 |
| 33 | 31.283 | 2.8569 | 53 | 33 | 3.9 | 162 | 3.0 | 0.081 |
| 34 | 33.354 | 2.6842 | 43 | 52 | 6.1 | 526 | 9.7 | 0.167 |
| 35 | 36.047 | 2.4895 | 51 | 38 | 4.4 | 160 | 2.9 | 0.070 |
| 36 | 36.698 | 2.4468 | 48 | 37 | 4.3 | 620 | 11.4 | 0.277 |

Embodiment 18

Preparation of (3-formyl-1H-indol-1-yl)methyl hexanoate (Compound 28)

(1) Synthesis of Chloromethyl Hexanoate

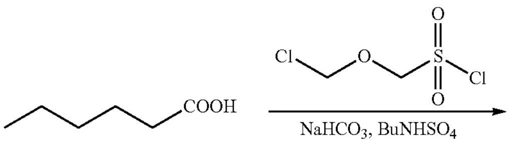

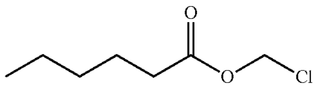

Hexanoic acid (1.0 g, 8.62 mmol), sodium bicarbonate (2.89 g. 34.48 mmol), and $BuNHSO_4$ (0.29 g, 0.862 mmol) were dissolved in a mixed solution of dichloromethane and water (10 mL/10 mL), and the mixture was stirred for 10 min. After the temperature was cooled to 0° C., (chloromethoxy)methanesulfonyl chloride (1.71 g, 10.34 mmol) was dripped dropwise. Then, the temperature was increased to room temperature, and the mixture was reacted for 2 hours. TLC (petroleum ether:ethyl acetate=5:1) showed that the reaction was completed. The reaction liquid was subjected to liquid separation. The aqueous phase was extracted by dichloromethane (30 mL×3), and the organic phase was washed by water (30 mL×3). Subsequently, the organic phase was combined, washed by saturated saline (50 ml), dried by anhydrous sodium sulfate, filtered, concentrated under reduced pressure, and purified through a chromatographic column (eluent:petroleum ether:ethyl acetate=100:1 to 5:1), to obtain a yellow oily product, i.e. a desirable compound, chloromethyl hexanoate (400 mg, yield: 28.3%).

(2) Synthesis of (3-formyl-1H-indol-1-yl)methyl hexanoate (Compound 28)

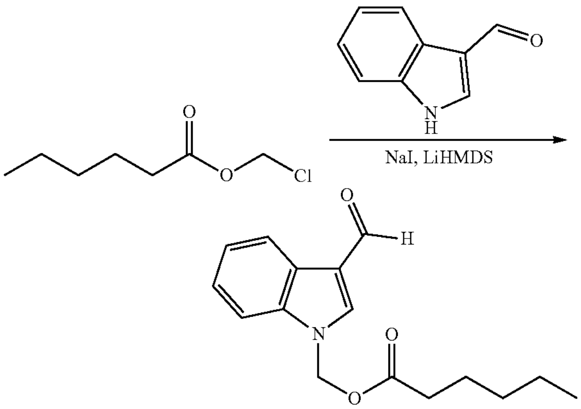

Compound 28

Sodium iodide (18 mg, 0.122 mmol) was added to a solution of 1H-indole-3-carbaldehyde (176 mg, 1.22 mmol) dissolved in tetrahydrofuran. Lithium bis(trimethylsilyl)amide (1.83 mL, 1.83 mmol) was dripped into the mixture under water-free and oxygen-free conditions at −78° C., and the mixture was reacted for half an hour at −78° C. Then, a solution of chloromethyl hexanoate (400 mg, 2.44 mmol) dissolved in THF was dripped, and the mixture was reacted for 3 hours at −78° C. LCMC (MC20-874-3-P1B) showed that the reaction was completed. Ammonia chloride aqueous solution (10 mL) was added to the reaction liquid. Then, water (50 mL) was added for dilution, and the reaction liquid was extracted by ethyl acetate (30 mL×3). Subsequently, the organic phases were combined, washed by saturated saline (50 ml), dried by anhydrous sodium sulfate, filtered, concentrated under reduced pressure, and purified through PRE-TLC (PE:EA=4:1, Rf=0.4), to obtain a yellow oily product, i.e. a desirable compound, (3-formyl-1H-indol-1-yl)methyl hexanoate (200 mg, yield: 30.0%).

The characteristic data of Compound 28 was: 1H NMR (400 MHz, DMSO): δ 1H NMR (400 MHz, CDCl3) δ 10.02 (s, 1H), 8.30 (dd, J=6.9, 1.5 Hz, 1H), 7.91 (s, 1H), 7.58-7.46

(m, 1H), 7.44-7.28 (m, 2H), 6.11 (s, 2H), 2.31 (t, J=7.5 Hz, 2H), 1.64-1.51 (m, 2H), 1.31-1.11 (m, 4H), 0.81 (t, J=7.0 Hz, 3H).

Embodiment 19

Preparation of (3-(hydroxymethyl)-1H-indol-1-yl) methyl hexanoate (Compound 37)

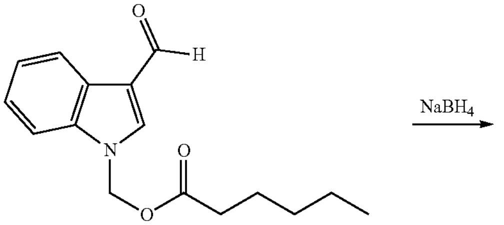

Compound 28

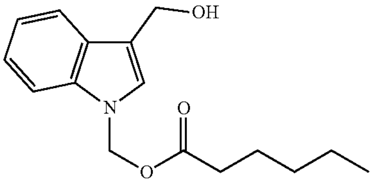

Compound 37

(3-formyl-1H-indol-1-yl)methyl hexanoate (400 mg, 1.47 mmol) was dissolved in anhydrous methanol (6 ml). After the temperature was decreased to 0° C., sodium borohydride (56 mg, 1.47 mmol) was added, and the mixture was reacted for half an hour at 0° C. TLC (petroleum ether:ethyl acetate=3:1) detection showed that the reaction was completed. Saturated ammonia chloride aqueous solution (15 ml) was added to the reaction liquid, and the liquid was extracted by ethyl acetate (3x20 mL). Subsequently, the organic phases were combined, washed by water (20 ml) and saturated saline (20 ml), dried by anhydrous sodium sulfate, filtered, concentrated under reduced pressure, and purified through PRE-TLC (PE:EA=3:1, Rf=0.25), to obtain a light yellow oily product, i.e. a desirable compound, (3-(hydroxymethyl)-1H-indol-1-yl)methyl hexanoate (Compound 37) (115 mg, yield: 28.5%).

The characteristic data of Compound 37 was: 1H NMR (400 MHz, DMSO) δ 7.61 (d, J=7.8 Hz, 1H), 7.54 (d, J=8.2 Hz, 1H), 7.34 (s, 1H), 7.19 (dd, J=11.2, 4.0 Hz, 1H), 7.10 (t, J=7.4 Hz, 1H), 6.17 (s, 2H), 4.90 (s, 1H), 4.62 (s, 2H), 2.26 (t, J=7.3 Hz, 2H), 1.46 (dd, J=14.6, 7.3 Hz, 2H), 1.23-1.09 (m, 4H), 0.78 (t, J=6.9 Hz, 3H).

The purity of Compound 37 detected by HPLC was 97.07% at 254 nm and 96.37% at 214 nm, measured according to the normalization method of peak area.

Embodiment 20

Preparation of (3-formyl-1H-indol-1-yl)methyl octanoate (Compound 29)

(1) Synthesis of chloromethyl octanoate

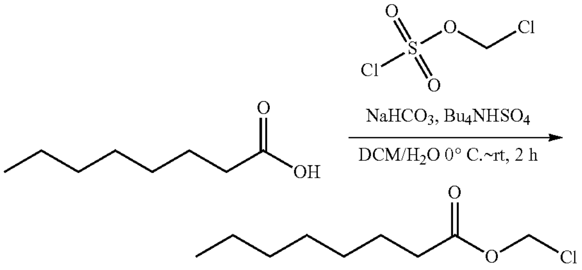

Octanoic acid (2.0 g, 13.868 mmol), sodium bicarbonate (4.660 g, 55.473 mmol), and tetrabutylammonium hydrogen sulfate ($Bu_4NHSO_4$) (471 mg, 1.387 mmol) were dissolved in dichloromethane and water (32 ml, 1:1) and the mixture was stirred for 5 min at room temperature. Chloromethyl sulfurochloridate (2.746 g, 16.642 mmol) was gradually added to the mixture and reacted for 2 hours at room temperature. TLC (petroleum ether:ethyl acetate=5:1) showed that the reaction was completed. The mixture was extracted by dichloromethane (2x30 mL). Subsequently, the organic phases were combined, washed by water (60 mL) and saturated saline (60 mL), dried by anhydrous sodium sulfate, filtered, concentrated under reduced pressure, and purified through a chromatographic column (eluent:petroleum ether:ethyl acetate=80:1 to 100:1), to obtain a colorless oily product, i.e. a desirable compound, chloromethyl octanoate (1.827 g, yield: 68.4%).

The characteristic data of chloromethyl octanoate was 1H NMR (400 MHz, CDCl3) δ 5.71 (s, 2H), 2.38 (t, J=7.5 Hz, 2H), 1.73-1.58 (m, 2H), 1.36-1.22 (m, 8H), 0.88 (t, J=6.9 Hz, 3H).

(2) Synthesis of (3-formyl-1H-indol-1-yl)methyl octanoate (Compound 29)

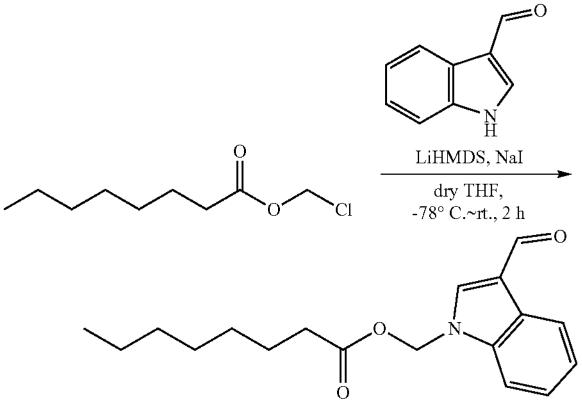

Compound 29

1H-indole-3-carboxaldehyde (400 mg, 2.755 mmol) and sodium iodide (83 mg, 0.551 mmol) were dissolved in anhydrous tetrahydrofuran (6 mL) under argon protection. After the temperature was decreased to −78° C., lithium bis(trimethylsilyl)amide (1M, 4.1 mL, 4.132 mmol) was dropwise dripped into the mixture and was reacted for half an hour at −78° C. Then, a solution of chloromethyl octanoate (1.061 g, 5.510 mmol) dissolved in tetrahydrofuran (6 mL) was dripped into the reaction liquid, and the mixture was reacted for two hours at −78° C. Subsequently, TLC (petroleum ether:ethyl acetate=3:1) showed that the reaction was completed. Saturated ammonia chloride aqueous solution (20 mL) was added to the reaction liquid. The reaction liquid was extracted by ethyl acetate (2×50 mL). Subsequently, the organic phases were combined, washed by water (100 mL) and saturated saline (100 mL), dried by anhydrous sodium sulfate, filtered, concentrated under reduced pressure, and purified through a chromatographic column (eluent:petroleum ether:ethyl acetate=100:1-70:1), to obtain a yellow oily product, i.e. a desirable compound, (3-formyl-1H-indol-1-yl)methyl octanoate (Compound 29) (580 mg, yield: 69.9%).

The characteristic data of Compound 29 was: 1H NMR (400 MHz, CDCl3) δ 10.03 (s, 1H), 8.31 (dd, J=6.8, 1.5 Hz, 1H), 7.92 (s, 1H), 7.53 (dd, J=7.1, 1.2 Hz, 1H), 7.44-7.31 (m, 2H), 6.12 (s, 2H), 2.32 (t, J=7.5 Hz, 2H), 1.71-1.47 (m, 2H), 1.31-1.08 (m, 8H), 0.84 (t, J=7.0 Hz, 3H).

The purity of Compound 29 detected by HPLC was 99.06% at 254 nm and 99.06% at 214 nm, measured according to the normalization method of peak area.

Embodiment 21

Preparation of (3-(hydroxymethyl)-1H-indol-1-yl) methyl octanoate (Compound 38)

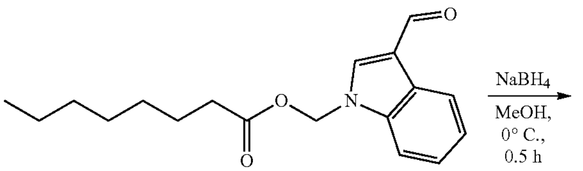

Compound 29

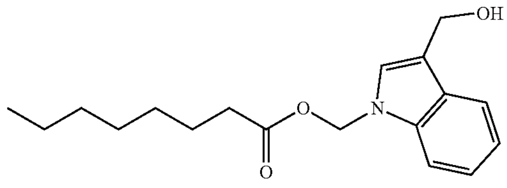

Compound 38

(3-formyl-1H-indol-1-yl)methyl octanoate (Compound 29) (250 mg, 0.829 mmol) was dissolved in anhydrous methanol (3 ml). After the temperature was decreased to 0° C., sodium borohydride (31 mg, 0.829 mmol) was added to and the mixture, and the mixture was reacted for half an hour at 0° C. TLC (petroleum ether:ethyl acetate=3:1) detection showed that the reaction was completed. Saturated ammonia chloride aqueous solution (10 ml) was added to the reaction liquid, and the liquid was extracted by ethyl acetate (2×30 mL). Subsequently, the organic phases were combined, washed by water (60 ml) and saturated saline (60 ml), dried by anhydrous sodium sulfate, filtered, and concentrated under reduced pressure. The obtained crude product was purified through prep-TLC (eluent:petroleum ether:ethyl acetate=3:1), to obtain a yellow oily product, i.e. a desirable compound, (3-(hydroxymethyl)-1H-indol-1-yl)methyl hexanoate (Compound 38) (60 mg, yield: 24.0%), which was combined with MC20-877-017P and MC20-877-018P to obtain 103 mg of a desirable compound, (3-(hydroxymethyl)-1H-indol-1-yl)methyl hexanoate (Compound 38).

The characteristic data of Compound 38 was: 1H NMR (400 MHz, DMSO) δ 7.61 (d, J=7.8 Hz, 1H), 7.53 (d, J=8.2 Hz, 1H), 7.34 (s, 1H), 7.19 (t, J=7.1 Hz, 1H), 7.09 (t, J=7.1 Hz, 1H), 6.17 (s, 2H), 4.90 (t, J=5.4 Hz, 1H), 4.61 (d, J=5.3 Hz, 2H), 2.26 (t, J=7.3 Hz, 2H), 1.51-1.39 (m, 2H), 1.17 (d, J=13.5 Hz, 8H), 0.82 (t, J=7.0 Hz, 3H).

The purity of Compound 38 detected by HPLC was 93.04% at 254 nm and 93.86% at 214 nm, measured according to the normalization method of peak area.

Embodiment 22

Preparation of (3-formyl-1H-indol-1-yl)methyl decanoate (Compound 30)

(1) Synthesis of Chloromethyl Decanoate

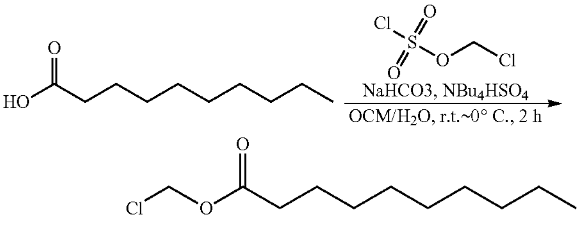

Decanoic acid (1.0 g, 5.80 mmol), sodium bicarbonate (1.95 g, 23.20 mmol), and tetrabutylammonium hydrogen sulfate (197 mg, 0.58 mmol) were dissolved in dichloromethane (10 mL) and water (10 mL) under the argon protection, and the mixture was stirred for 5 min at room temperature. Subsequently, the reaction was placed on an ice-water bath at 0° C., and chloromethyl sulfurochloridate (1.15 g, 6.96 mmol) was dropwise dripped into the reaction liquid. After the materials were added, the temperature was increased to room temperature, and the mixture was continued to react for 2 hours. TLC (petroleum ether:ethyl acetate=20:1) detection showed that the reaction was completed. Then, water (50 ml) was added to the reaction liquid, which was further poured out into a separating funnel for separating the organic phases. Dichloromethane was added to the aqueous phase for extraction (3×50 mL). The organic phases were combined, washed by water (80 ml) and saturated saline (80 ml), dried by anhydrous sodium sulfate, filtered, and concentrated under reduced pressure. The obtained crude product was passed through a chromatographic column, and separated and purified through a rapid silica gel column (eluent:petroleum ether:ethyl acetate=100:1 to 100:5), to obtain a colorless liquid product, i.e. a desirable compound, chloromethyl decanoate (1.04 g, yield: 81.2%).

The characteristic data of chloromethyl decanoate was: 1H NMR (400 MHz, CDCl3) δ 5.71 (s, 2H), 2.38 (t, J=7.5 Hz, 2H), 1.69-1.59 (m, 2H), 1.31 (s, 2H), 1.28 (d, J=13.6 Hz, 10H), 0.88 (t, J=6.8 Hz, 3H).

(2) Synthesis of (3-formyl-1H-indol-1-yl)methyl decanoate (Compound 30)

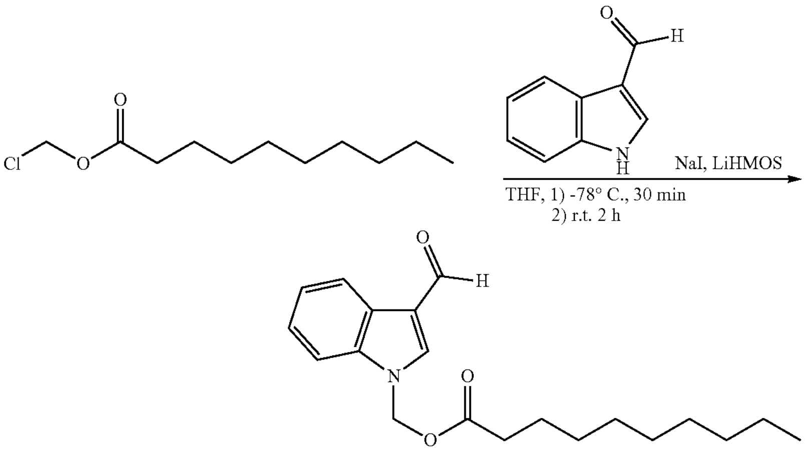

Compound 30

3-formyl-1H-indole (438 mg, 3.02 mmol) and sodium iodide (46 mg, 0.30 mmol) were dissolved in anhydrous tetrahydrofuran (15 mL) under argon protection at −78° C. While the mixture was stirring, lithium bis(trimethylsilyl) amide (4.6 mL, 4.60 mmol, 1M) was added, and the mixture was reacted for half an hour. Subsequently, chloromethyl decanoate (1.00 g, 4.56 mmol) was gradually added. After adding, the temperature was increased to room temperature, and the mixture continued to be reacted for 2 hours under stirring. LCMS and TLC (petroleum ether:ethyl acetate=15:2) detection showed that the reaction was basically completed. Saturated ammonia chloride aqueous solution (50 mL) was added to the reaction liquid, and the reaction liquid was extracted by ethyl acetate (2×40 mL). Subsequently, the organic phases were combined, washed by saturated sodium thiosulfate (100 mL) and saturated saline (50 mL), dried by anhydrous sodium sulfate, filtered, and concentrated under reduced pressure. The obtained crude product was separated through a chromatographic column/rapid silica gel column (eluent:petroleum ether:ethyl acetate=100:1 to 100:15), and purified through prep-TLC (petroleum ether:ethyl acetate=5:1) to obtain a colorless oily liquid, i.e. a desirable compound, (3-formyl-1H-indol-1-yl)methyl decanoate (Compound 30) (660 mg, yield: 66.3%).

The characteristic data of Compound 30 was: $^1$H NMR (400 MHz, CDC13) δ 10.04 (s, 1H), 8.31 (dd, J=6.8, 1.5 Hz, 1H), 7.93 (s, 1H), 7.57-7.48 (m, 1H), 7.37 (dtd, J=14.6, 7.2, 1.3 Hz, 2H), 6.12 (s, 2H), 2.32 (t, J=7.5 Hz, 2H), 1.62-1.51 (m, 2H), 1.26 (d, J=6.5 Hz, 2H), 1.19 (d, J=2.6 Hz, 11H), 0.87 (t, J=7.0 Hz, 3H).

The purity of Compound 30 detected by HPLC was 96.43% at 254 nm and 97.83% at 214 nm, measured according to the normalization method of peak area.

Embodiment 23

Preparation of (3-(hydroxymethyl)-1H-indol-1-yl) methyl decanoate (Compound 39)

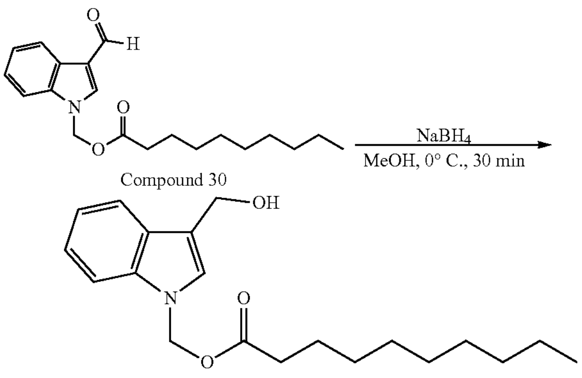

Compound 30

Compound 39

(3-formyl-1H-indol-1-yl)methyl decanoate (Compound 30) (450 mg, 1.37 mmol) was dissolved in anhydrous methanol (8 ml). After the temperature was decreased to 0° C., sodium borohydride (52 mg, 1.37 mmol) was added, and the mixture was reacted for half an hour at 0° C. TLC (petroleum ether:ethyl acetate=5:1) detection showed that the reaction was completed. Water (50 ml) was added to the reaction liquid, and the liquid was extracted by ethyl acetate (2×25 mL). Subsequently, the organic phases were combined, washed by saturated saline (30 ml), dried by anhydrous sodium sulfate, filtered, and concentrated under reduced pressure. The obtained crude product was purified twice through prep-TCL (eluent:petroleum ether:ethyl acetate=5:1), and then a light yellow oily product, i.e. a desirable compound (3-(hydroxymethyl)-1H-indol-1-yl) methyl decanoate (Compound 39) (187 mg, yield: 41.3%) was obtained.

The characteristic data of Compound 39 was: $^1$H NMR (400 MHz, DMSO): δ 7.61 (d, J=7.8 Hz, 1H), 7.53 (d, J=8.2

Hz, 1H), 7.34 (s, 1H), 7.23-7.14 (m, 1H), 7.09 (t, J=7.3 Hz, 1H), 6.17 (s, 2H), 4.90 (s, 1H), 4.62 (d, J=2.8 Hz, 2H), 2.26 (t, J=7.3 Hz, 2H), 1.51-1.38 (m, 2H), 1.23 (d, J=7.3 Hz, 2H), 1.16 (s, 10H), 0.85 (t, J=6.9 Hz, 3H).

The purity of Compound 39 detected by HPLC was 94.60% at 254 nm and 93.91% at 214 nm, measured according to the normalization method of peak area.

Embodiment 24

Preparation of (3-formyl-1H-indol-1-yl)methyl dodecanoate (Compound 31)

(1) Synthesis of Chloromethyl Dodecanoate

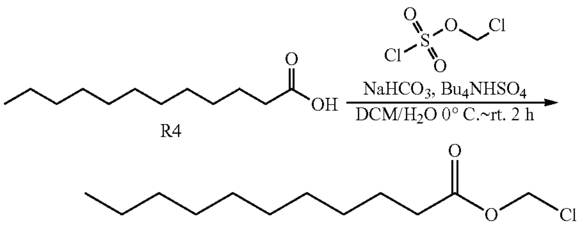

Dodecanoic acid (3.0 g, 14.976 mmol), sodium bicarbonate (5.032 g, 59.904 mmol), and tetrabutylammonium hydrogen sulfate (508 mg, 1.498 mmol) were dissolved in dichloromethane and water (40 mL, 1:1), and the mixture was stirred for 5 min at room temperature. Subsequently, chloromethyl sulfurochloridate (2.965 g, 17.971 mmol) was gradually added, and the mixture was reacted for 2 hours at room temperature. TLC (petroleum ether:ethyl acetate=5:1) showed that the reaction was completed. Dichloromethane was used for performing extraction (2×40 mL). The organic phases were combined, washed by water (80 ml) and saturated saline (80 ml), dried by anhydrous sodium sulfate, filtered, concentrated under reduced pressure, and purified through a chromatographic column (eluent:petroleum ether: ethyl acetate=100:1 to 80:1), to obtain a colorless oily product, i.e. a desirable compound, chloromethyl dodecanoate (3.490 g, yield: 93.7%).

The characteristic data of chloromethyl dodecanoate was: 1H NMR (400 MHz, CDCl3) δ 5.71 (s, 2H), 2.38 (t, J=7.5 Hz, 2H), 1.69-1.59 (m, 2H), 1.31 (s, 2H), 1.28 (d, J=13.6 Hz, 10H), 0.88 (t, J=6.8 Hz, 3H).

(2) Synthesis of (3-formyl-1H-indol-1-yl)methyl dodecanoate (Compound 31)

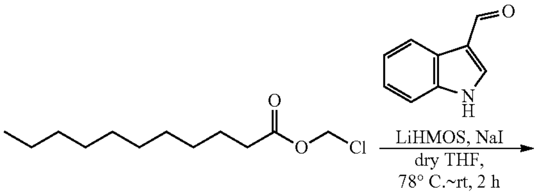

-continued

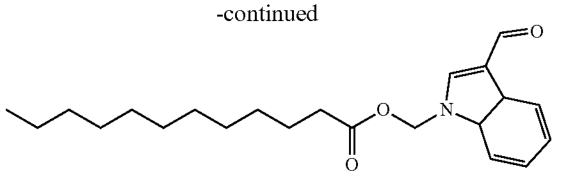

Compound 31

1H-indole-3-carboxaldehyde (600 mg, 4.133 mmol) and sodium iodide (62 mg, 0.413 mmol) were dissolved in anhydrous tetrahydrofuran (9 mL) under the argon protection. After the temperature was decreased to −78° C., a solution of lithium bis(trimethylsilyl)amide (1M, 6.2 mL, 6.200 mmol) in tetrahydrofuran (10 mL) was dropwise dripped to the reaction liquid, and the liquid was reacted for half an hour at −78° C. Subsequently, a solution of chloromethyl dodecanoate (2.0 g, 8.267 mmol) in tetrahydrofuran (10 mL) was dripped into the reaction liquid, and the liquid was reacted for 2 hours at −78° C. TLC (petroleum ether:ethyl acetate=3:1) showed that the reaction was completed. Saturated ammonia chloride aqueous solution (20 mL) was added to the reaction liquid, and the reaction liquid was extracted by ethyl acetate (2×30 mL). Subsequently, the organic phases were combined, washed by water (60 mL) and saturated saline (60 mL), dried by anhydrous sodium sulfate, filtered, concentrated under reduced pressure, and purified through a chromatographic column (eluent:petroleum ether:ethyl acetate=100:1-70:1), to obtain a light yellow solid product, i.e., a desirable compound, (3-formyl-1H-indol-1-yl)methyl dodecanoate (Compound 31) (665 mg, yield: 45.0%).

The characteristic data of Compound 31 was: 1H NMR (400 MHz, CDCl3) δ 10.05 (s, 1H), 8.44-8.24 (m, 1H), 7.92 (s, 1H), 7.53 (d, J=7.4 Hz, 1H), 7.45-7.29 (m, 2H), 6.12 (s, 2H), 2.32 (t, J=7.5 Hz, 2H), 1.57 (s, 2H), 1.21 (d, J=16.2 Hz, 16H), 0.88 (t, J=6.9 Hz, 3H).

The purity of Compound 31 detected by HPLC was 99.17% at 254 nm and 97.86% at 214 nm, measured according to the normalization method of peak area.

Embodiment 25

Preparation of (3-(hydroxymethyl)-1H-indol-1-yl) methyl dodecanoate (Compound 40)

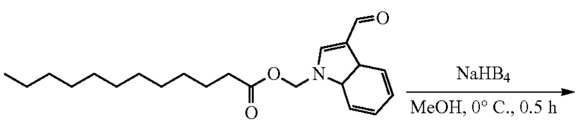

Compound 31

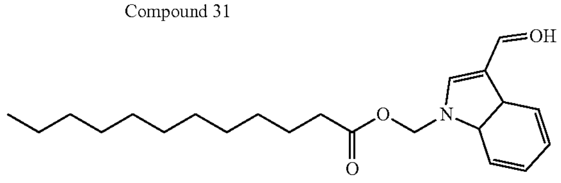

Compound 40

(3-formyl-1H-indol-1-yl)methyl dodecanoate (Compound 31) (250 mg, 0.695 mmol) was dissolved in anhydrous methanol (5 ml). After the temperature was decreased to 0° C., sodium borohydride (26 mg, 0.695 mmol) was added, and the mixture was reacted for half an hour at 0° C. TLC (petroleum ether:ethyl acetate=3:1) detection showed that the reaction was completed. Saturated ammonia chloride aqueous solution (10 ml) was added to the reaction liquid, and the liquid was extracted by ethyl acetate (2×20 mL). Subsequently, the organic phases were combined, washed by water (40 mL) and saturated saline (40 ml), dried by anhydrous sodium sulfate, filtered, and concentrated under reduced pressure. The obtained crude product was purified through prep-TCL (eluent:petroleum ether:ethyl acetate=3:1), and then a light yellow solid product, i.e. a desirable compound (3-(hydroxymethyl)-1H-indol-1-yl) methyl dodecanoate (Compound 40) (140 mg, yield: 56.0%) was obtained.

The characteristic data of Compound 40 was: 1H NMR (400 MHz, DMSO) δ 7.61 (d, J=7.8 Hz, 1H), 7.53 (d, J=8.2 Hz, 1H), 7.34 (s, 1H), 7.19 (t, J=7.2 Hz, 1H), 7.09 (t, J=7.2 Hz, 1H), 6.17 (s, 2H), 4.90 (t, J=5.4 Hz, 1H), 4.61 (d, J=5.3 Hz, 2H), 2.26 (t, J=7.3 Hz, 2H), 1.45 (s, 2H), 1.19 (d, J=26.6 Hz, 16H), 0.85 (t, J=6.8 Hz, 3H).

The purity of Compound 40 detected by HPLC was 98.23% at 254 nm and 97.03% at 214 nm, measured according to the normalization method of peak area.

Embodiment 26

Preparation of (3-formyl-1H-indol-1-yl)methyl tetradecanoate (Compound 32)

(1) Synthesis of Chloromethyl Tetradecanoate

Tetradecanoic acid (3.0 g, 13.136 mmol), sodium bicarbonate (4.414 g, 52.544 mmol), and tetrabutylammonium hydrogen sulfate (446 mg, 1.313 mmol) were dissolved in dichloromethane and water (40 mL, 1:1), and the mixture was stirred for 5 min at room temperature. Subsequently, chloromethyl sulfurochloridate (2.6 g, 15.764 mmol) was gradually added to the reaction liquid at 0° C. After adding, the reaction liquid was reacted for 2 hours at room temperature. TLC (petroleum ether:ethyl acetate=3:1) showed that the reaction was completed. Dichloromethane was used for performing extraction (2×40 mL). The organic phases were combined, washed by water (80 ml) and saturated saline (80 ml), dried by anhydrous sodium sulfate, filtered, concentrated under reduced pressure, and purified through a chromatographic column (eluent:petroleum ether:ethyl acetate=100:1 to 80:1), to obtain a semi-transparent solid product, a desirable compound, i.e. chloromethyl tetradecanoate (3.316 g, yield: 91.2%).

The characteristic data of chloromethyl tetradecanoate was: 1H NMR (400 MHz, CDCl3) δ 5.70 (s, 2H), 2.38 (t, J=7.5 Hz, 2H), 1.78-1.51 (m, 2H), 1.37-1.23 (m, 20H), 0.88 (t, J=6.8 Hz, 3H).

(2) Synthesis of (3-formyl-1H-indol-1-yl)methyl tetradecanoate (Compound 32)

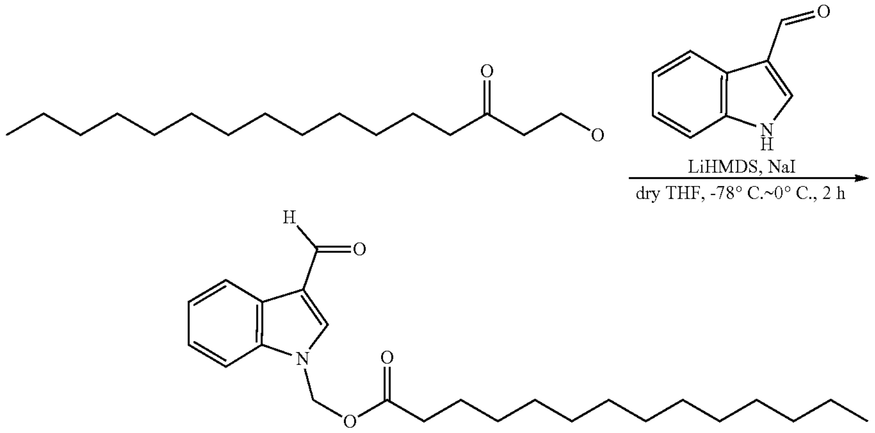

Compound 32

1H-indole-3-carboxaldehyde (400 mg, 2.755 mmol) and sodium iodide (41 mg, 0.275 mmol) were dissolved in anhydrous tetrahydrofuran (8 mL) under the protection of argon atmosphere. After the temperature was decreased to −78° C., a solution of lithium bis(trimethylsilyl)amide (1M, 4.1 mL, 4.132 mmol) in tetrahydrofuran was dropwise dripped to the reaction liquid, and the liquid was reacted for 1 hour at −78° C. Subsequently, a solution of chloromethyl tetradecanoate (1.525 g, 5.510 mmol) in tetrahydrofuran (8 mL) was dripped to the reaction liquid, and the liquid was reacted for 2 hours at −78° C. TLC (petroleum ether:ethyl acetate=3:1) showed that the reaction was completed. Saturated ammonia chloride aqueous solution (20 mL) was added to the reaction liquid, and the reaction liquid was extracted by ethyl acetate (2×20 mL). Subsequently, the organic phases were combined, washed by water (60 mL) and saturated saline (60 mL), dried by anhydrous sodium sulfate, filtered, concentrated under reduced pressure, and purified through a chromatographic column (eluent:petroleum ether:ethyl acetate=100:1~70:1), to obtain a light yellow solid product, i.e. a desirable compound, (3-formyl-1H-indol-1-yl)methyl tetradecanoate (Compound 32) (827 mg, yield: 77.8%).

The characteristic data of Compound 32 was: 1H NMR (400 MHz, CDCl3) δ 10.04 (s, 1H), 8.32 (d, J=7.0 Hz, 1H), 7.92 (s, 1H), 7.53 (d, J=7.6 Hz, 1H), 7.44-7.32 (m, 2H), 6.12 (s, 2H), 2.32 (t, J=7.5 Hz, 2H), 1.59 (s, 2H), 1.22 (d, J=22.3 Hz, 20H), 0.88 (t, J=6.8 Hz, 3H).

The purity of Compound 32 detected by HPLC was 98.67% at 254 nm and 99.35% at 214 nm, measured according to the normalization method of peak area.

Embodiment 27

Preparation of (3-(hydroxymethyl)-1H-indol-1-yl) methyl tetradecanoate (Compound 41)

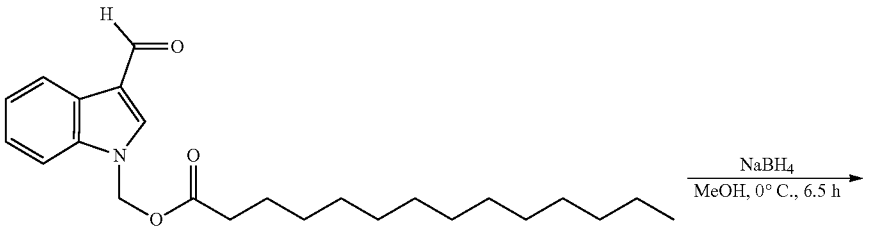

Compound 32

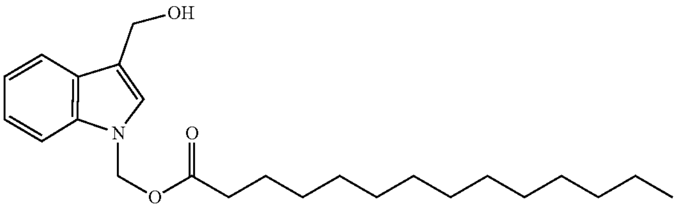

Compound 41

(3-formyl-1H-indol-1-yl)methyl tetradecanoate (Compound 32) (300 mg, 0.778 mmol) was dissolved in anhydrous methanol (6 ml). After the temperature was decreased to 0° C., sodium borohydride (29.4 mg, 0.778 mmol) was added, and the mixture was reacted for half an hour at 0° C. TLC (petroleum ether:ethyl acetate=3:1) detection showed that the reaction was completed. Saturated ammonia chloride aqueous solution (10 ml) was added to the reaction liquid, and the liquid was extracted by ethyl acetate (2×30 mL). Subsequently the organic phases were combined, washed by water (60 mL) and saturated saline (60 ml), dried by anhydrous sodium sulfate, filtered, and concentrated under reduced pressure. The obtained crude product was purified through prep-TCL (eluent:petroleum ether:ethyl acetate=2:1), and then a light yellow solid product, i.e. a desirable compound (3-(hydroxymethyl)-1H-indol-1-yl) methyl tetradecanoate (Compound 41) (130 mg, yield: 43.1%) was obtained.

The characteristic data of Compound 41 was: 1H NMR (400 MHz, DMSO) δ 7.61 (d, J=7.9 Hz, 1H), 7.53 (d, J=8.1 Hz, 1H), 7.34 (s, 1H), 7.19 (t, J=7.5 Hz, 1H), 7.09 (t, J=7.5 Hz, 1H), 6.17 (s, 2H), 4.90 (t, J=5.4 Hz, 1H), 4.61 (d, J=5.1 Hz, 2H), 2.26 (t, J=7.3 Hz, 2H), 1.45 (s, 2H), 1.19 (d, J=32.7 Hz, 20H), 0.85 (t, J=6.8 Hz, 3H).

The purity of Compound 41 detected by HPLC was 97.17% at 254 nm and 96.91% at 214 nm, measured according to the normalization method of peak area.

Figure 9:
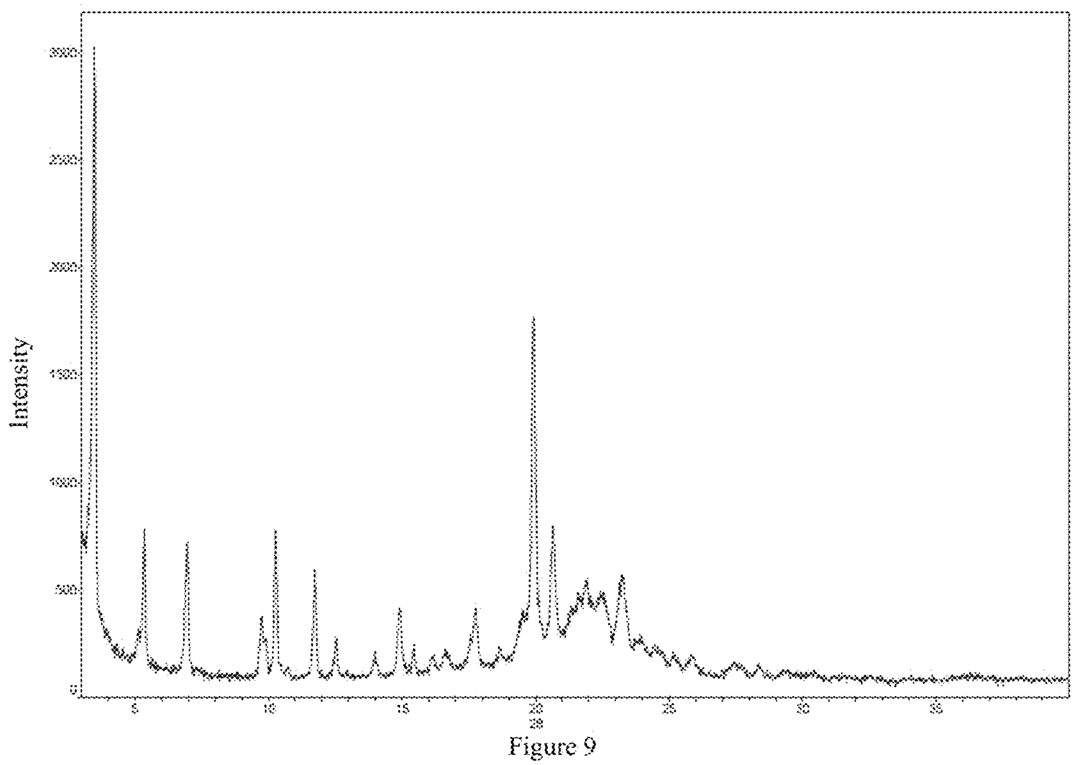
FIG. 9 depicts a XRPD pattern of Compound 41 in Embodiment 27.

The Compound 41 was recrystallized to obtain a pure crystal I of compound 41. The pure compound was detected by X-ray powder diffraction (XRPD), and the results were shown in the following Table 9 and FIG. 9.

TABLE 9

XRPD data of crystal I of compound 41

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 3.136 | 28.1507 | 216 | 2633 | 100.0 | 27335 | 100.0 | 0.172 |
| 2 | 5.220 | 16.9145 | 149 | 484 | 18.4 | 4016 | 14.7 | 0.137 |
| 3 | 6.660 | 13.2618 | 96 | 403 | 15.3 | 4903 | 17.9 | 0.201 |
| 4 | 9.117 | 9.6916 | 93 | 264 | 10.0 | 2540 | 9.3 | 0.159 |
| 5 | 9.844 | 8.9773 | 95 | 149 | 5.7 | 1587 | 5.8 | 0.176 |
| 6 | 10.189 | 8.6746 | 100 | 511 | 19.4 | 3752 | 13.7 | 0.122 |
| 7 | 10.519 | 8.4034 | 95 | 108 | 4.1 | 1558 | 5.7 | 0.239 |
| 8 | 11.454 | 7.7192 | 84 | 378 | 14.4 | 3254 | 11.9 | 0.143 |
| 9 | 12.023 | 7.3551 | 78 | 85 | 3.2 | 817 | 3.0 | 0.159 |
| 10 | 13.349 | 6.6271 | 73 | 55 | 2.1 | 793 | 2.9 | 0.239 |
| 11 | 14.129 | 6.2630 | 73 | 105 | 4.0 | 877 | 3.2 | 0.138 |
| 12 | 14.843 | 5.9633 | 79 | 132 | 5.0 | 1281 | 4.7 | 0.161 |
| 13 | 15.349 | 5.7680 | 90 | 82 | 3.1 | 947 | 3.5 | 0.191 |
| 14 | 15.879 | 5.5767 | 94 | 56 | 2.1 | 949 | 3.5 | 0.281 |
| 15 | 16.633 | 5.3255 | 88 | 102 | 3.9 | 884 | 3.2 | 0.144 |
| 16 | 18.409 | 4.8155 | 101 | 82 | 3.1 | 1643 | 6.0 | 0.332 |
| 17 | 19.326 | 4.5891 | 108 | 151 | 5.7 | 2842 | 10.4 | 0.312 |

TABLE 9-continued

| XRPD data of crystal I of compound 41 | | | | | | | | | |
|---|---|---|---|---|---|---|---|---|---|
| No. | 2θ | Interplanar distance (d) (Å) | Intensity of background signal (BG) | Peak Height | Relative peak Height % | Peak Area | Relative peak Area % | Full width at half maximum (FWHM) |
| 18 | 19.890 | 4.4601 | 174 | 1245 | 47.3 | 18560 | 67.9 | 0.247 |
| 19 | 20.519 | 4.3248 | 224 | 295 | 11.2 | 2659 | 9.7 | 0.149 |
| 20 | 21.565 | 4.1174 | 251 | 373 | 14.2 | 9491 | 34.7 | 0.421 |
| 21 | 22.479 | 3.9520 | 265 | 97 | 3.7 | 2039 | 7.5 | 0.348 |
| 22 | 23.083 | 3.8500 | 234 | 191 | 7.3 | 5592 | 20.5 | 0.485 |
| 23 | 23.643 | 3.7599 | 222 | 60 | 2.3 | 749 | 2.7 | 0.207 |

Embodiment 28

Preparation of (3-formyl-1H-indol-1-yl)methyl palmitate (Compound 33)

(1) Synthesis of Chloromethyl Palmitate

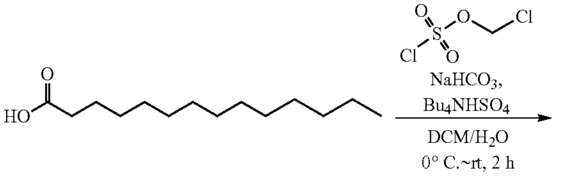

-continued

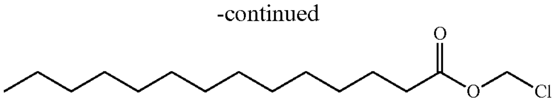

Palmitic acid (4.0 g, 15.599 mmol), sodium bicarbonate (5.241 g, 62.396 mmol), and tetrabutylammonium hydrogen sulfate (530 mg, 1.560 mmol) were dissolved in dichloromethane and water (60 mL, 1:1), the mixture was stirred for 5 mm at room temperature. Then, chloromethyl sulfurochloridate (3.080 g, 18.719 mmol) was added gradually at 0° C., and the mixture was reacted for 2 hours at room temperature. TLC (petroleum ether:ethyl acetate=5:1) showed that the reaction was completed. The reaction liquid was extracted by dichloromethane (2×50 mL). Subsequently, the organic phases were combined, washed by water (100 ml) and saturated saline (100 ml), dried by anhydrous sodium sulfate, filtered, concentrated under reduced pressure, and purified through chromatographic column (eluent:petroleum ether:ethyl acetate=100:1 to 80:1), to obtain a semi-transparent solid product, i.e. a desirable compound, chloromethyl palmitate (3.727 g, yield: 78.4%).

The characteristic data of chloromethyl palmitate was: 1H NMR (400 MHz, CDCl3) δ 5.70 (s, 2H), 2.38 (t, J=7.5 Hz, 2H), 1.72-1.54 (m, 2H), 1.33-1.23 (m, 24H), 0.88 (t, J=6.8 Hz, 3H).

(2) Synthesis of (3-formyl-1H-indol-1-yl)methyl palmitate (Compound 33)

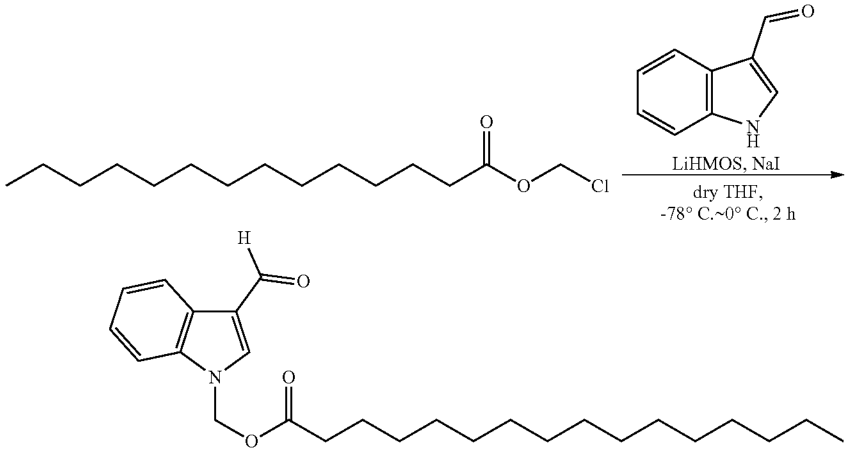

Compound 33

1H-indole-3-carboxaldehyde (400 mg, 2.755 mmol) and sodium iodide (41 mg, 0.275 mmol) were dissolved in anhydrous tetrahydrofuran (8 mL) under the argon atmosphere protection. After the temperature was decreased to −78° C., a solution of lithium bis(trimethylsilyl)amide (1M, 4.1 mL, 4.132 mmol) in tetrahydrofuran was dropwise dripped to the reaction liquid, and the liquid was reacted for 1 hour at −78° C. Subsequently, a solution of chloromethyl palmitate (1.680 g, 5.511 mmol) in tetrahydrofuran (8 mL) was dripped to the reaction liquid, and the liquid was reacted for 2 hours at −78° C. TLC (petroleum ether:ethyl acetate=5:1) showed that the reaction was completed. Saturated ammonia chloride aqueous solution (20 mL) was added to the reaction liquid, and the reaction liquid was extracted by ethyl acetate (2×40 mL). Subsequently, the organic phases were combined, washed by water (80 mL) and saturated saline (80 mL), dried by anhydrous sodium sulfate, filtered, concentrated under reduced pressure, and purified through a chromatographic column (eluent:petroleum ether:ethyl acetate=100:1~80:1), to obtain a white solid product, i.e. a desirable compound, (3-formyl-1H-indol-1-yl)methyl palmitate (Compound 33) (697 mg, yield: 61.2%).

The characteristic data of Compound 33 was: 1H NMR (400 MHz, CDCl3) δ 10.04 (s, 1H), 8.32 (d, J=6.8 Hz, 1H), 7.92 (s, 1H), 7.53 (d, J=7.5 Hz, 1H), 7.37 (td, J=13.8, 6.0 Hz, 2H), 6.12 (s, 2H), 2.32 (t, J=7.5 Hz, 2H), 1.58 (s, 8H), 1.22 (d, J=24.3 Hz, 24H), 0.88 (t, J=6.8 Hz, 3H).

The purity of Compound 33 detected by HPLC was 97.69% at 254 nm and 98.46% at 214 nm, measured according to the normalization method of peak area.

Embodiment 29

Preparation of (3-(hydroxymethyl)-1H-indol-1-yl) methyl palmitate (Compound 42)

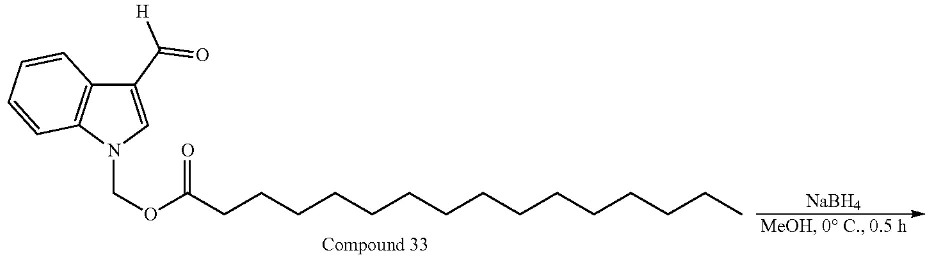

Compound 33

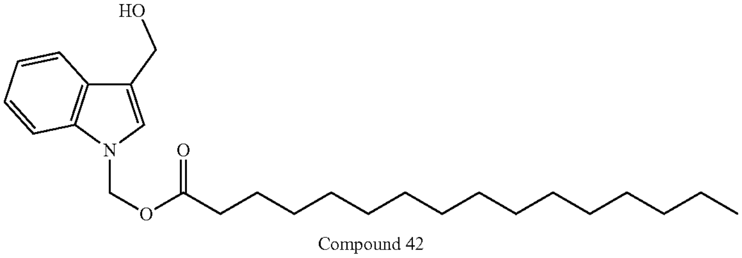

Compound 42

(3-formyl-1H-indol-1-yl)methyl palmitate (Compound 33) (300 mg, 0.725 mmol) was dissolved in anhydrous methanol (10 ml) and tetrahydrofuran (5 ml). After the temperature was decreased to 0° C., sodium borohydride (27 mg, 0.725 mmol) was added to the mixture, and the mixture was reacted for half an hour at 0° C. TLC (petroleum ether:ethyl acetate=3:1) detection showed that the reaction was completed. Saturated ammonia chloride aqueous solution (10 mL) was added to the reaction liquid, and the liquid was extracted by ethyl acetate (2×30 mL). Subsequently, the organic phases were combined, washed by water (60 mL) and saturated saline (60 ml), dried by anhydrous sodium sulfate, filtered, and concentrated under reduced pressure. The obtained crude product was purified through prep-TCL (eluent:petroleum ether:ethyl acetate=2:1), and then a white solid product, i.e. a desirable compound, (3-(hydroxymethyl)-1H-indol-1-yl)methyl palmitate (Compound 42) (250 mg, yield: 83.0%) was obtained.

The characteristic data of Compound 42 was: 1H NMR (400 MHz, DMSO) δ 7.61 (d, J=7.9 Hz, 1H), 7.53 (d, J=8.3 Hz, 1H), 7.34 (s, 1H), 7.19 (t, J=7.1 Hz, 1H), 7.09 (t, J=7.0 Hz, 1H), 6.17 (s, 2H), 4.90 (t, J=5.4 Hz, 1H), 4.61 (d, J=5.1

Hz, 2H), 2.26 (t, J=7.3 Hz, 2H), 1.45 (s, 2H), 1.19 (d, J=33.6 Hz, 24H), 0.85 (t, J=6.8 Hz, 3H).

The purity of Compound 42 detected by HPLC was 97.87% at 254 nm and 98.43% at 214 nm, measured according to the normalization method of peak area.

Embodiment 30

Preparation of (3-formyl-1H-indol-1-yl)methyl 2,5,8,11,14-pentaoxahexadecan-16-oate (Compound 34)

(1) Synthesis of chloromethyl 2,5,8,11,14-pentaoxahexadecan-16-oate

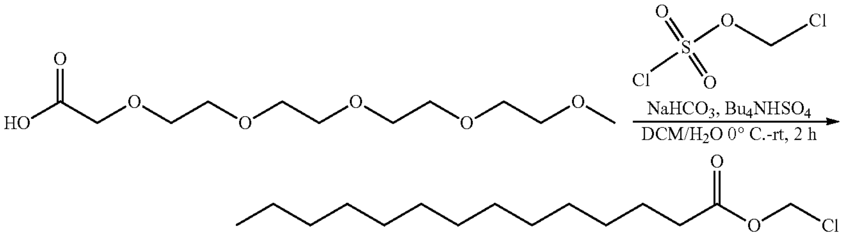

2,5,8,11,14-pentaoxahexadecan-16-oic acid (1.6 g, 6.008 mmol), sodium bicarbonate (2.019 g, 24.032 mmol), and tetrabutylammonium hydrogen sulfate (204 mg, 0.600 mmol) were dissolved in dichloromethane and water (50 mL, 1:1), and the mixture was stirred for 5 min at room temperature. Subsequently, chloromethyl sulfurochloridate (1.189 g, 7.210 mmol) was gradually added to the reaction liquid at 0° C., and the reaction liquid was reacted for 2 hours at room temperature. Dichloromethane was used for performing extraction (2×50 mL). The organic phases were combined, washed by water (100 ml) and saturated saline (100 ml), dried by anhydrous sodium sulfate, filtered, concentrated under reduced pressure to obtain a yellow oily product, i.e. a desirable compound, chloromethyl 2,5,8,11,14-pentaoxahexadecan-16-oate (1.2 g, a crude product).

The characteristic data of chloromethyl 2,5,8,11,14-pentaoxahexadecan-16-oate was: 1H NMR (400 MHz, CDCl3) δ 5.76 (s, 2H), 4.25 (s, 2H), 3.78-3.74 (m, 2H), 3.72-3.65 (m, 12H), 3.55 (dd, J=5.6, 3.6 Hz, 2H), 3.39 (d, J=2.8 Hz, 3H).

(2) Synthesis of (3-formyl-1H-indol-1-yl)methyl 2,5,8,11,14-pentaoxahexadecan-16-oate (Compound 34)

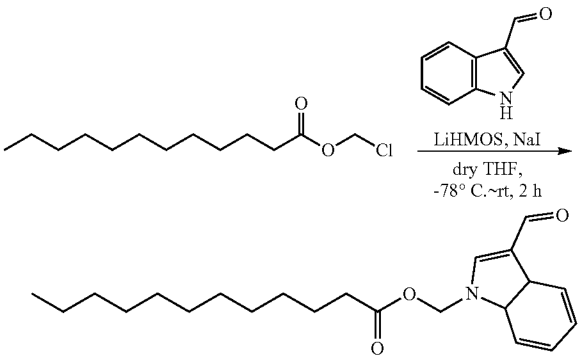

Compound 34

1H-indole-3-carboxaldehyde (503 mg, 3.812 mmol), sodium iodide (52 mg, 0.347 mmol), chloromethyl 2,5,8,11,14-pentaoxahexadecan-16-oate (1.2 g, 3.812 mmol), and triethylamine (1.052 mg, 10.398 mmol) were dissolved in N,N-dimethylformamide (20 mL), and the mixture was reacted for 12 hours at 30° C. After adding 4-dimethylaminopyridine (42 mg, 0.347 mmol), the mixture was reacted for 12 hours at 30° C. LCMS showed that the reaction was completed. Saturated ammonia chloride aqueous solution (20 mL) was added to the reaction liquid, and the reaction liquid was extracted by ethyl acetate (2×60 mL). Subsequently, the organic phases were combined, washed by water (120 mL) and saturated saline (120 mL), dried by anhydrous sodium sulfate, filtered, concentrated under reduced pressure, and purified through a preparative HPLC, to obtain a yellow solid product, i.e. a desirable compound, (3-formyl-1H-indol-1-yl)methyl 2,5,8,11,14-pentaoxahexadecan-16-oate (Compound 34) (320 mg, yield: 21.8%).

The characteristic data of Compound 34 was: 1H NMR (400 MHz, CDCl3) δ 10.04 (s, 1H), 8.31 (d, J=6.9 Hz, 1H), 7.95 (s, 1H), 7.54 (d, J=7.4 Hz, 1H), 7.43-7.32 (m, 2H), 6.20 (s, 2H), 4.18 (s, 2H), 3.70-3.51 (m, 16H), 3.36 (s, 3H).

The purity of Compound 34 detected by HPLC was 99.32% at 254 nm and 99.38% at 214 nm, measured according to the normalization method of peak area.

Embodiment 31

Preparation of (3-formyl-1H-indol-1-yl)methyl 2-acetoxybenzoate (Compound 35)

(1) Synthesis of chloromethyl 2-acetoxybenzoate

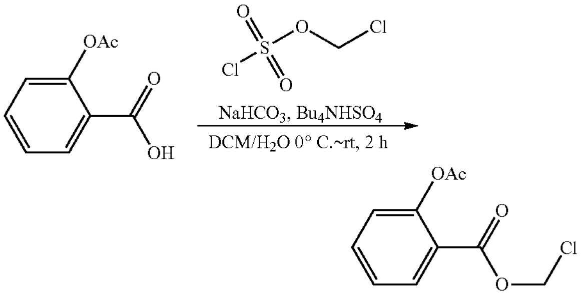

2-acetoxybenzoic acid (3.0 g, 15.599 mmol), sodium bicarbonate (5.595 g, 66.604 mmol), and tetrabutylammonium hydrogen sulfate (565 mg, 1.665 mmol) were dissolved in dichloromethane and water (40 mL, 1:1), and the mixture was stirred for 5 min at room temperature. Subsequently, chloromethyl sulfonyl chloride (3.297 g, 19.982 mmol) was gradually added to the reaction liquid at 0° C., and the reaction liquid was reacted for 2 hours at room temperature. TLC (petroleum ether:ethyl acetate=5:1) showed that the reaction was completed. Dichloromethane (2×40 mL) was used for performing extraction. The organic phases were combined, washed by water (80 ml) and saturated saline (80 ml), dried by anhydrous sodium sulfate, filtered, concentrated under reduced pressure, and purified through a chromatographic column (eluent:petroleum ether: ethyl acetate=100:1 to 80:1), to obtain a colorless oily product, i.e. a desirable compound, chloromethyl 2-acetoxybenzoate (3.0 g, yield: 78.8%).

The characteristic data of chloromethyl 2-acetoxybenzoate was: 1H NMR (400 MHz, CDCl3) δ 8.06 (dd, J=7.9, 1.6 Hz, 1H), 7.62 (td, J=7.9, 1.6 Hz, 1H), 7.41-7.29 (m, 1H), 7.22-7.07 (m, 1H), 5.90 (s, 2H), 2.38 (s, 3H).

(2) Synthesis of (3-formyl-1H-indol-1-yl)methyl 2-acetoxybenzoate (Compound 35)

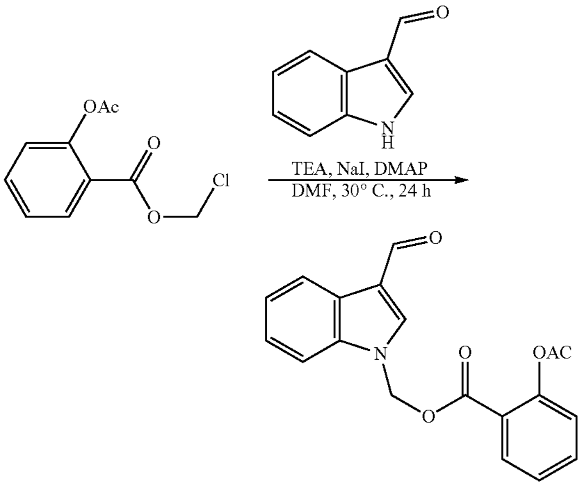

Compound 35

1H-indole-3-carboxaldehyde (800 mg, 5.511 mmol), sodium iodide (83 mg, 0.551 mmol), 4-dimethylaminopyridine (67 mg, 0.551 mmol), chloromethyl 2-acetoxybenzoate (2.520 g, 11.022 mmol), and triethylamine (1.673 mg, 16.533 mmol) were dissolved in N, N-dimethylformamide (32 mL), and the mixture was reacted for 24 hours at 30° C. TLC (petroleum ether/ethyl acetate=1.5:1) showed that the reaction was completed. Saturated ammonia chloride aqueous solution (20 mL) was added to the reaction liquid, and the reaction liquid was extracted by ethyl acetate (2×50 mL). Subsequently, the organic phases were combined, washed by water (100 mL) and saturated saline (100 mL), dried by anhydrous sodium sulfate, filtered, concentrated under reduced pressure, and purified through a preparative HPLC, to obtain a white solid product, i.e. a desirable compound, (3-formyl-1H-indol-1-yl)methyl 2-acetoxybenzoate (Compound 35) (233 mg, yield: 12.4%).

The characteristic data of Compound 35 was: 1H NMR (400 MHz, CDCl3) δ 10.07 (s, 1H), 8.33 (d, J=7.3 Hz, 1H), 8.13-7.86 (m, 2H), 7.58 (ddd, J=7.8, 4.6, 1.7 Hz, 2H), 7.40 (ddd, J=15.1, 13.9, 6.9 Hz, 2H), 7.29 (t, J=8.1 Hz, 1H), 7.09 (d, J=8.1 Hz, 1H), 6.33 (s, 2H), 2.14 (s, 3H).

The purity of Compound 35 detected by HPLC was 99.7% at 254 nm and 99.63% at 214 nm, measured according to the normalization method of peak area.

Figure 10:
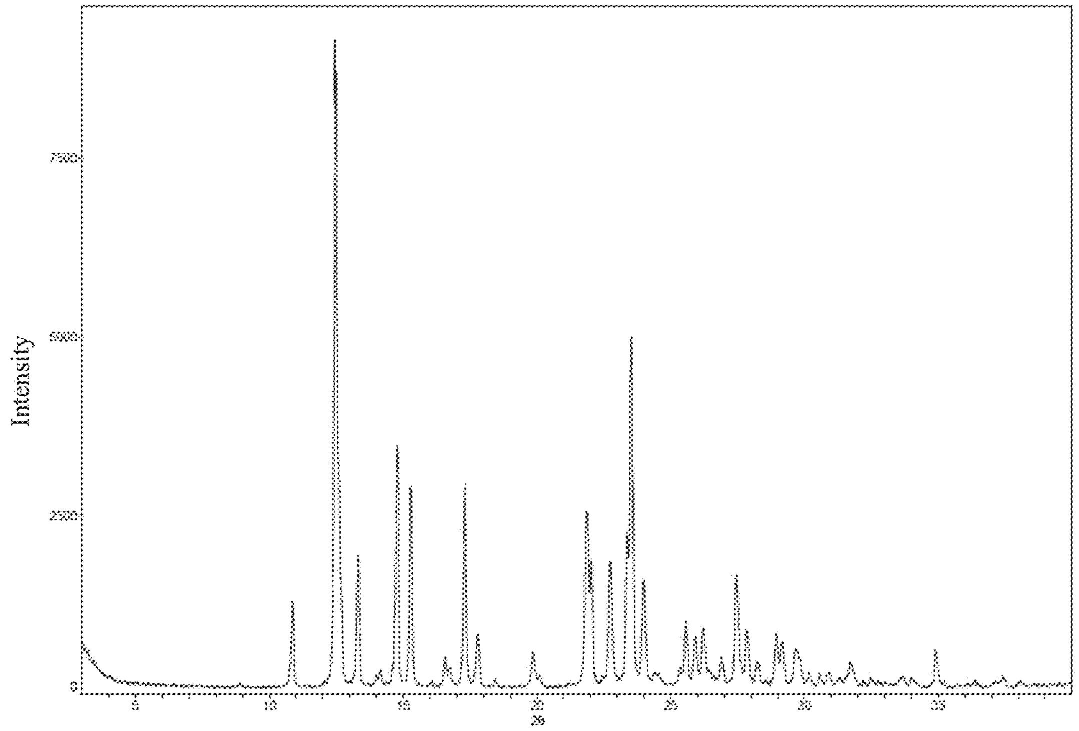
FIG. 10 depicts a XRPD pattern of Compound 35 in Embodiment 31.

The Compound 35 was recrystallized to obtain a pure crystal I of Compound 35. The pure compound was detected by X-ray powder diffraction (XRPD), and the results were shown in the following Table 10 and FIG. 10.

TABLE 10

XRPD data of crystal I of Compound 35

| No. | 2θ | Interplanar distance (d) (Å) | Intensity of background signal (BG) | Peak Height | Relative peak Height % | Peak Area | Relative peak Area % | Full width at half maximum (FWHM) |
|---|---|---|---|---|---|---|---|---|
| 1 | 8.845 | 9.9890 | 83 | 68 | 0.8 | 641 | 0.9 | 0.156 |
| 2 | 10.833 | 8.1599 | 86 | 1206 | 13.3 | 8752 | 12.0 | 0.120 |
| 3 | 12.449 | 7.1044 | 130 | 9050 | 100.0 | 73025 | 100.0 | 0.134 |
| 4 | 13.287 | 6.6580 | 144 | 1792 | 19.8 | 10737 | 14.7 | 0.099 |
| 5 | 14.125 | 6.2649 | 128 | 206 | 2.3 | 1625 | 2.2 | 0.131 |
| 6 | 14.748 | 6.0016 | 120 | 3350 | 37.0 | 24331 | 33.3 | 0.120 |
| 7 | 15.258 | 5.8022 | 117 | 2777 | 30.7 | 18465 | 25.3 | 0.110 |
| 8 | 16.080 | 5.5074 | 103 | 60 | 0.7 | 289 | 0.4 | 0.080 |
| 9 | 16.555 | 5.3505 | 112 | 391 | 4.3 | 3198 | 4.4 | 0.135 |
| 10 | 16.716 | 5.2991 | 119 | 236 | 2.6 | 2497 | 3.4 | 0.175 |
| 11 | 17.278 | 5.1280 | 100 | 2827 | 31.2 | 20245 | 27.7 | 0.119 |
| 12 | 17.766 | 4.9884 | 111 | 718 | 7.9 | 6056 | 8.3 | 0.140 |
| 13 | 18.430 | 4.8102 | 95 | 95 | 1.0 | 468 | 0.6 | 0.082 |
| 14 | 19.813 | 4.4773 | 84 | 490 | 5.4 | 5881 | 8.1 | 0.199 |
| 15 | 20.084 | 4.4174 | 83 | 165 | 1.8 | 2021 | 2.8 | 0.203 |
| 16 | 21.839 | 4.0663 | 141 | 2409 | 26.6 | 23426 | 32.1 | 0.161 |
| 17 | 22.715 | 3.9114 | 181 | 1664 | 18.4 | 13678 | 18.7 | 0.136 |
| 18 | 23.512 | 3.7807 | 203 | 4802 | 53.1 | 46107 | 63.1 | 0.159 |
| 19 | 23.963 | 3.7105 | 169 | 1427 | 15.8 | 12233 | 16.8 | 0.142 |
| 20 | 24.390 | 3.6464 | 174 | 116 | 1.3 | 1651 | 2.3 | 0.236 |
| 21 | 25.342 | 3.5116 | 132 | 251 | 2.8 | 2119 | 2.9 | 0.140 |

TABLE 10-continued

| XRPD data of crystal I of Compound 35 | | | | | | | | |
|---|---|---|---|---|---|---|---|---|
| No. | 2θ | Interplanar distance (d) (Å) | Intensity of background signal (BG) | Peak Height | Relative peak Height % | Peak Area | Relative peak Area % | Full width at half maximum (FWHM) |
| 22 | 25.556 | 3.4827 | 132 | 882 | 9.7 | 7362 | 10.1 | 0.138 |
| 23 | 25.890 | 3.4385 | 171 | 626 | 6.9 | 5530 | 7.6 | 0.146 |
| 24 | 26.200 | 3.3986 | 181 | 751 | 8.3 | 8784 | 12.0 | 0.194 |
| 25 | 26.869 | 3.3154 | 200 | 312 | 3.4 | 1976 | 2.7 | 0.105 |
| 26 | 27.431 | 3.2488 | 183 | 1476 | 16.3 | 12428 | 17.0 | 0.139 |
| 27 | 27.821 | 3.2041 | 169 | 732 | 8.1 | 5909 | 8.1 | 0.134 |
| 28 | 28.211 | 3.1607 | 172 | 302 | 3.3 | 1967 | 2.7 | 0.108 |
| 29 | 28.928 | 3.0840 | 145 | 698 | 7.7 | 7376 | 10.1 | 0.175 |
| 30 | 29.126 | 3.0635 | 148 | 574 | 6.3 | 6748 | 9.2 | 0.195 |
| 31 | 29.651 | 3.0104 | 129 | 519 | 5.7 | 7765 | 10.6 | 0.248 |
| 32 | 30.142 | 2.9625 | 128 | 156 | 1.7 | 1139 | 1.6 | 0.121 |
| 33 | 30.551 | 2.9237 | 118 | 152 | 1.7 | 1013 | 1.4 | 0.110 |
| 34 | 30.875 | 2.8937 | 116 | 192 | 2.1 | 1700 | 2.3 | 0.147 |
| 35 | 31.289 | 2.8564 | 118 | 121 | 1.3 | 1108 | 1.5 | 0.152 |
| 36 | 31.697 | 2.8205 | 120 | 335 | 3.7 | 4046 | 5.5 | 0.200 |
| 37 | 32.458 | 2.7561 | 126 | 91 | 1.0 | 488 | 0.7 | 0.089 |
| 38 | 32.756 | 2.7317 | 126 | 49 | 0.5 | 244 | 0.3 | 0.082 |
| 39 | 33.661 | 2.6603 | 118 | 112 | 1.2 | 1379 | 1.9 | 0.204 |
| 40 | 33.962 | 2.6375 | 107 | 104 | 1.1 | 1639 | 2.2 | 0.261 |
| 41 | 34.888 | 2.5695 | 91 | 523 | 5.8 | 4703 | 6.4 | 0.149 |
| 42 | 36.364 | 2.4686 | 87 | 102 | 1.1 | 1401 | 1.9 | 0.227 |
| 43 | 37.402 | 2.4024 | 87 | 168 | 1.9 | 2601 | 3.6 | 0.256 |
| 44 | 38.045 | 2.3633 | 88 | 94 | 1.0 | 1685 | 2.3 | 0.297 |

Embodiment 32

The compounds prepared from the above embodiments were subjected to an activity test.

1. Method.

A mouse model with ear AD-like symptoms induced by calcipotriol (MC903) was used to investigate these compounds in terms of the treatment activity for AD.

Referring to the Patent with a publication number of CN 110368386 A, a mouse model induced by MC903 (Calcipotriene) was prepared, wherein both ears of the BALB/c mouse model were applied with MC903, MC903+indole-3-aldehyde (IAId), or MC903+the compound prepared from the embodiments for 11 consecutive days, respectively, and total serum IgE levels, ear thicknesses, and weight loss in relative to the weight at the beginning of the experiment were tested at the end of the experiment. Due to a large number of drugs to be tested, therapeutic effects of the drugs were evaluated in two batches.

2. Results

The data shown in the results were average values ±SD of five independently repeated trials. Significance analysis was performed using Mann-Whitney test on the differences of corresponding parameters of the mice with the treatment group (MC903+ethanol (EtOH)), which was only administrated with MC903, wherein * indicated $P<0.05$,  indicated $P<0.01$; * indicated $P<0.001$.

2.1 First Batch of Experiments

Figure 11:
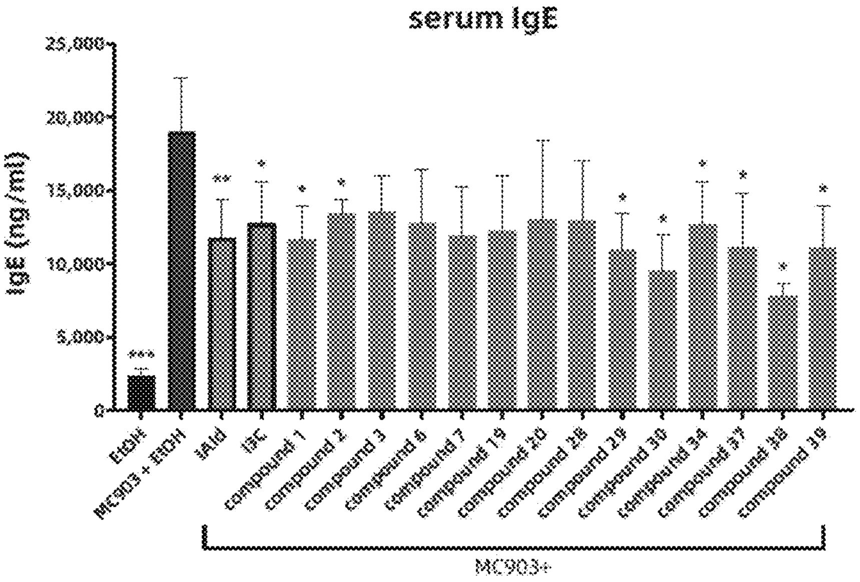
FIG. 11 depicts schematic diagrams of the total serum IgE levels of the mice in the first batch of experiments in Embodiment 32.
Figure 12:
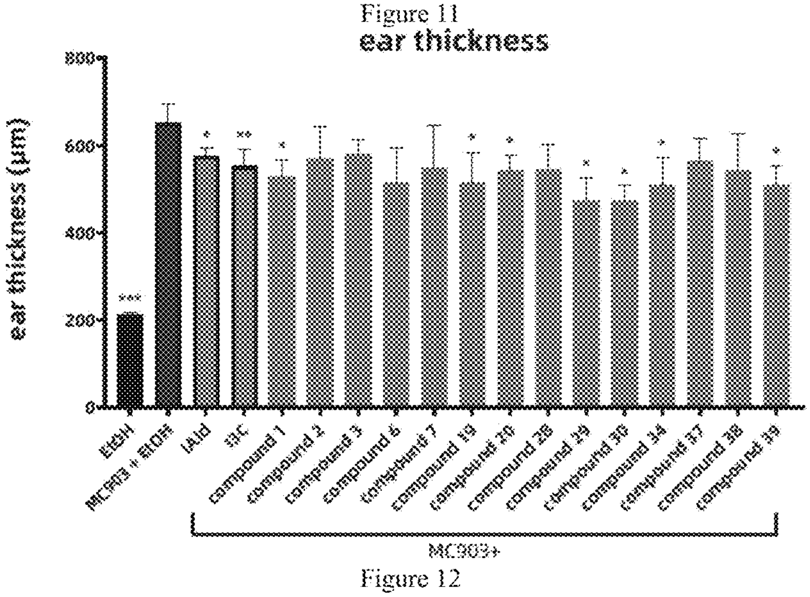
FIG. 12 depicts schematic diagrams of the ear thicknesses of the mice in the first batch of experiments in Embodiment 32.
Figure 13:
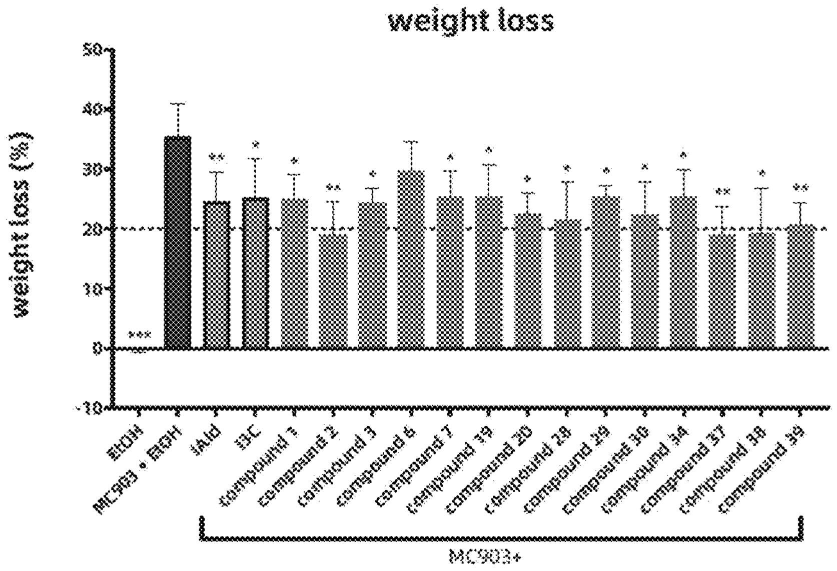
FIG. 13 depicts schematic diagrams of the weight loss of the mice in the first batch of experiments in Embodiment 32.

In this batch of experiments, the dosage of MC903, a drug for constructing the models, was 6.9 nmol/mouse every day, and the experimental results of Compounds 1, 2, 3, 6, 7, 19, 20, 28, 29, 30, 34, 37, 38, and 39 in this batch were shown in FIGS. 11 to 13.

Figure 14:
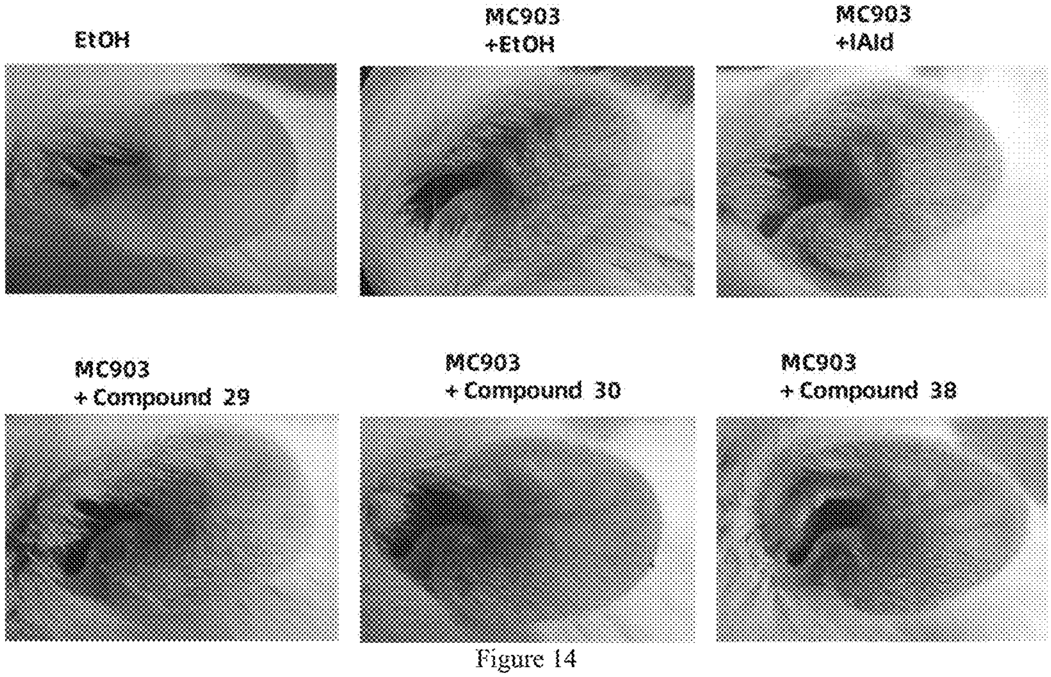
FIG. 14 depicts photographs of ears of representative mice after administration of different drugs in the first batch of experiments in Embodiment 32.
Figure 15:
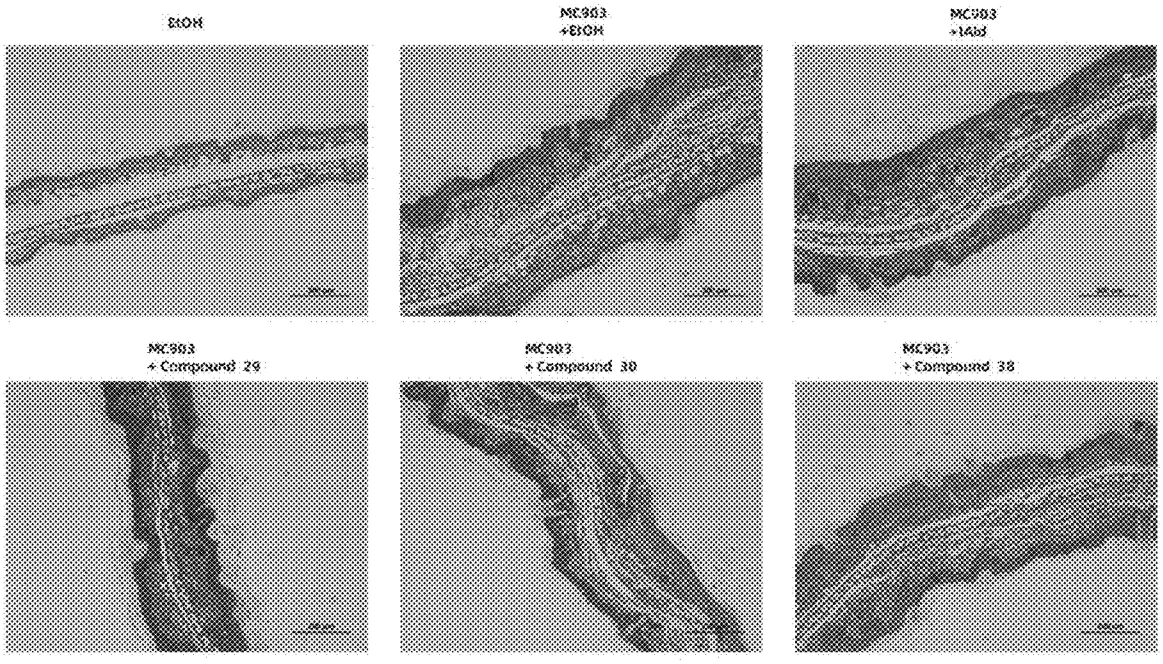
FIG. 15 depicts HE (hematoxylin-eosin) staining patterns of ear tissues of representative mice after administration of different drugs in the first batch of experiments in Embodiment 32.

FIG. 11 shows the total serum IgE levels of the mice after the mice were administrated with different drugs. FIG. 12 shows the ear thicknesses of the mice after the mice were administrated with different drugs. FIG. 13 shows the weight loss of the mice in relative to the weight at the beginning of the experiments after the mice were administrated with different drugs. FIG. 14 shows photographs of ear thicknesses of the representative mice after the mice were administrated with different drugs. FIG. shows hematoxylin and eosin (HE) staining images of ear tissues of the representative mice after the mice were administrated with different drugs. EtOH group was a Blank control group, which was only administrated with ethanol. MC903+ EtOH group was a model control group, which was administrated with Calcipotriene and ethanol. The remaining groups were the groups which were administered with MC903 to construct the model, and then administrated with different drugs. Indole-3-aldehyde (IAId) group was the group administered with IAId, indole-3-methanol (I3C) group was the group administered with I3C. The other compound groups were the groups administered with corresponding compounds.

It can be seen from the Figures that, the total serum IgE levels, ear thicknesses, and the weight loss in relative to the weight at the beginning of the experiment of the mice in the model control group (MC903+ EtOH) had significant differences compared with the Blank control group (EtOH) ($P<0.001$), indicating that the modeling was succeed. In both IAId group and I3C group, the total serum IgE levels and ear thicknesses of the mice were significantly reduced ($P<0.05$ or $P<0.01$), and all compounds had positive effects on the total serum IgE levels, ear thicknesses and the weight loss of the mice. Specifically, in terms of reducing the total serum IgE levels of the mice, Compounds 1, 2, 29, 30, 34, 37, 38, and 39 had statistically significant difference compared with that of the model control group, and in particular, Compounds 30 and 38 showed excellent effects in reducing the total serum IgE level of the mice. In terms of reducing ear thicknesses of the mice, Compounds 1, 19, 20, 29, 30, 34, and 39 had statistically significant difference compared with that of the model control group, and in particular, Compounds 29 and 30 showed excellent effects in reducing the ear thicknesses of the mice. Combined with the ear inflammation and the results of tissue HE staining of the mice, it is found that Compounds 29, 30, and 38 had significant therapeutic effects on AD-like symptoms in the ear of mice.

2.2 Second Batch of Experiments

It was found that in the first batch of experiments, the survival status of the mice was greatly affected by the drug for constructing the model, i.e., MC903, which was manifested as a significant weight loss (FIG. 13). Therefore, in the second batch of drug tests, the dosage of MC903 was decreased to 5 nmol/mouse every day, and the test period was reduced to 9 days. Finally, the survival status of mice were greatly improved (FIG. 18), consistent with expectation.

The experimental results of Compounds 30, 38 4, 5, 9, 21, 22, 23, 24, 26, 27, 31, 32, 33, 35, 40, 41, 42, 8, and 29 in this batch of experiments were shown in FIG. 16 to 20.

Figure 16:
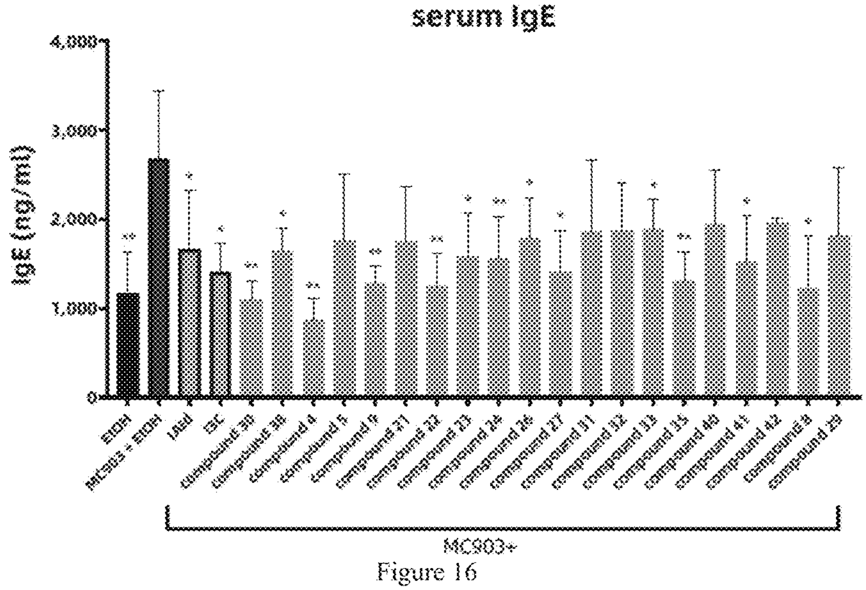
FIG. 16 depicts schematic diagrams of the total serum IgE levels of the mice in the second batch of experiments in Embodiment 32.
Figure 17:
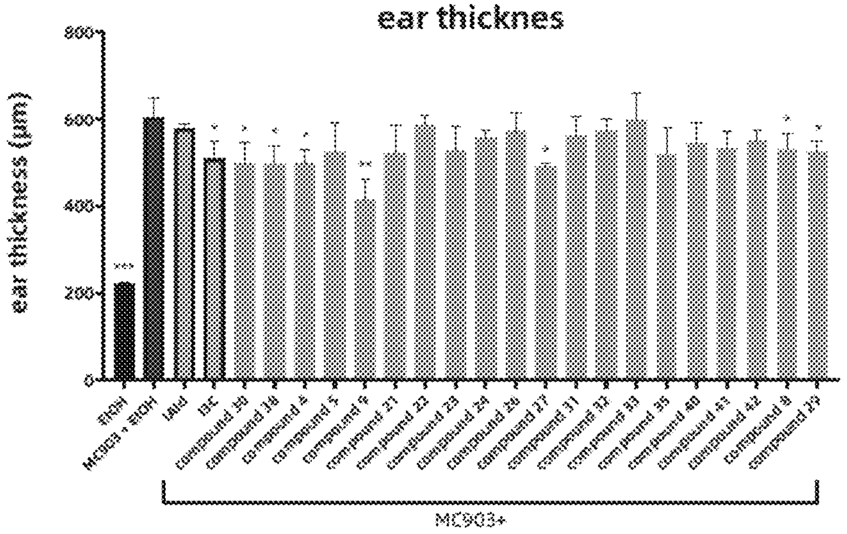
FIG. 17 depicts schematic diagrams of the ear thickness of the mice in the second batch of experiments in Embodiment 32.
Figure 18:
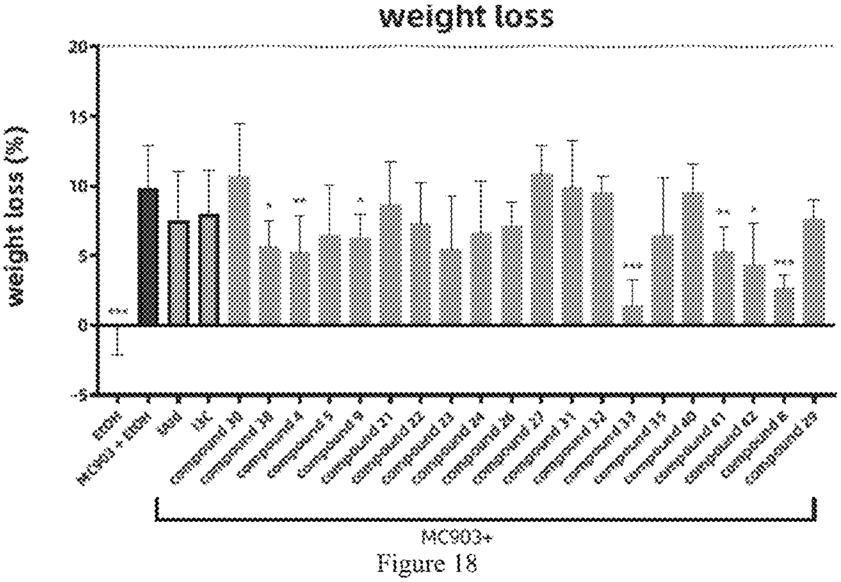
FIG. 18 depicts schematic diagrams of the weight loss of the mice in the second batch of experiments in Embodiment 32.
Figure 19:
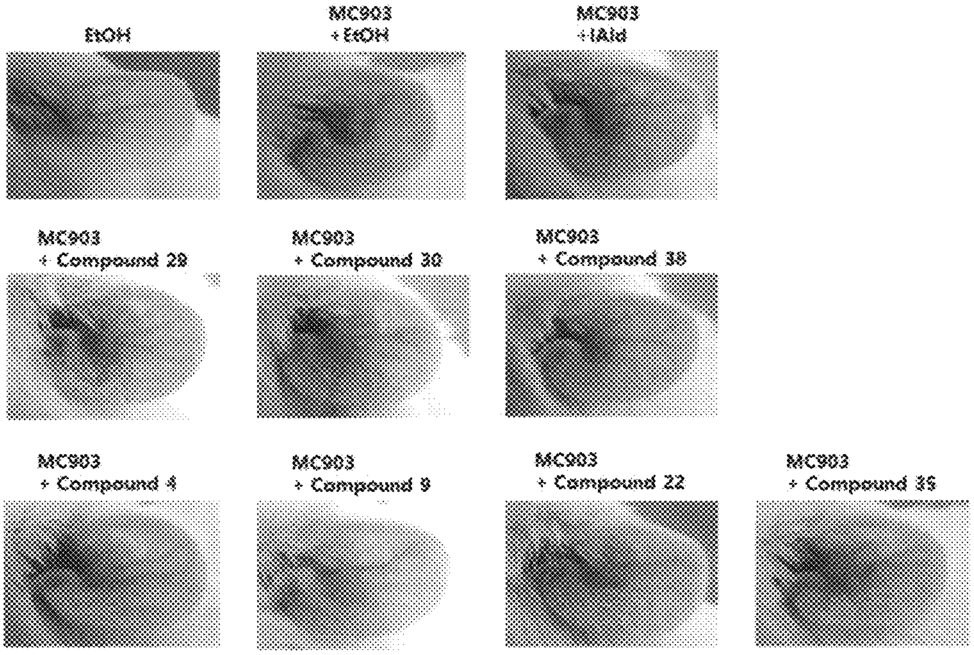
FIG. 19 depicts photographs of ears of representative mice after administration of different drugs in the second batch of experiments in Embodiment 32.
Figure 20:
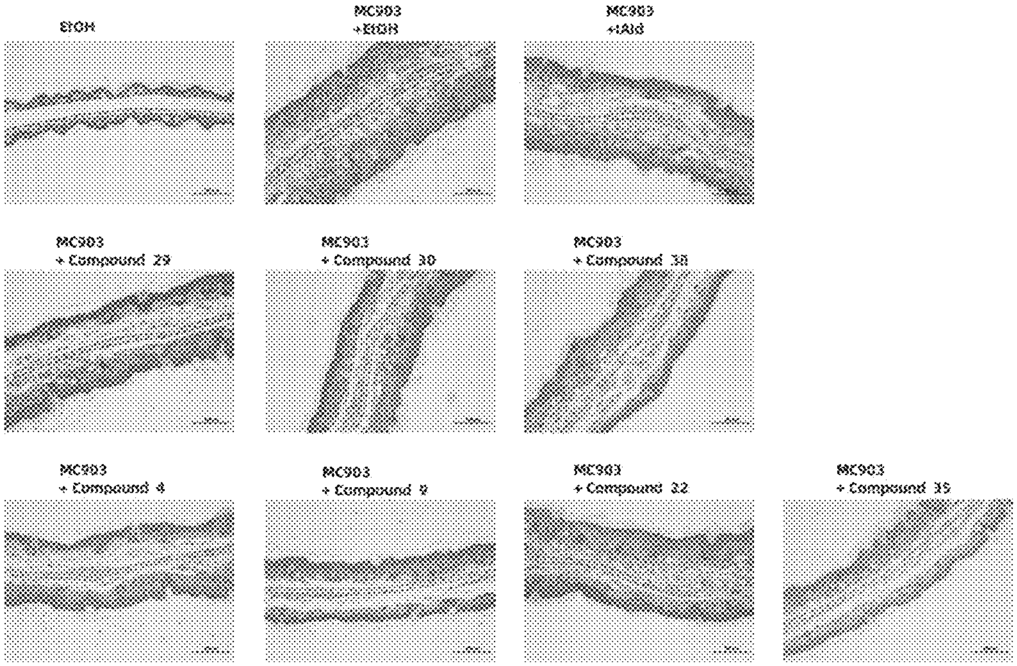
FIG. 20 depicts HE staining patterns of ear tissues of representative mice after administration of different drugs in the second batch of experiments in Embodiment 32.

FIG. 16 shows the total serum IgE levels of mice after the mice were administrated with different drugs. FIG. 17 shows the ear thicknesses of the mice after the mice were administrated with different drugs. FIG. 18 shows the weight loss of the mice in relative to the weight at the beginning of the experiments after the mice were administrated with different drugs. FIG. 19 shows photographs of ear thicknesses of the representative mice after the mice were administrated with different drugs. FIG. 20 shows hematoxylin and eosin (HE) staining images of ear tissues of the representative mice after the mice were administrated with different drugs. EtOH group was a Blank control group, which was only administrated with ethanol. MC903+ EtOH group was a model control group, which was administrated with Calcipotriene and ethanol. The remaining groups were the groups which were administered with MC903 to construct the model, and then administered with different drugs. Indole-3-aldehyde (IAld) group was the group administered with IAld. Indole-3-methanol (I3C) group was the group administered with I3C. The other compound groups were the groups administered with corresponding compounds.

It can be seen from the Figures that the total serum IgE level, ear thicknesses, and the weight loss in relative to the weight at the beginning of the experiment of the mice in the model control group (MC903+ EtOH) had significant differences compared with the Blank control group (EtOH) ($P<0.01$ or $P<0.001$), indicating that modeling was succeed. In terms of reducing the total serum IgE levels of the mice, Compounds 30, 38, 4, 9, 22, 23, 24, 26, 27, 33, 35, 41, and 8 had statistically significant difference compared with that of the model control group, and in particular, Compounds 30, 4, 9, 22, and 35 showed excellent effects in reducing the total serum IgE levels of the mice. In terms of reducing ear thicknesses of the mice, Compounds 30, 38, 4, 9, 27, 8, and 29 had statistically significant difference compared with that of the model control group, and in particular, Compound 9 showed excellent effects in reducing the ear thicknesses of the mice. Combined with the ear inflammation and the results of tissue HE staining of the mice, and in consideration of the parameters of multiple experiments and tests, the drugs having therapeutic effects on AD-like symptoms in the ear of mice were screened to be Compounds 4, 9, 29, 30, 38, 22, and 35.

Embodiment 33

Optimum effective concentration in Treatment of AD-like symptoms

1. Method.

The above screened compounds having therapeutic effect on AD-like symptoms were selected to further determine the optimum effective concentration.

Referring to the animal model method in the Embodiment 32, dosages of drugs for each group were determined according to the table below, and the optimal effective concentration in treatment of AD-like symptoms was explored by comparing the differences in ear thicknesses, the total serum IgE levels and the weight loss of the mice with those of the treatment group only administrated with MC903.

TABLE 11

Groups and dosages for administration

| Group | Treatment and Dosage |
|---|---|
| #1 | EtOH (Blank) |
| #2 | MC903 + EtOH (for constructing Models) |
| #3 | MC903 + IAld (10 μg/ml) |
| #4 | MC903 + IAld (100 μg/ml) |
| #5 | MC903 + IAld (1000 μg/ml) |
| #6 | MC903 + I3C (10 μg/ml) |
| #7 | MC903 + I3C (100 μg/ml) |
| #8 | MC903 + I3C (1000 μg/ml) |
| #9 | MC903 + Compound 4 (10 μg/ml) |
| #10 | MC903 + Compound 4 (1000 μg/ml) |
| #11 | MC903 + Compound 9 (10 μg/ml) |
| #12 | MC903 + Compound 9 (100 μg/ml) |
| #13 | MC903 + Compound 9 (1000 μg/ml) |
| #14 | MC903 + Compound 22 (10 μg/ml) |
| #15 | MC903 + Compound 22 (1000 μg/ml) |
| #16 | MC903 + Compound 35 (10 μg/ml) |
| #17 | MC903 + Compound 35 (100 μg/ml) |
| #18 | MC903 + Compound 35 (1000 μg/ml) |
| #19 | MC903 + Compound 29 (10 μg/ml) |
| #20 | MC903 + Compound 29 (100 μg/ml) |
| #21 | MC903 + Compound 29 (1000 μg/ml) |
| #22 | MC903 + Compound 30 (10 μg/ml) |
| #23 | MC903 + Compound 30 (100 μg/ml) |
| #24 | MC903 + Compound 30 (1000 μg/ml) |
| #25 | MC903 + Compound 38 (10 μg/ml) |
| #26 | MC903 + Compound 38 (100 μg/ml) |
| #27 | MC903 + Compound 38 (1000 μg/ml) |

Note:
the above administration was performed by topical application.

2. Results.

Figure 21:
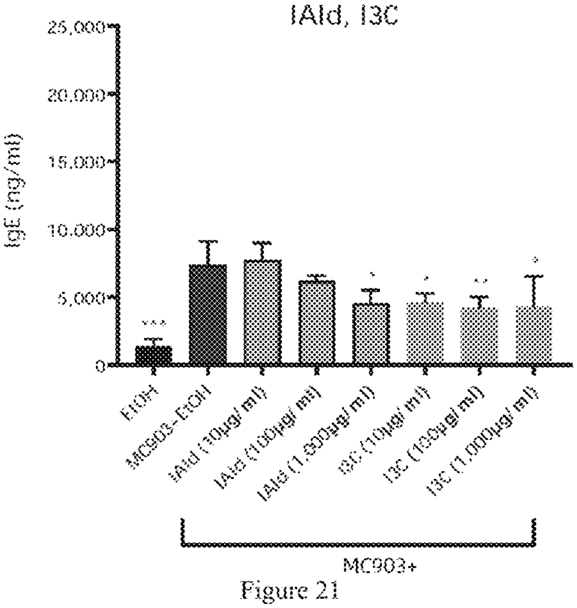
FIG. 21 depicts a schematic diagram of the total serum IgE levels of the mice in each group in Embodiment 33.
Figure 22:
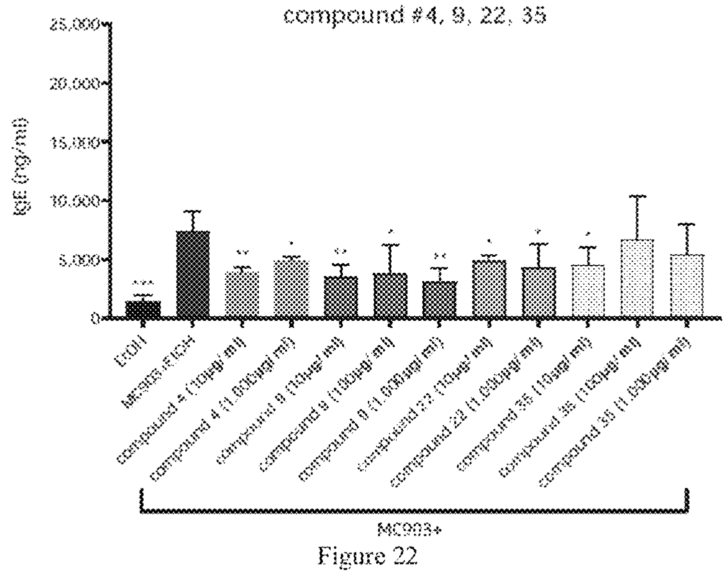
FIG. 22 depicts schematic diagrams of the total serum IgE levels of the mice in each group in Embodiment 33.
Figure 23:
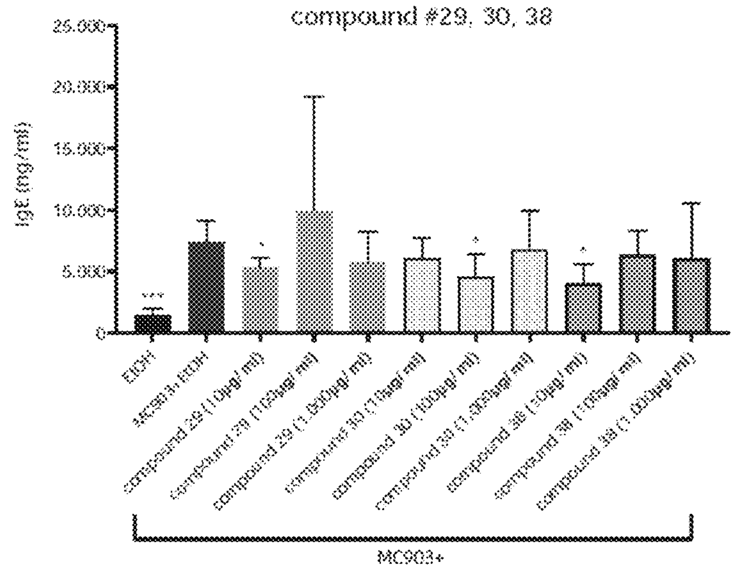
FIG. 23 depicts schematic diagrams of the total serum IgE levels of the mice in each group in Embodiment 33.
Figure 24:
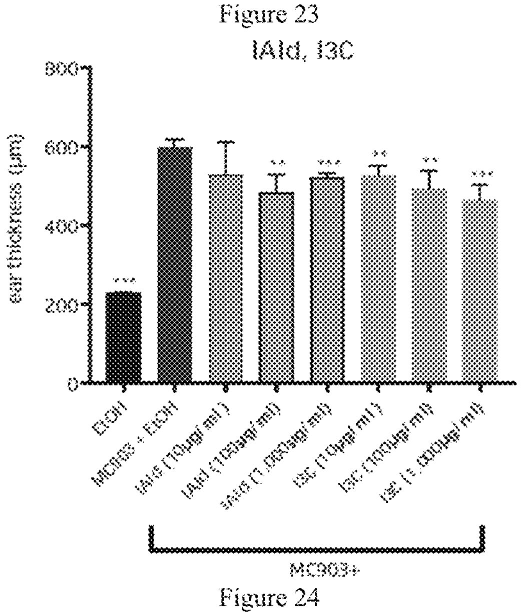
FIG. 24 depicts schematic diagrams of the ear thicknesses of the mice in each group in Embodiment 33.
Figure 25:
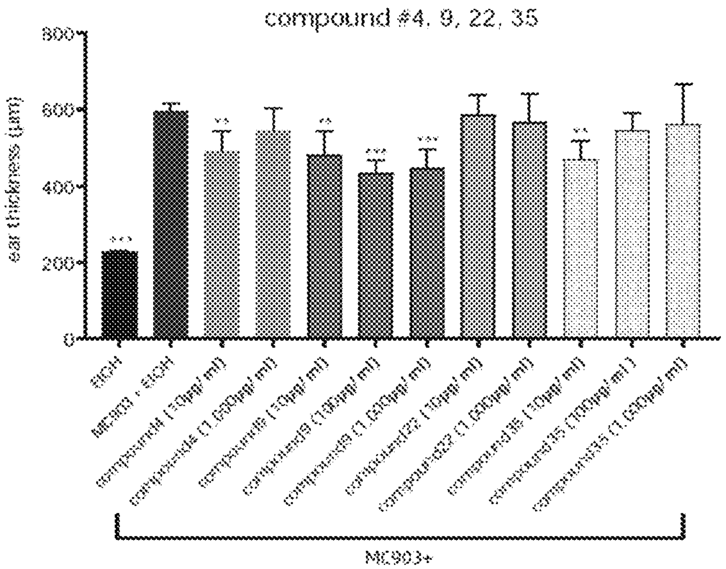
FIG. 25 depicts schematic diagrams of the ear thicknesses of the mice in each group in Embodiment 33.
Figure 26:
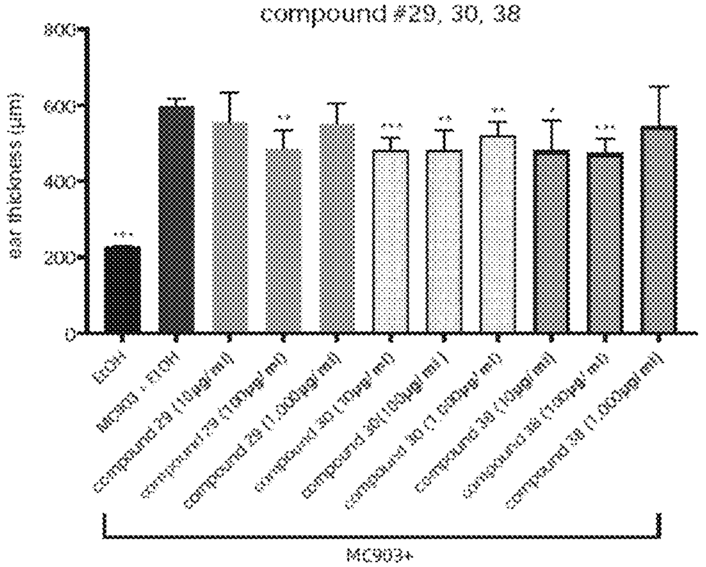
FIG. 26 depicts schematic diagrams of the ear thicknesses of the mice in each group in Embodiment 33.
Figure 27:
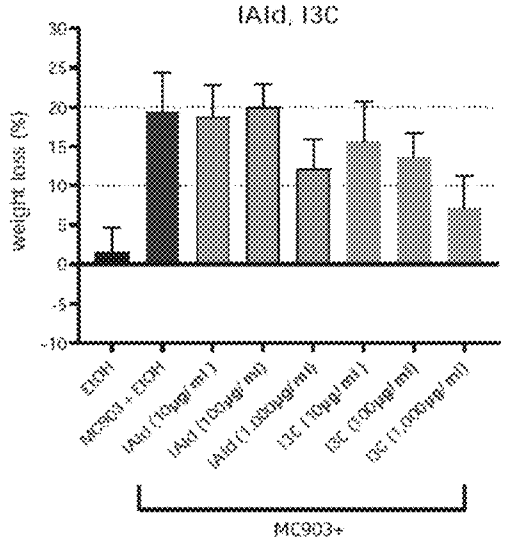
FIG. 27 depicts schematic diagrams of the weight loss of the mice in each group in Embodiment 33.
Figure 28:
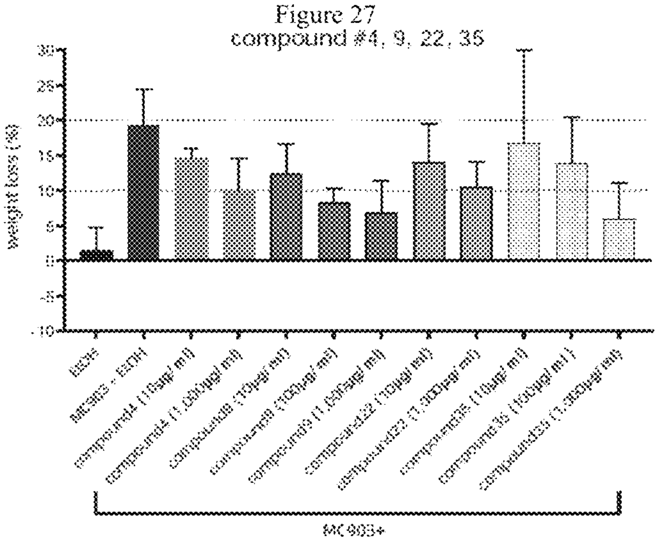
FIG. 28 depicts schematic diagrams of the weight loss of the mice in each group in Embodiment 33.
Figure 29:
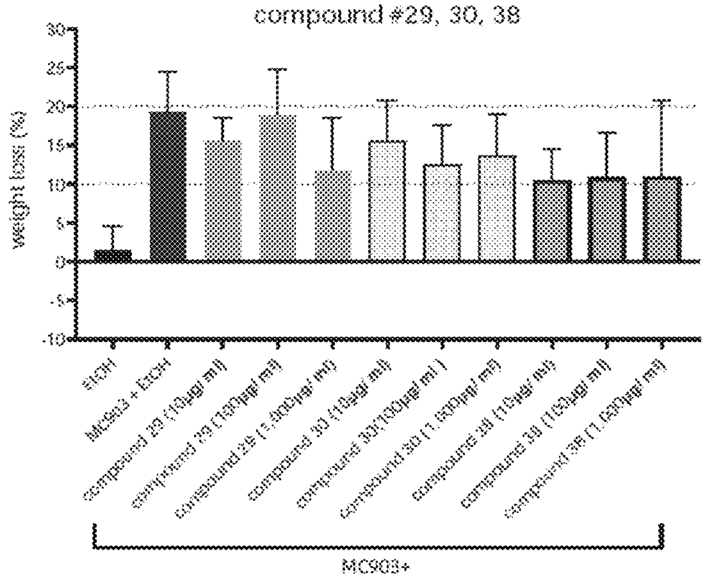
FIG. 29 depicts schematic diagrams of the weight loss of the mice in each group in Embodiment 33.
Figure 30:
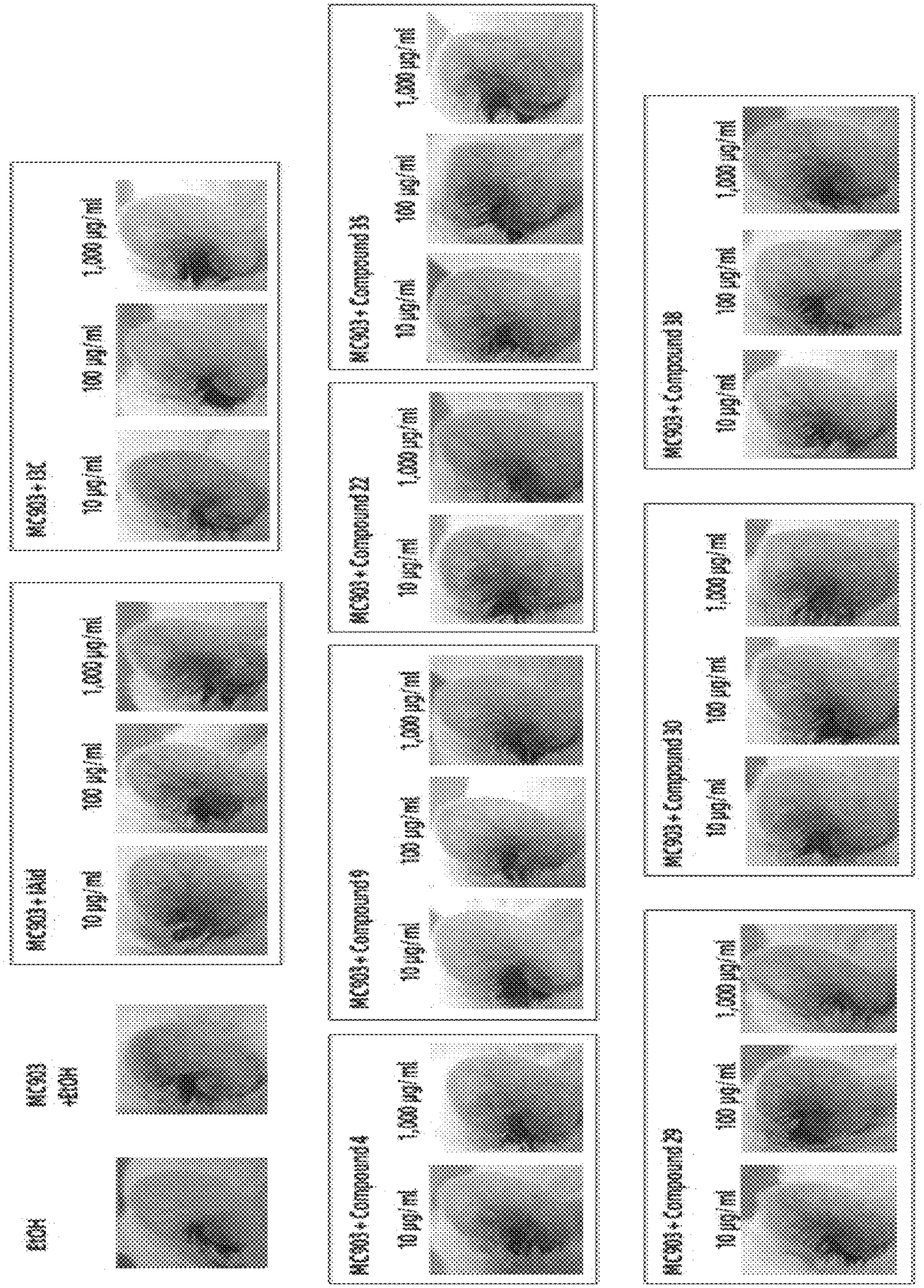
FIG. 30 depicts photographs of ears of representative mice in Embodiment 33.

The results are shown in FIGS. 21 to 30, wherein FIGS. 21 to 23 show the total serum levels of the mice in each group, FIGS. 24 to 26 show ear thicknesses of the mice in each group, FIGS. 27 to 29 show weight loss of the mice in each group, and FIG. 30 shows photographs of ears of the representative mice.

By comparing the differences in ear thicknesses, total serum IgE levels and weight loss of the mice in the treatment groups with those of the treatment group only administrated with MC903, it is found that Compound 9 had a significant therapeutic effect on AD-like symptoms in the mouse ear at different concentration. Compounds 4, 9, 29, 30, 38, 22, and 35, etc., had good inhibitory effect on systematic inflammation, manifested as lower total serum IgE levels and the improvement on AD-like symptoms in the mice ear, and in particular, Compounds 4, 30, and 38 had excellent inhibitory effect on systematic inflammation.

Embodiment 34

This embodiment provided a topical cream preparation.

1. Prescription of Substance

| | |
|---|---|
| Stearic acid | 120 g |
| Glyceryl monostearate | 35 g |
| Liquid paraffin | 60 g |

-continued

| | |
|---|---|
| Albolene | 10 g |
| Lanum | 50 g |
| Triethanolamine | 4 g |
| Distilled water | adding to 100.0 g |

2. Preparation 2.1 Substance Preparation.

Stearic acid, glyceryl monostearate, liquid paraffin, albolene, and lanum were taken as oil phase, placed in an evaporating dish, and heated to about 80° C. in a water bath for mixing and melting. Triethanolamine and distilled water were added in a flask and heated to about 80° C. in a water bath. The aqueous phase was gradually poured into the oil phase at an isothermal temperature and the mixture was stirred constantly in a water bath until it became milky semi-solid, which was then stirred at room temperature until it was nearly condensed to obtain the substance.

2.2 Cream Preparation

An active ingredient (each of compounds) in a pre-determined amount was added to the above substance. Alternatively, each of the compounds was dissolved and then added to the substance and stirred. While each of the ingredients/compounds was added under stirring, and evenly dispersed in the substance to obtain creams at different concentrations.

Although the present disclosure has been disclosed in the form of embodiments and variations thereon, it will be understood that numerous additional modifications and variations could be made thereto without departing from the scope of the disclosure.

For the sake of clarity, it is to be understood that the use of ‘a’ or ‘an’ throughout this application does not exclude a plurality, and ‘comprising’ does not exclude other steps or elements.

The invention claimed is:

1. A compound having a structure of formula I,

I

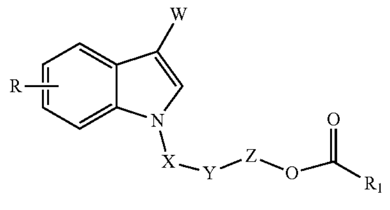

wherein,

W is $COR_2$, or $CR_3R_4OR_5$;

X is absent, or X is CO, or $CR_3R_4$;

Y is absent, or Y is O;

Z is absent, or Z is $CR_3R_4$;

$R_1$ is selected from the group consisting of $C_{5-15}$ alkyl, acetoxyl-substituted aryl, (2,6-dichlorophenyl)amino-substituted aryl, and pentaoxapentadecanyl;

R is selected from the group consisting of H, and D;

each of $R_2$, $R_3$, and $R_4$ is independently selected from the group consisting of H, D, $C_{2-6}$ alkyl, $C_{1-6}$ alkenyl, aryl, and heteroaryl; and $R_5$ is H, D, or $COR_1$.

2. The compound according to claim 1, wherein the compound has a structure as shown in formula II:

II

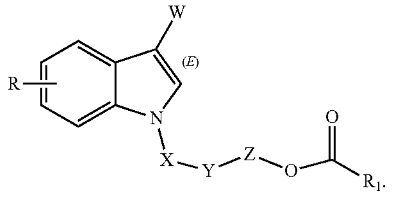

3. The compound according to claim 1, wherein,

W is $COR_2$, or $CR_3R_4OR_5$;

X is absent, or X is CO;

Y is absent, or Y is O;

Z is absent, or Z is $CR_3R_4$;

R is H; and each of $R_2$, $R_3$, $R_4$, and $R_5$ is H.

4. The compound according to claim 1, wherein,

W is COH, or $CH_2OH$;

X—Y—Z is $COOCH_2$, or $CH_2$;

$R_1$ is selected from the group consisting of $C_7$-$C_{15}$ alkyl, acetoxyl-substituted aryl, (2,6-dichlorophenyl)amino-substituted aryl, and pentaoxapentadecanyl; and R is H.

5. The compound according to claim 4, wherein,

W is COH;

X—Y—Z is $CH_2$;

$R_1$ is selected from the group consisting of $C_7$-$C_{15}$ alkyl, acetoxyl-substituted aryl, (2,6-dichlorophenyl)amino-substituted aryl, and pentaoxapentadecanyl; and R is H.

6. The compound according to claim 1, wherein, the compound is selected from the group consisting of:

Compound 1

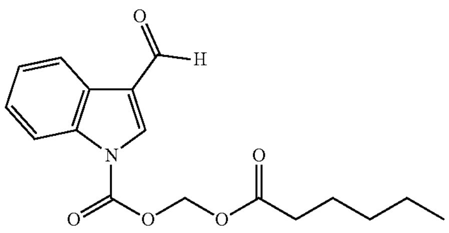

Compound 2

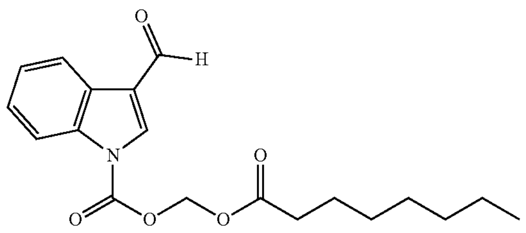

-continued
Compound 3
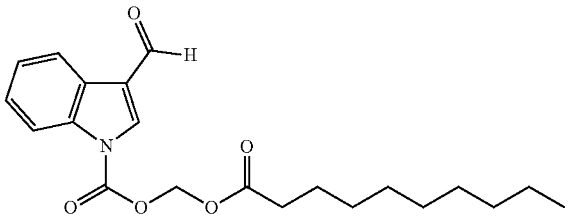
Compound 4
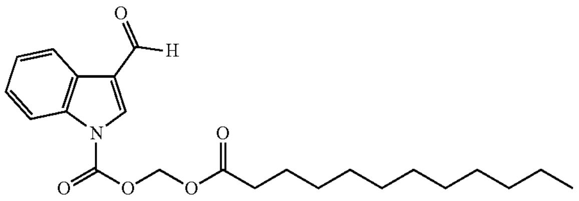
Compound 5
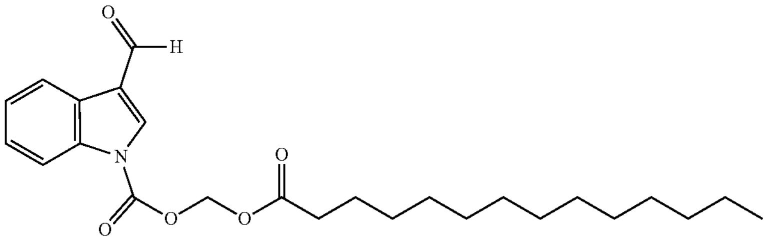
Compound 6
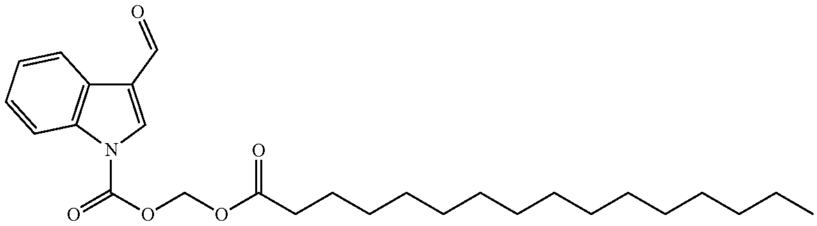
Compound 7
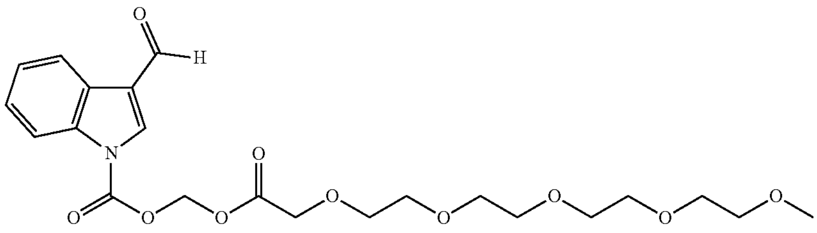
Compound 8
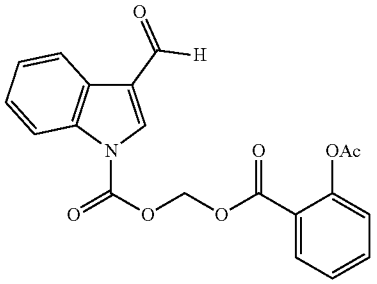
Compound 9
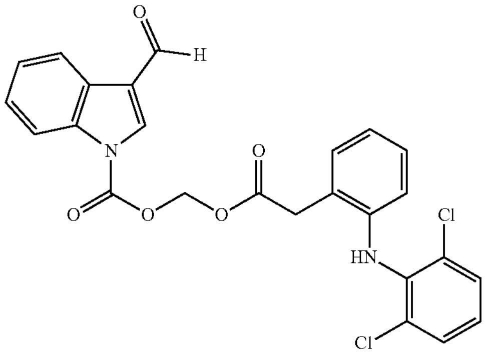
Compound 19
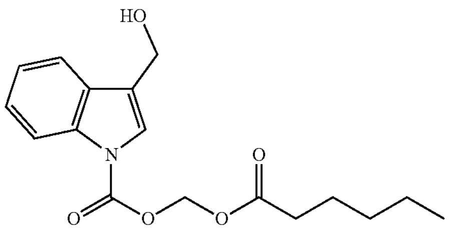
Compound 20
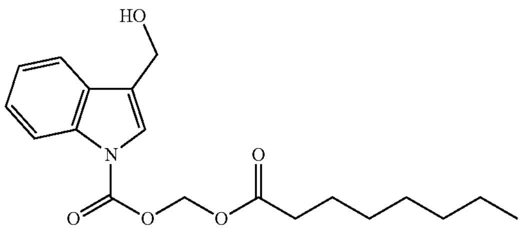

-continued
Compound 21
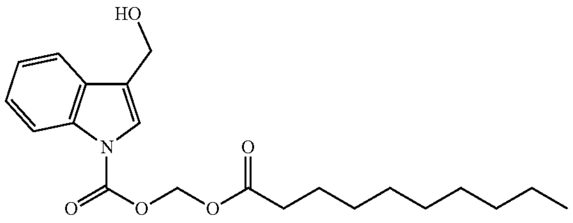
Compound 22
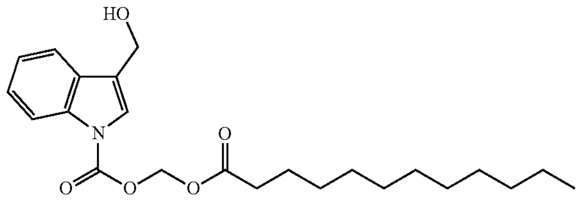
Compound 23
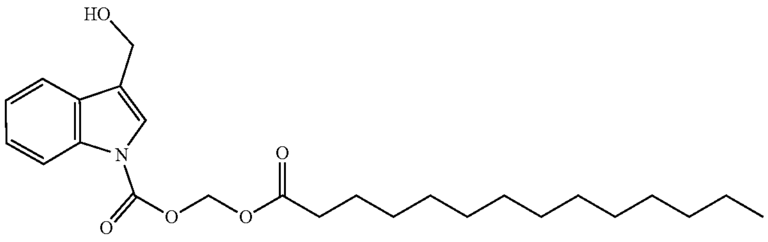
Compound 24
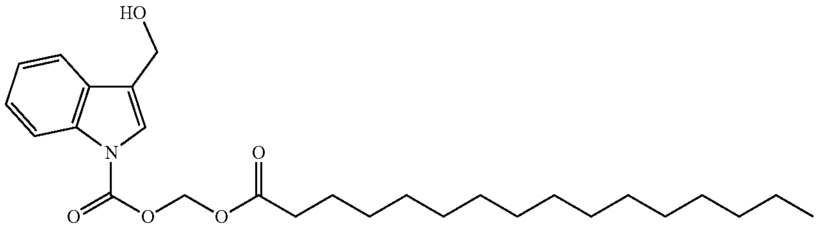
Compound 26
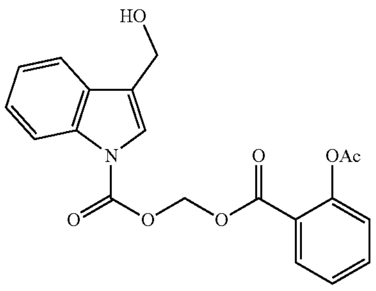
Compound 27
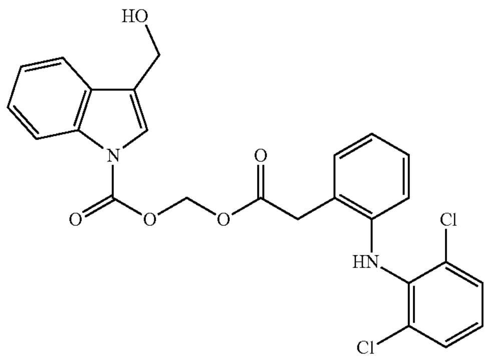
Compound 28
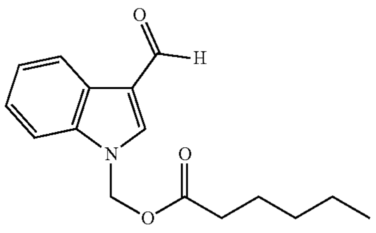
Compound 29
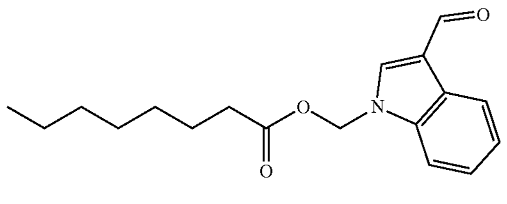
Compound 30
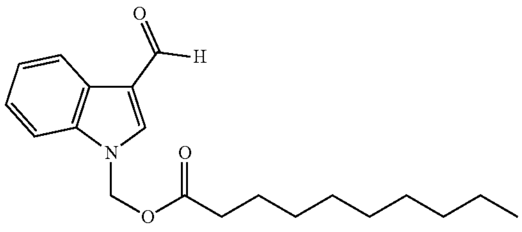
Compound 31
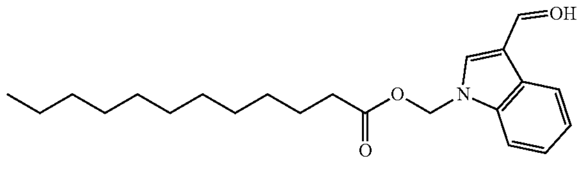

-continued
Compound 32
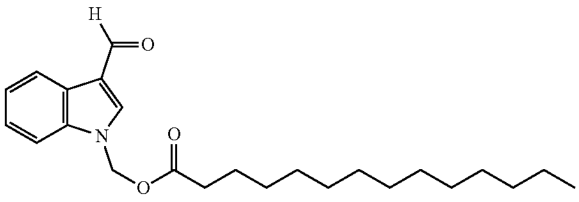
Compound 33
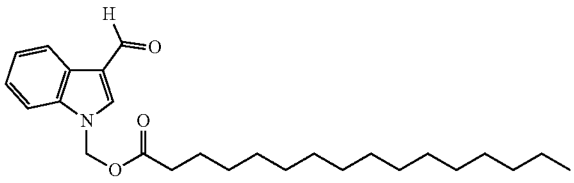
Compound 34
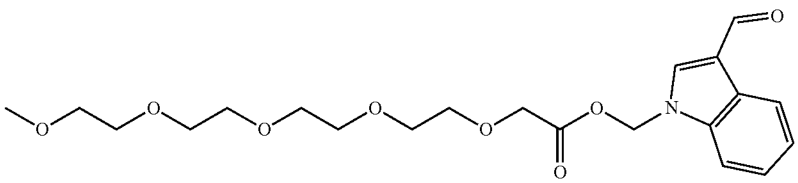
Compound 35
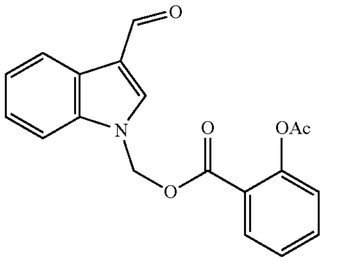
Compound 37
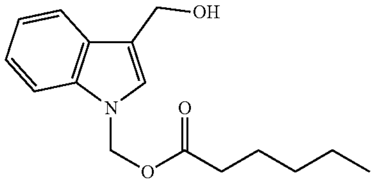
Compound 38
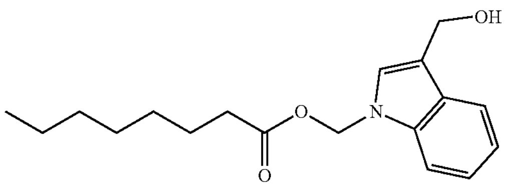
Compound 39
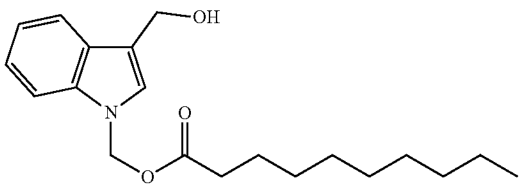
Compound 40
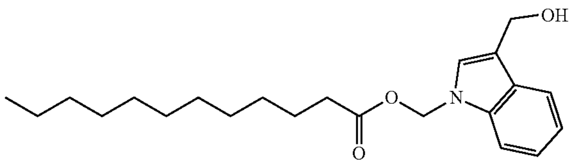
Compound 41
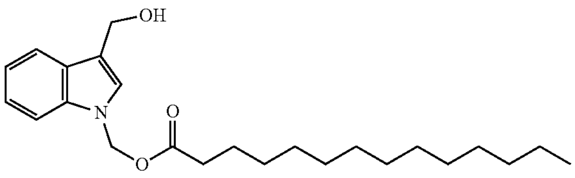
Compound 42
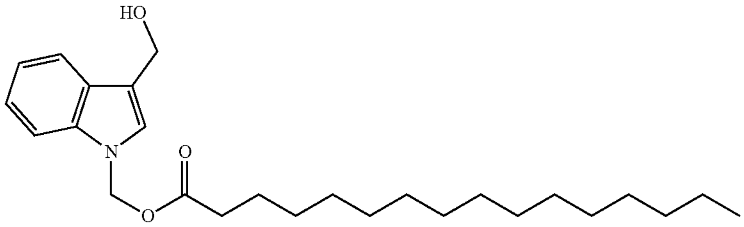
.

7. The compound according to claim 6, wherein, the Compound 4 has characteristic peaks at 2θ of 4.9±0.2°, 7.3±0.2°, 9.9±0.2°, 14.9±0.2°, and 22.0±0.2° in an X-ray powder diffraction pattern using Cu-Kα radiation;

the Compound 8 has characteristic peaks at 2θ of 5.2±0.2°, 11.6±0.2°, 12.6±0.2°, 16.0 0.2°, and 19.3±0.2° in an X-ray powder diffraction pattern using Cu-Kα radiation;

the Compound 9 has characteristic peaks at 2θ of 12.3±0.2°, 14.9±0.2°, 19.9±0.2°, 23.4±0.2°, and 27.3±0.2° in an X-ray powder diffraction pattern using Cu-Kα radiation;

the Compound 22 has characteristic peaks at 2θ of 3.4±0.2°, 5.3±0.2°, 6.9±0.2°, 10.2±0.2°, and 19.9±0.2° in an X-ray powder diffraction pattern using Cu-Kα radiation;

the Compound 23 has characteristic peaks at 2θ of 10.6±0.2°, 11.0±0.2°, 18.4±0.2°, 21.2±0.2°, and 21.7±0.2° in an X-ray powder diffraction pattern using Cu-Kα radiation;

the Compound 24 has characteristic peaks at 2θ of 4.4±0.2°, 6.6±0.2°, 8.9±0.2°, 21.0 0.2°, and 22.6±0.2° in an X-ray powder diffraction pattern using Cu-Kα radiation;

the Compound 26 has characteristic peaks at 2θ of 3.6±0.2°, 10.5±0.2°, 11.8±0.2°, 13.9±0.2°, and 19.7±0.2° in an X-ray powder diffraction pattern using Cu-Kα radiation;

the Compound 27 has characteristic peaks at 2θ of 6.5±0.2°, 10.2±0.2°, 13.2±0.2°, 15.0±0.2°, and 23.8±0.2° in an X-ray powder diffraction pattern using Cu-Kα radiation;

the Compound 35 has characteristic peaks at 2θ of 12.4±0.2°, 14.7±0.2°, 15.3±0.2°, 17.3±0.2°, and 23.5±0.2° in an X-ray powder diffraction pattern using Cu-Kα radiation; and the Compound 41 has characteristic peaks at 2θ of 3.1±0.2°, 5.2±0.2°, 6.7±0.2°, 10.2±0.2°, and 19.9±0.2° in an X-ray powder diffraction pattern using Cu-Kα radiation.

8. A pharmaceutical composition, comprising the compound according to claim 1, and a pharmaceutically acceptable excipient.

9. The pharmaceutical composition according to claim 8, wherein a dosage form of the pharmaceutical composition is a tablet, a dispersing agent, a tincture, a gel, a capsule, a spray, a suppository, an oral liquid, or a granule.

10. The pharmaceutical composition according to claim 8, wherein a dosage form of the pharmaceutical composition is a topical preparation.

11. A method of treating atopic dermatitis in a mammal in need thereof, comprising administering the compound according to claim 1.

12. The compound according to claim 2, wherein:

W is $COR_2$, or $CR_3R_4OR_5$;

X is absent, or X is CO;

Y is absent, or Y is O;

Z is absent, or Z is $CR_3R_4$;

R is H; and each of $R_2$, $R_3$, $R_4$, and $R_5$ is H.

13. The compound according to claim 2, wherein:

W is COH, or $CH_2OH$;

X—Y—Z is $COOCH_2$, or $CH_2$;

$R_1$ is selected from the group consisting of $C_7$-$C_{15}$ alkyl, acetoxyl-substituted aryl, (2,6-dichlorophenyl)amino-substituted aryl, and pentaoxapentadecanyl; and R is H.

14. The compound according to claim 2, wherein:

W is COH;

X—Y—Z is $CH_2$;

$R_1$ is selected from the group consisting of $C_7$-$C_{15}$ alkyl, acetoxyl-substituted aryl, (2,6-dichlorophenyl)amino-substituted aryl, and pentaoxapentadecanyl; and R is H.

* * * * *